(12) United States Patent
Paushkin et al.

(10) Patent No.: US 8,932,818 B2
(45) Date of Patent: Jan. 13, 2015

(54) SCREENING ASSAYS FOR COMPOUNDS THAT MODULATE PROGRAMMED RIBOSOMAL FRAMESHIFTING

(75) Inventors: Sergey V. Paushkin, Belle Mead, NJ (US); Nikolai A. Naryshkin, East Brunswick, NJ (US); Ellen Welch, Califon, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 220 days.

(21) Appl. No.: 13/058,613

(22) PCT Filed: Aug. 13, 2009

(86) PCT No.: PCT/US2009/004636
§ 371 (c)(1),
(2), (4) Date: Feb. 11, 2011

(87) PCT Pub. No.: WO2010/019243
PCT Pub. Date: Feb. 18, 2010

(65) Prior Publication Data
US 2011/0213005 A1 Sep. 1, 2011

Related U.S. Application Data

(60) Provisional application No. 61/088,649, filed on Aug. 13, 2008, provisional application No. 61/156,429, filed on Feb. 27, 2009.

(51) Int. Cl.
*C12Q 1/68* (2006.01)
*C12Q 1/66* (2006.01)
*C12Q 1/48* (2006.01)
*C12Q 1/34* (2006.01)
*C12Q 1/02* (2006.01)

(52) U.S. Cl.
CPC .................................. *C12Q 1/6897* (2013.01)
USPC .................. 435/6.13; 435/8; 435/15; 435/18; 435/29

(58) Field of Classification Search
None
See application file for complete search history.

(56) References Cited

U.S. PATENT DOCUMENTS

| | | |
|---|---|---|
| 2005/0054836 A1 | 3/2005 | Krainer et al. |
| 2007/0059684 A1* | 3/2007 | Peltz et al. ........................ 435/5 |
| 2007/0292408 A1 | 12/2007 | Singh et al. |
| 2011/0086833 A1 | 4/2011 | Paushkin et al. |
| 2011/0172284 A1 | 7/2011 | Paushkin et al. |

FOREIGN PATENT DOCUMENTS

| | | |
|---|---|---|
| WO | WO 01/66129 | 9/2001 |
| WO | WO 2004/113867 | 12/2004 |
| WO | WO 2007/002390 | 1/2007 |
| WO | WO 2007/109211 | 9/2007 |
| WO | WO 2009/151546 | 12/2009 |
| WO | WO 2010/019236 | 2/2010 |
| WO | WO 2010/019243 | 2/2010 |

OTHER PUBLICATIONS

Boda et al., 2004, "Survival motor neuron SMN1 and SMN2 gene promoters: identical sequences and differential expression in neurons and non-neuronal cells," Eur J Hum Genet.; 12(9):729-37.
Brahe et al., 2005, "Phenylbutyrate increases SMN gene expression in spinal muscular atrophy patients," Eur J Hum Genet.; 13(2):256-9.
Carrel et al., 2006, "Survival motor neuron function in motor axons is independent of functions required for small nuclear ribonucleoprotein biogenesis", Journal of Neuroscience; 26(43):11014-11022.
Cartegni et al., 2002, "Disruption of an SF2/ASF-dependent exonic splicing enhancer in SMN2 causes spinal muscular atrophy in the absence of SMN1," Nature Genetics; 30:377-384.
Cartegni et al., 2006, "Determinants of exon 7 splicing in the spinal muscular atrophy genes, SMN1 and SMN2," American Journal of Human Genetics; 78:63-77.
Echaniz-Laguna et al., 1999, "The promoters of the survival motor neuron gene (SMN) and its copy (SMNc) share common regulatory elements," Am J Hum Genet; 64(5):1365-70.
GenBank accession No. EF540695.1, "Expression vector proSMN2:SMN2:luc, complete sequence" May 2008.
Germain-Desprez et al., 2001, "The SMN genes are subject to transcriptional regulation during cellular differentiation," Gene; 279:109-117.
Gubitz et al., 2004 "The SMN complex," Exp Cell Res.; 296:51-6.
Iannaconne et al., 2002 "Outcome Measures for Pediatric Spinal Muscular Atrophy," Arch Neurol. 59:1445-1450.
Iannaconne et al., 2003, "Reliability of 4 Outcome Measures in Pediatric Spinal Muscular Atrophy," Arch Neurol; 60:1130-1136.
Jarecki et al., 2005 "Diverse small-molecule modulators of SMN expression found by high-throughput compound screening: early leads towards a therapeutic for spinal muscular atrophy," Hum Mol Genet.; 14(14):2003-18.
Kashima et al., 2003, "A negative element in SMN2 exon 7 inhibits splicing in spinal muscular atrophy," Nature Genetics; 34(4):460-463.
Kolb et al., 2006, "A novel cell immunoassay to measure survival of motor neurons protein in blood cells," BMC Neurology, 6:6.
Le et al., 2005, "SMNΔ7, the major product of the centromeric survival motor neuron (SMN2) gene, extends survival in mice with spinal muscular atrophy and associates with full-length SMN", Human Molecular Genetics; 14(6):845-857.
Lorson et al., 1999, "A single nucleotide in the SMN gene regulates splicing and is responsible for spinal muscular atrophy," Proc Natl Acad Sci USA; 96:6307-6311.

(Continued)

Primary Examiner — Jennifer Dunston
(74) Attorney, Agent, or Firm — Jones Day

(57) ABSTRACT

The present invention relates to compounds that modulate ribosomal frameshifting and nucleic acid constructs for use in methods for identifying or validation of compounds that modulate ribosomal frameshifting. In particular, the present invention relates to the use of nucleic acid constructs to identify or validate compounds capable of modulating the efficiency of programmed ribosomal frameshifting and the use of compounds that modulate the efficiency of programmed ribosomal frameshifting to inhibit the replication or infectivity of viruses that employ programmed ribosomal frameshifting.

16 Claims, 4 Drawing Sheets

(56) References Cited

OTHER PUBLICATIONS

Lorson et al., 2000, "An exonic enhancer is required for inclusion of an essential exon in the SMA-determining gene SMN," Human Molecular Genetics; 9(2):259-265.

Lunn et al., 2004, "Indoprofen upregulates the survival motor neuron protein through a cyclooxygenase-independent mechanism", Chemistry & Biology; 11:1489-1493.

Mattis et al., 2006, "Novel aminoglycosides increase SMN levels in spinal muscular atrophy fibroblasts," Human Genetics; pp. 1-13.

Mattis et al., 2008, "A SMN Δ7 read-through product confers functionality to the SMN Δ7 protein," Neuroscience Letters; 442:54-58.

Merlini et al., 2003, "Role of gabapentin in spinal muscular atrophy: results of a multicenter, randomized Italian study," J Child Neurol.; 18(8):537-41.

Monani et al., 1999, Promoter analysis of the human centromeric and telomeric survival motor neuron genes (SMNC and SMNT), Biochim Biophys Acta; 1445(3):330-6.

Paushkin et al.., 2002 "The SMN complex, an assemblyosome of ribonucleoproteins" Curr Opin Cell Biol., 14:305-12.

Rochette et al., 2001, "SMN gene duplication and the emergence of the SMN2 gene occurred in distinct hominids: SMN2 is unique to *Homo sapiens*", Human Genetics; 108(3):255-266.

Schmid et al., 2007, "Animal models of spinal muscular atrophy", Journal of Child Neurology; 22(8):1004-1012.

Singh et al., "In vivo selection reveals combinatorial controls that define a critical exon in the spinal muscular atrophy genes," RNA: 10:1291-1305.

Singh et al., 2007, "Modulating role of RNA structure in alternative splicing of a critical exon in the spinal muscular atrophy genes", Nucleic Acids Research; 35(2):371-389.

Sumner et al., 2006, "SMN mRNA and protein levels in peripheral blood: biomarkers for SMA clinical trials," Neurology, 66:1067-1073.

Sumner, 2006, "Therapeutics development for spinal muscular atrophy," NeuroRx; 3(2):235-245.

Wan, 2005, "The survival of motor neurons protein determines the capacity for snRNP assembly: biochemical deficiency in spinal muscular atrophy," Molec & Cell Biol, 25(13): 5543-5551.

Wilson et al., 2007, "An SMA project report: neural cell-based assays derived from human embryonic stem cells", Stem Cells and Development; 16:1027-1041.

Wolstencroft et al., 2005, "A non-sequence-specific requirement for SMN protein activity: the role of aminoglycosides in inducing elevated SMN protein levels," Hum Mol Genet, 14(9):1199-1210.

Yeo, 2005, "Splicing regulators: targets and drugs", Genome Biology 6(12):240.

Yong et al., 2004, "Why do cells need an assembly machine for RNA—protein complexes," Trends in Cell Biology; 15(5):226-232.

Yuo et al., 2008, "5-(N-ethyl-N-isopropyl)-amiloride enhances SMN2 exon 7 inclusion and protein expression in spinal muscular atrophy cells", Annals of Neurology; 63(1):26-34.

Zhang et al., 2001, "An in vivo reporter system for measuring increased inclusion of exon 7 in SMN2 m RNA: potential therapy of SMA", Gene Therapy; 8(20):1532-1538.

* cited by examiner tagcttcttacccgtactccaccgttggcagcacgatcgcacgtcccacgtgaaccattggtaaaccctgatgggatccata
attccccaccacctcccatatgtccagattctcttgatgatgctgatgctttgggaagtatgttaatttcatggtacatgagtgg
ctatcatactggctattatatggtaagtaatcactcagcatcttttcctgacaattttttgtagttatgtgactttgttttgtaaatttat
aaaatactacttgcttctctctttatattactaaaaaataaaaataaaaaaatacaactgtctgaggcttaaattactcttgcattgt
ccctaagtataattttagttaattttaaaaagctttcatgctattgttagattattttgattatacacttttgaattgaaattatactttttct
aaataatgttttaatctctgatttgaaattgattgtagggaatggaaaagatgggataatttttcataaatgaaaaatgaaattcttt
ttttttttttttttttttttgagacggagtcttgctctgttgcccaggctggagtgcaatggcgtgatcttggctcacagcaagctctg
cctcctggattcacgccattctcctgcctcagcctcagaggtagctgggactacaggtgcctgccaccacgcctgtctaattt
tttgtatttttttgtaaagacagggtttcactgtgttagccaggatggtctcaatctcctgacccgtgatccaccgcctcggcc
ttccaagagaaatgaaattttttaatgcacaaagatctggggtaatgtgtaccacattgaaccttggggagtatggcttcaaa
cttgtcacttatacgttagtctcctacggacatgttctattgtattttagtcagaacatttaaaattatttatttattttattttttttttttt
tttgagacggagtctcgctctgtcacccaggctggagtacagtggcgcagtctcggctcactgcaagctccgcctcccggg
ttcacgccattctcctgcctcagcctctccgagtagctgggactacaggcgcccgccaccacgcccggctaatttttttttattt
ttagtagagacggggtttcaccgtggtctcgatctcctgacctcgtgatccacccgcctcggcctcccaaagtgctgggatta
caagcgtgagccaccgcgcccggcctaaaattattttaaaagtaagctcttgtgccctgctaaaattatgatgtgatattgtag
gcacttgtattttagtaaattaatatagaagaaacaactgacttaaaggtgtatgttttaaatgtatcatctgtgtgtgcccccat
taatattcttatttaaaagttaaggccagacatggtggcttacaactgtaatcccaacagtttgtgaggccgaggcaggcagat
cacttgaggtcaggagtttgagaccagcctggccaacatgatgaaaccttgtctctactaaaaataccaaaaaaaatttagcc
aggcatggtggcacatgcctgtaatccgagctactgggaggctgtggcaggaaaattgctttaatctgggaggcagaggt
tgcagtgagttgagattgtgccactgcactccacccttggtgacagagtgagattccatctcaaaaaaagaaaaaggcctgg
cacggtggctcacacctataatcccagtactttgggaggtagaggcaggtggatcacttgaggttaggagttcaggaccag
cctggccaacatggtgactactccatttctactaaatacacaaaacttagcccagtggcgggcagttgtaatcccagctactt
gagaggttgaggcaggagaatcacttgaacctgggaggcagaggttgcagtgagccgagatcacaccgctgcactctag
cctggccaacagagtgagaatttgcggagggaaaaaaaagtcacgcttcagttgttgtagtataaccttggtatattgtatgta
tcatgaattcctcatttaatgaccaaaaagtaataaatcaacagcttgtaatttgttttgagatcagttatctgactgtaacactgt
aggcttttgtgttttttaaattatgaaatatttgaaaaaaatacataatgtatatataaagtattggtataatttatgttctaaataactt
tcttgagaaataattcacatggtgtgcagtttacctttgaaagtatacaagttggctgggcacaatggctcacgcctgtaatcc
cagcactttgggaggccagggcaggtggatcacgaggtcaggagatcgagaccatcctggctaacatggtgaaaccccg
tctctactaaaagtacaaaaacaaattagccgggcatgttggcgggcaccttttgtcccagctgctcgggaggctgaggca
ggagagtggcgtgaacccaggaggtggagcttgcagtgagccgagattgtgccagtgcactccagcctgggcgacaga
gcgagactctgtctcaaaaaataaaataaaaaagaaagtatacaagtcagtggttttggtttcagttatgcaaccatcactac
aatttaagaacattttcatcaccccaaaaagaaaccctgttaccttcattttccccagcccaggcagtcagtacactttctgtct
ctatgaatttgtctattttagatattatatataaacggaattatacgatatgtggtcttttgtgtctggcttcttcacttagcatgctat
tttcaagattcatccatgctgtagaatgcaccagtactgcattccttcttattgctgaatattctgttgtttggttatatcacatttat
ccattcatcagttcatggacatttaggttgttttttatttttgggctataatgaataatgttgctatgaacattcgtttgtgttctttttgttt
ttttggtttttttgggttttttttgttttgttttgttttgagacagtcttgctctgtctcctaagctggagtgcagtggcatgatcttggc
ttactgcaagctctgcctcccgggttcacaccattctcctgcctcagcccgacaagtagctgggactacaggcgtgtgccac
catgcacggctaattttttgtattttagtagagatggggtttcaccgtgttagccaggatggtctcgatctcctgacctcgtgat
ctgcctgcctaggcctcccaaagtgctgggattacaggcgtgagccactgcacctggccttaagtgttttaatacgtcattg
ccttaagctaacaattcttaacctttgttctactgaagccacgtggttgagataggctctgagtctagcttttaacctctatctttt
gtcttagaaatctaagcagaatgcaaatgactaagaataatgttgttgaaataacataaaataggttataactttgatactcatta
gtaacaaatctttcaatacatcttacggtctgttaggtgtagattagtaatgaagtgggaagccactgcaagctagtatacatgt
agggaaagatagaaagcattgaagccagaagagagacagaggacatttgggctagatctgacaagaaaaacaaatgtttt
agtattaattttgacttaaattttttttttatttagtgaatactggtgtttaatggtctcatttttaataagtatgacacaggtagtttaa
ggtcatatatttttatttgatgaaaataaggtataggccgggcacggtggctcacacctgtaatcccagcactttgggaggccg
aggcaggcggatcacctgaggtcgggagttagagactagcctcaacatggagaaaccccgtctctactaaaaaaaataca
aaattaggcgggcgtggtggtgcatgcctgtaatcccagctactcaggaggctgaggcaggagaattgcttgaacctggg

FIG. 2A aggtggaggttgcggtgagccgagatcacctcattgcactccagcctgggcaacaagagcaaaactccatctcaaaaaaa
aaaaaataaggtataagcgggctcaggaacatcattggacatactgaaagaagaaaaatcagctgggcgcagtggctcac
gccggtaatcccaacactttgggaggccaaggcaggcgaatcacctgaagtcgggagttccagatcagcctgaccaacat
ggagaaaccctgtctctactaaaaatacaaaactagccgggcatggtggcgcatgcctgtaatcccagctacttgggaggc
tgaggcaggagaattgcttgaaccgagaaggcggaggttgcggtgagccaagattgcaccattgcactccagcctgggc
aacaagagcgaaactccgtctcaaaaaaaaaggaagaaaaatattttttaaattaattagtttatttattttttaagatggagttt
tgccctgtcacccaggctggggtgcaatggtgcaatctcggctcactgcaacctccgcctcctgggttcaagtgattctcctg
cctcagcttcccgagtagctgtgattacagccatatgccaccacgcccagccagttttgtgttttgttttgttttttgtttttttttttg
agagggtgtcttgctctgtcccccaagctggagtgcagcggcgcgatcttggctcactgcaagctctgcctcccaggttcac
accattctcttgcctcagcctcccgagtagctgggactacaggtgcccgccaccacacccggctaattttttgtgttttagta
gagatgggtttcactgtgttagccaggatggtctcgatctcctgacctttgatccacccgcctcagcctcccaagtgctg
ggattataggcgtgagccactgtgcccggcctagtcttgtatttttagtagagtcgggatttctccatgttggtcaggctgttctc
caaatccgacctcaggtgatccgcccgccttggcctccaaaagtgcaaggcaaggcattacaggcatgagccactgtgac
cggcaatgttttttaaattttttacatttaaatttattttttagagaccaggtctcactctattgctcaggctggagtgcaagggcac
attcacagctcactgcagccttgacctccagggctcaagcagtcctctcacctcagtttcccgagtagctgggactacagtg
ataatgccactgcacctggctaattttttattttatttatttattttttttgagacagagtcttgctctgtcacccaggctggagtgca
gtggtgtaaatctcagctcactgcagcctccgcctcctgggttcaagtgattctcctgcctcaacctcccaagtagctgggatt
agaggtcccaccaccatgcctggctaatttttgtactttcagtagaaacggggttttgccatgttggccaggctgttctcgaa
ctcctgagctcaggtgatccaactgtctcggcctcccaaagtgctgggattacaggcgtgagccactgtgcctagcctgag
ccaccacgccggcctaattttaaatttttgtagagacagggtctcattatgttgcccaggtgtgcaagctccaggtctca
agtgatccccctacctccgcctcccaaagtgtgggattgtaggcatgagccactgcaagaaaaccttaactgcagcctaat
aattgttttctttgggataacttttaaagtacattaaaagactatcaacttaatttctgatcatatttgttgaataaaataagtaaaat
gtcttgtgaaacaaaatgcttttaacatccatataaagctatctatatatagctatctatatctatatagctatttttttaacttcctttt
attttccttacagggttttagacaaaatcaaaaagaaggaaggtgctcacattccttaaatgtaaggagtaagtctgccagcat
tatgaaagtgaatcttacttttgtaaaactttatggtttgtggaaaacaaatgttttttgaacatttaaaaagttcagatgttagaaag
ttgaaaggttaatgtaaaacaatcaatattaaagaattttgatgccaaaactattagataaaaggttaatctacatccctactaga
attctcatacttaactggttggttgtgtggaagaaacatactttcacaataaagagctttaggatatgatgccatttttatatcacta
gtaggcagaccagcagacttttttttattgtgatatgggataacctaggcatactgcactgtacactctgacatatgaagtgctc
tagtcaagtttaactggtgtccacagaggacatggtttaactggaattcgtcaagcctctggttctaatttctcatttgcaggaaa
tgctggcatagagcagcacggatccgaagacgccaaaaacataaagaaaggcccggcgccattctatcctctagaggat
ggaaccgctggagagcaactgcataaggctatgaagagatacgccctggttcctggaacaattgcttttacagatgcacata
tcgaggtgaacatcacgtacgcggaatacttcgaaatgtccgttcggttggcagaagctatgaaacgatatgggctgaatac
aaatcacagaatcgtcgtatgcagtgaaaactctcttcaattctttatgccggtgttgggcgcgttatttatcggagttgcagttg
cgcccgcgaacgacatttataatgaacgtgaattgctcaacagtatgaacatttcgcagcctaccgtagtgtttgtttccaaaa
agggggttgcaaaaaattttgaacgtgcaaaaaaaattaccaataatccagaaaattattatcatggattctaaaacggattacc
agggatttcagtcgatgtacacgttcgtcacatctcatctacctcccggttttaatgaatacgattttgtaccagagtcctttgatc
gtgacaaaacaattgcactgataatgaattcctctggatctactgggttacctaagggtgtggcccttccgcatagaactgcct
gcgtcagattctcgcatgccagagatcctatttttggcaatcaaatcattccggatactgcgattttaagtgttgttccattccatc
acggttttggaatgtttactacactcggatatttgatatgtggatttcgagtcgtcttaatgtatagatttgaagaagagctgttttt
acgatcccttcaggattacaaaattcaaagtgcgttgctagtaccaacccctatttcattcttcgccaaaagcactctgattgac
aaatacgatttatctaatttacacgaaattgcttctggggggcgcacctctttcgaaagaagtcggggaagcggttgcaaaacg
cttccatcttccagggatacgacaaggatatgggctcactgagactacatcagctattctgattacacccgagggggatgat
aaaccgggcgcggtcggtaaagttgttccattttttgaagcgaaggttgtggatctggataccgggaaaacgctgggcgtta
atcagagaggcgaattatgtgtcagaggacctatgattatgtccggttatgtaaacaatccggaagcgaccaacgccttgatt
gacaaggatggatggctacattctggagacatagcttactgggacgaagacgaacacttcttcatagttgaccgcttgaagt
ctttaattaaatacaaaggatatcaggtggccccccgctgaattggaatcgatattgttacaacaccccaacatcttcgacgcg

FIG. 2B ggcgtggcaggtcttcccgacgatgacgccggtgaacttcccgccgccgttgttgttttggagcacggaaagacgatgac
ggaaaaagagatcgtggattacgtcgccagtcaagtaacaaccgcgaaaaagttgcgcggaggagttgtgtttgtggacg
aagtaccgaaaggtcttaccggaaaactcgacgcaagaaaaatcagagagatcctcataaaggccaagaagggcggaa
agtccaaattgcgcggccgctaaatcgaaagtacaggactagccttcctagcaaccgcgggctgggagtctgagacatca
ctcaagatatatgctcggtaacgtatgctctagccatctaactattccctatgtcttataggg
(SEQ ID NO:11)

FIG. 2C

SCREENING ASSAYS FOR COMPOUNDS THAT MODULATE PROGRAMMED RIBOSOMAL FRAMESHIFTING

This application is a national stage application of International Application No. PCT/US2009/004636, filed Aug. 13, 2009, which claims priority benefit of U.S. provisional application No. 61/088,649, filed Aug. 13, 2008, and U.S. provisional application No. 61/156,429, filed Feb. 27, 2009, each of which is incorporated herein by reference in its entirety.

INTRODUCTION

The present invention relates to compounds that modulate ribosomal frameshifting and nucleic acid constructs for use in methods for identifying or validation such compounds. In particular, the present invention relates to the use of nucleic acid constructs to identify or validate compounds capable of modulating the efficiency of programmed ribosomal frameshifting and the use of said compounds to inhibit the replication or infectivity of viruses that employ programmed ribosomal frameshifting.

BACKGROUND

Programmed ribosomal frameshifting is a specific mode of gene regulation designed to increase the informational content of small and limited viral genomes. Programmed ribosomal frameshifting in all viruses occurs by the same mechanism (Brierley, 1995, *J. Gen. Virol.*, 76:1885-1892; Farabaugh, 1997, "Programmed alternative reading of the genetic code," R.G. Landes Company, Austin, Tex.; Jacks, 1990, *Curr. Top. Microbiol. Immunol.* 157:93-124). Two basic RNA elements, a slippery site and downstream stem-loop structure, have been identified which are generally required to generate and regulate −1 ribosomal frameshifting (Brierley, 1995, *J. Gen. Virol.*, 76:1885-1892; Farabaugh, 1997, "Programmed alternative reading of the genetic code," R.G. Landes Company, Austin, Tex.; Bekaert, et al., 2003, *Bioinformatics*, 19:327-335; Dulude, et al., 2002, *Nucleic Acids Res.*, 30:5094-5102; Gaudin, et al., 2005, *J. Mol. Biol.*, 349:1024-1035; Staple, et al., 2005, *J. Mol. Biol.* 349:1011-1023). The slippery site consists of a stretch of seven nucleotides that do not have a uniform sequence but span three amino acid codons and must conform to the sequence X XXY YYZ (the gag ORF is indicated by spaces) where X is any nucleotide, Y is an A or U, and Z is A, U, or C (Brierley, et al., 1992, *J. Mol. Biol.* 227:463-479; Dinman, et al., 1991, *Proc. Natl. Acad. Sci. USA*, 88:174-178; Dinman, et al., 1992, *J. Virol.* 66:3669-3676; Jacks, et al., 1988, *Cell*, 55:447-458). Earlier studies indicate that the downstream sequence forms a pseudoknot (Brierley, 1995, *J. Gen. Virol*, 76:1885-1892; Farabaugh, 1997, "Programmed alternative reading of the genetic code," R.G. Landes Company, Austin, Tex.; Bekaert, et al., 2003, *Bioinformatics*, 19:327-335). However, recent data indicate that the downstream sequence forms a stem-loop structure (Dulude, et al., 2002, *Nucleic Acids Res.*, 30:5094-5102; Gaudin, et al., 2005, *J. Mol. Biol*, 349:1024-1035; Staple, et al., 2005, *J. Mol. Biol.* 349:1011-1023). The stem-loop is a sequence that forms a defined RNA secondary structure and is thought to regulate production of the Gag-Pol polyprotein (Brierley, et al., 1989, *Cell*, 57:537-547; Dinman, et al., 1991, *Proc. Natl. Acad. Sci.* USA, 88:174-178; Dulude, et al., 2002, *Nucleic Acids Res.*, 30:5094-5102; Morikawa, et al., 1992, *Virology*, 186:389-397; Plant, et al., 2003, *RNA*, 9:168-174; Somogyi, et al., 1993, *Mol. Cell. Biol.* 13:6931-6940; Tu, et al., 1992, *Proc. Natl. Acad. Sci. USA*, 89:8636-8640). The importance of the stem loop in programmed ribosomal frameshifting is evidenced by the fact that human immunodeficiency virus-1 (HIV-1) genomes with mutations in the stem loop have shown a reduction in frameshift activity and have been found to be profoundly defective in viral replication (Telenti, et al., 2002, *J. Virol.* 76:7868-7873).

The rate of programmed ribosomal frameshifting is strictly regulated. Small changes in either or both the slippery site and stem-loop have been shown to have profound effects on the efficiency of ribosomal frameshifting (Baril, et al., 2003, *RNA*, 9:1246-1253; Brierley, 1995, *J. Gen. Virol.*, 76:1885-1892; Dinman, 1995, *Yeast*, 11:1115-1127; Farabaugh, 1997, "Programmed alternative reading of the genetic code," R.G. Landes Company, Austin, Tex.). The sequences of the RNA elements may affect the secondary structure and thermodynamic stability of the stem-loop. Furthermore, these sequences can affect the relative position of the RNA stem-loop in relation to the slippery site, in turn affecting the ability of the ribosome-bound tRNAs to unpair from the 0-frame codon, and thus the ability of these tRNAs to then pair with the −1 frame codon (Brierley, et al., 1989, *Cell*, 57:537-547; Brierley, et al., 1992, *J. Mol. Biol.* 227:463-479; Brierley, et al., 1991, *J. Mol. Biol.* 220:889-902; Dinman, et al., 1991, *Proc. Natl. Acad. Sci. USA*, 88:174-178; Dinman, et al, 1992, *J. Virol.* 66:3669-3676; Honda, et al, 1995, *Biochem. Biophys. Res. Commun.* 213:575-582; Jacks, et al., 1988, *Cell*, 55:447-458; Jacks, et al., 1988, *Nature*, 331:280-283; Morikawa, et al., 1992, *Virology*, 186:389-397; Namy, et al., 2006, *Nature*, 441:244-247).

Several viruses have been shown to utilize −1 programmed ribosomal frameshifting to produce the Gag-Pol polyprotein. Frameshifting ensures that the correct ratio of viral structural proteins (Gag) to non-structural proteins (Pol) is maintained in the cytoplasm (Brierley, 1995, *J. Gen. Virol.*, 76:1885-1892). The maintenance of a precise ratio of Gag to Gag-Pol synthesis for viral propagation has been demonstrated for a number of retroviruses as well as for endogenous viruses of the yeast *Saccharomyces cerevisiae* (Dinman, et al., 1998, *Trends Biotech.* 16(4):3669-3676; Telenti, et al., 2002, *J. Virol.* 76:7868-7873). The ratio of HIV-1 Gag to Gag-Pol synthesized as a consequence of −1 programmed ribosomal frameshifting varies within a narrow window of approximately 10:1 to 20:1 (Farabaugh, 1997, "Programmed alternative reading of the genetic code," R.G. Landes Company, Austin, Tex.; Jacks, et al., 1988, *Nature*, 331:280-283; Telenti, et al., 2002, *J. Virol.* 76:7868-7873). Changing the ratio of Gag to Gag-Pol proteins in retroviruses like HIV-1 or Moloney murine leukemia virus interferes with particle formation and replication (Farabaugh, 1997, "Programmed alternative reading of the genetic code," R.G. Landes Company, Austin, Tex.; Felsenstein, et al., 1988, *J. Virol.* 62(6):2179-2182; Karacostas, et al., 1993, *Virology*, 193:661-671; Park, et al., 1991, *J. Virol.* 65(9):5111-5117). For example, overexpression of the Gag-Pol precursor protein results in the inefficient processing of the polyprotein and consequently inhibition of virus production. It has been shown that maintaining the proper ratio of Gag to Gag-Pol is necessary for proteolytic processing as well as for RNA dimerization (essential for the packaging of the viral RNA genome) and viral infectivity (Hill, et al., 2002, *J. Virol.* 76:11245-11253; Shehu-Xhilaga, et al., 2001, *J. Virol.* 75(4):1834-1841).

Clearly, alterations in programmed ribosomal frameshifting efficiencies can have a pronounced negative effect on viral production. Thus, ribosomal frameshifting is a compelling, unexploited target for novel antiviral agents (Dinman, et al., 1998, *Trends Biotechnol.* 16:190-196).

Accordingly, the present invention provides compounds capable of modulating the efficiency of programmed ribosomal frameshifting, methods by which such compounds capable of modulating the efficiency of viral programmed ribosomal frameshifting may be identified or validated and methods for treating viral infections using such compounds.

SUMMARY OF THE INVENTION

The present invention relates to compounds that modulate ribosomal frameshifting and nucleic acid constructs for use in methods for identifying or validation such compounds. In particular, the present invention relates to antiviral compounds capable of modulating the efficiency of viral programmed ribosomal frameshifting, nucleic acid constructs for use in methods for identifying or validating such compounds and methods for treating viral infections using such compounds.

The invention is based, in part, on the Applicants' discovery that a cryptic splice site is created by a single base change when a guanine nucleotide is inserted after nucleic acid residue 48 of exon 7 of SMN (Survival Motor Neuron) in a nucleic acid construct comprising, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN.

The cryptic splice site results in a deletion of the last seven nucleotides of exon 7 and creates a spliced mRNA in which (i) the open reading frame defined by the first start codon on the SMN open reading frame is frameshifted relative to the open reading frame of the reporter gene and (ii) the open reading frame defined by the first start codon in the SMN open reading frame contains an aberrant stop codon upstream from the reporter gene coding sequence. Without being limited by theory, the presence of the aberrant stop codon generated by the 5' cryptic splice site, possibly, but not necessarily, in combination with a secondary structure of the downstream RNA, may cause the ribosome to pause and thus affect the efficiency of programmed ribosomal frameshifting. The Applicants have also demonstrated that a compound identified using a similar nucleic acid construct (i.e., the SMN2-linked reporter gene construct described in Zhang, et al., 2001, *Gene Therapy*, 8:1532-1538) modulates the efficiency of programmed ribosomal frameshifting. Thus, the nucleic acid constructs of the present invention may be used to identify or validate compounds that modulate the efficiency of programmed ribosomal frameshifting, and which may be of therapeutic benefit for treating viral infections.

Certain nucleic acid constructs described in the present invention for use in methods for identifying or validating compounds that modulate the efficiency of viral programmed ribosomal frameshifting have been disclosed in co-pending U.S. patent application Ser. No. 12/473,116, filed May 27, 2009.

In an aspect of the invention, the present invention provides nucleic acid constructs for use in cell-based and cell-free screening assays for the identification or validation of compounds that modulate (e.g., increases/causes or decreases) ribosomal frameshifting. In another aspect of the invention, the invention provides nucleic acid constructs for use in cell-based and cell-free screening assays for the identification or validation of compounds that modulate the efficiency of programmed ribosomal frameshifting. In one embodiment, a nucleic acid construct comprises, in 5' to 3' order: (i) a fragment of the nucleic acid residues of exon 8 of SMN; and (ii) a reporter gene coding sequence lacking a start codon, wherein the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and a stop codon is upstream of the reporter gene in the mRNA transcript. In certain embodiments, the fragment of the nucleic acid residues of exon 8 of SMN consists of the first 3, 5, 7, or 9 nucleotides from the 5' end of exon 8 of SMN. In other embodiments, the fragment of the nucleic acid residues of exon 8 of SMN consists of the first 11, 13, 15, 17, or 19 nucleotides from the 5' end of exon 8 of SMN. In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the fragment of the nucleic acid residues of exon 8 of SMN. In accordance with such embodiments, the first start codon and the stop codon upstream of the reporter gene coding sequence are in the same contiguous open reading frame without any interruption by, e.g., a stop codon.

In another embodiment, a nucleic acid construct comprises, in 5' to 3' order: (a) a fragment of the nucleic acid residues of exon 7 of SMN; (b) a fragment of the nucleic acid residues of exon 8 of SMN; and (c) a reporter gene coding sequence lacking a start codon, wherein: (i) in the mRNA transcript transcribed from the nucleic acid construct, the region of the mRNA transcript corresponding to the fragment of the nucleic acid residues of exon 7 of SMN does not contain a stop codon; (ii) the fragment of the nucleic acid residues of exon 7 of SMN comprises any number of nucleotides of exon 7 of SMN so long as in the mRNA transcript transcribed from the nucleic acid construct the open reading frames of the fragment of the nucleic acid residues of exon 7 of SMN and the fragment of the nucleic acid residues of exon 8 of SMN are in frame with each other; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another embodiment, the fragment of the nucleic acid residues of SMN consists of the first 23 nucleotides from the 5' end of exon 8 of SMN. In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon, (b) a fragment of the nucleic acid residues of exon 7 of SMN; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) the fragment of the nucleic acid residues of exon 7 of SMN comprises any number of nucleotides of exon 7 of SMN so long as in the mRNA transcript transcribed from the nucleic acid construct the first start codon and the stop codon upstream of the reporter gene coding sequence are maintained in the same contiguous open reading frame without any interruption by, e.g., stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN; (c) a fragment of the nucleic acid residues of exon 8 of SMN; and (d) a reporter gene coding sequence lacking a start codon, wherein: (i) in the mRNA transcript transcribed from the nucleic acid construct, the regions of the mRNA transcripts corresponding to the fragments of the nucleic acid residues of exon 6 and exon 7 of SMN do not contain a stop codon; (ii) the fragment of the nucleic acid residues of exon 6 of SMN and the fragment of the nucleic acid residues of exon 7 of SMN each comprise any number of nucleotides of exon 6 of SMN and exon 7 of SMN, respectively, so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with one another; (iii) the open reading frame of the nucleic acid residues of exon 6 of SMN, the open reading frame of the fragment of the nucleic acid residues of exon 7 of SMN, and the open reading frame of the nucleic acid residues of the nucleic acid residues of exon 8 of SMN are in frame with one another in the mRNA transcript from the nucleic acid construct; and (iv) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter coding sequence). In one embodiment, the fragment of the nucleic acid residues of exon 8 of SMN consists of the first 21 or 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon, (b) the nucleic acid residues of exon 6 of SMN or a fragment thereof; (c) a fragment of the nucleic acid residues of exon 7 of SMN; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter coding sequence); and (ii) the fragment of the nucleic acid residues of exon 6 of SMN and the fragment of the nucleic acid residues of exon 7 of SMN each comprise any number of nucleotides of exon 6 of SMN and exon 7 of SMN, respectively, so long as in the mRNA transcript transcribed from the nucleic acid construct the first start codon and the stop codon upstream of the reporter gene coding sequence are maintained in the same contiguous open reading frame without any interruption by, e.g., a stop codon.

In another embodiment, a nucleic acid construct comprises, in 5' to 3' order: (a) a fragment of the nucleic acid residues of exon 7 of SMN; (b) the nucleic acid residues of intron 7 of SMN or a fragment thereof, wherein the fragment of the nucleic acid residues of intron 7 comprises any number of nucleotides of intron 7 of SMN required for a functional, minimum intron; (c) a fragment of the nucleic acid residues of exon 8 of SMN; and (d) a reporter gene coding sequence lacking a start codon, wherein: (i) in the mRNA transcript transcribed from the nucleic acid construct, the region of the mRNA transcript corresponding to the fragment of the nucleic acid residues of exon 7 of SMN does not contain a stop codon; (ii) the fragment of the nucleic acid residues of exon 7 of SMN comprises a minimum of the nucleotides of exon 7 of SMN required for splicing and in the mRNA transcript transcribed from the nucleic acid construct the open reading frame of the fragment of the nucleic acid residues of exon 7 of SMN and the open reading frame of the fragment of the nucleic acid residues of exon 8 of SMN are in frame with each other; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, the fragment of the nucleic acid residues of exon 7 of SMN comprises the first two nucleotides from the 3' end of exon 7 of SMN (i.e., nucleotide residues 53 and 54 from the 5' end of exon 7 of SMN). In a specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) the fragment of the nucleic acid residues of exon 7 of SMN comprises a minimum number of the nucleotides of exon 7 of SMN required for splicing and that number of nucleotides maintains the start codon and the stop codon upstream of the reporter gene coding sequence in the same contiguous open reading frame without any interruption by, e.g., stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) in the mRNA transcript transcribed from the nucleic acid construct, the regions of the mRNA transcript corresponding to the fragments of the nucleic acid residues of exon 6 and exon 7 of SMN do not contain a stop codon; (ii) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with each other; (iii) the fragment of the nucleic acid residues of exon 7 of SMN comprises a minimum of the nucleotides of exon 7 of SMN required for splicing and in the mRNA transcript transcribed from the nucleic acid construct the open reading frame of the fragment of the nucleic acid residues of exon 7 of SMN, the open reading frame of the nucleic acid residues of exon 6 of SMN or a fragment thereof, and the open reading frame of the fragment of exon 8 of SMN are in frame with each other; and (iv) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, the fragment of the nucleic acid residues of exon 7 of SMN comprises the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 6 of SMN or a fragment thereof; (c) a fragment of the nucleic acid residues of exon 7 of SMN; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) the fragment of the nucleic acid residues of exon 6 of SMN comprises any number of nucleotides of exon 6 of SMN so long as in the mRNA transcript transcribed from the nucleic acid construct the first start codon and the stop codon upstream of the reporter gene coding sequence are maintained in the same contiguous open reading frame without any interruption by, e.g., stop codon; and (iii) the fragment of the nucleic acid residues of exon 7 of SMN comprises a minimum number of the nucleotides of exon 7 of SMN required for splicing and that number of nucleotides maintains the first start codon and the stop codon upstream of the reporter gene coding sequence in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (c) a fragment of the nucleic acid residues of exon 7 of SMN; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (1) a reporter gene coding sequence lacking a start codon, wherein: (i) in the mRNA transcript transcribed from the nucleic acid construct, the regions of the mRNA transcript corresponding to the fragments of the nucleic acid residues of exon 6 and exon 7 of SMN do not contain a stop codon; (ii) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid residues of exon 6 of SMN and the fragment of the nucleic acid residues of exon 8 of SMN are in frame with each other; (iii) the fragment of the nucleic acid residues of exon 7 of SMN comprises a minimum of the nucleotides of exon 7 of SMN required for splicing and in the mRNA transcript transcribed from the nucleic acid construct the open reading frame of the fragment of the nucleic acid residues of exon 7 of SMN, the open reading frame of the nucleic acid residues of exon 6 of SMN or a fragment thereof, and the open reading frame of the fragment of exon 8 of SMN are in frame with each other; and (iv) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain specific embodiments, the fragment of the nucleic acid residues of exon 6 of SMN comprises a minimum of the first two nucleotides from the 3' end of exon 6 of SMN. In other embodiments, the fragment of the nucleic acid residues of exon 6 of SMN comprises a minimum of the first three nucleotides from the 3' end of exon 6 of SMN. In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 6 of SMN or a fragment thereof; (c) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (d) a fragment of the nucleic acid residues of exon 7 of SMN; (e) the nucleic acid residues of intron 7 of SMN or a fragment thereof, wherein the fragment of the nucleic acid residues of intron 7 comprises any number of nucleotides of intron 7 of SMN required for a functional, minimum intron; (f) a fragment of the nucleic acid residues of exon 8 of SMN; and (g) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) the fragment of the nucleic acid residues of exon 6 of SMN and the fragment of the nucleic acid residues of exon 7 of SMN each comprise a minimum number of the nucleotides of exon 6 of SMN and exon 7 of SMN, respectively, required for splicing and that number of nucleotides maintains the first start codon and the stop codon upstream of the reporter gene coding sequence in the same contiguous open reading frame without any interruption by, e.g., a stop codon.

In another embodiment, a nucleic acid construct comprises, in 5' to 3' order: (a) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (b) a fragment of the nucleic acid residues of exon 8 of SMN; and (c) a reporter gene coding sequence lacking a start codon, wherein: (i) in the mRNA transcript transcribed from the nucleic acid construct, the open reading frame of the nucleic acid residues of exon 7 of SMN and the open reading frame of the fragment of the nucleic acid residues of exon 8 of SMN are in frame with each other; and (ii) the reporter gene coding sequence is fused to the fragment of the nucleic acid residues of exon 8 of SMN such that the open reading frames of the reporter gene and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another embodiment, the fragment of the nucleic acid residues of SMN consists of the first 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, the nucleic acid construct comprises a start codon upstream (5') to the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon, (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with one another; (ii) the open reading frame of the nucleic acid residues of exon 6 of SMN, the open reading frame of the nucleic acid residues of exon 7 of SMN, and the open reading frame of the fragment of exon 8 of SMN are in frame with one another in the mRNA transcript transcribed from the nucleic acid construct; (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (b) the nucleic acid residues of intron 7 of SMN or a fragment thereof, wherein the fragment of the nucleic acid residues of intron 7 comprises any number of nucleotides of intron 7 of SMN required for a functional, minimum intron; (c) a fragment of the nucleic acid residues of exon 8 of SMN; and (d) a reporter gene coding sequence lacking a start codon, wherein: (i) the open reading frame of the nucleic acid residues of exon 7 of SMN and the open reading frame of the nucleic acid residues of exon 8 of SMN are in frame with each other in the mRNA transcript transcribed from the nucleic acid construct; and (ii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, the nucleic acid construct comprises a start codon upstream (5') to the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the fragment of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of exon 8 of SMN are in frame with one another in the mRNA transcript transcribed from the nucleic acid construct; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (c) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid residues of exon 6 of SMN and the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of the nucleic acid residues of exon 8 of SMN are in frame with one another in the mRNA transcript transcribed from the nucleic acid construct; and (iii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, a single nucleotide residue is inserted after the 48th nucleotide residue from the 5' end of exon 7 of SMN (i.e., before the 6th nucleotide from the 3' end of exon 7 of SMN). In certain specific embodiments, the fragment of the nucleic acid residues of exon 6 of SMN comprises a minimum of the first two nucleotides from the 3' end of exon 6 of SMN. In other embodiments, the fragment of the nucleic acid residues of exon 6 of SMN comprises a minimum of the first three nucleotides from the 3' end of exon 6 of SMN. In certain embodiments, an internal start codon (e.g., ATG) of the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof, wherein the fragment comprises a minimum number of nucleotides required for splicing; (c) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (d) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (e) the nucleic acid residues of intron 7 of SMN or a fragment thereof, wherein the fragment of the nucleic acid residues of intron 7 of SMN comprises any number of nucleotides of intron 7 of SMN required for a functional, minimum intron; (f) a fragment of the nucleic acid residues of exon 8 of SMN; and (g) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (b) the nucleic acid residues of intron 7 of SMN or a fragment thereof, wherein the fragment of the nucleic acid residues of intron 7 comprises any number of nucleotides of intron 7 of SMN required for a functional, minimum intron; (c) a fragment of the nucleic acid residues of exon 8 of SMN; and (d) a reporter gene coding sequence lacking a start codon, wherein: (i) the open reading frame of the nucleic acid residues of exon 7 of SMN and the open reading frame of the fragment of the nucleic acid residues of exon 8 of SAM are in frame with each other in the mRNA transcript transcribed from the nucleic acid construct; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In another embodiment, the fragment of the nucleic acid residues of SMN consists of the first 23 nucleotides from the 5' end of exon 8 of SMN. In certain embodiments, the nucleic acid construct comprises a start codon upstream (5') to the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of intron 7 of SMN comprises any number of nucleotides of intron 7 of SMN required for a functional, minimum intron; (d) a fragment of the nucleic acid residues of exon 8 of SMN; and (e) a reporter gene coding sequence lacking a start codon, wherein (i) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (d) the nucleic acid residues of intron 7 of SMN or a fragment thereof, wherein the fragment of intron 7 of SMN comprises any number of nucleotides of intron 7 of SMN required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 required for a functional, minimum intron; (c) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (d) the nucleic acid residues of intron 7 of SMN or a fragment thereof, wherein the fragment of intron 7 of SMN comprises any number of nucleotides of intron 7 of SMN required for a functional, minimum intron; (e) a fragment of the nucleic acid residues of exon 8 of SMN; and (f) a reporter gene coding sequence lacking a start codon, wherein (i) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid residues of exon 6 of SMN and the open reading frame of the fragment of the nucleic acid residues of exon 8 of SMN are in frame with each other; (ii) the open reading frame of the nucleic acid residues of exon 6 of SMN, the open reading frame of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iv) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain specific embodiments, the fragment of the nucleic acid residues of exon 6 of SMN comprises a minimum of the first two nucleotides from the 3' end of exon 6 of SMN. In other embodiments, the fragment of the nucleic acid residues of exon 6 of SMN comprises a minimum of the first three nucleotides from the 3' end of exon 6 of SMN. In certain embodiments, an internal ATG in the nucleic acid residues of exon 6 of SMN or a fragment thereof is used as a start codon for the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) the nucleic acid residues of intron 6 of SMN or a fragment thereof, wherein the fragment of the nucleic acid residues of intron 6 of SMN comprises any number of nucleotides of intron 6 required for a functional, minimum intron; (d) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (e) the nucleic acid residues of intron 7 of SMN or a fragment thereof, wherein the fragment of intron 7 of SMN comprises any number of nucleotides of intron 7 of SMN required for a functional, minimum intron; (f) a fragment of the nucleic acid residues of exon 8 of SMN; and (g) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) a minimum of one nucleotide; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN); (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN. In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the minimum of one nucleotide. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN), wherein a single guanine residue is inserted into the fragment of the nucleic acid residues of exon 7 of SMN at the location that corresponds to the location in exon 7 of SMN that is after the 48th nucleotide from the 5' end of exon 7 of SMN, and wherein the fragment of the nucleic acid residues of exon 7 of SMN comprises any number of nucleotides of exon 7 required for splicing; (b) the nucleic acid residues of intron 7 of SMN or a fragment thereof, wherein the fragment of the nucleic acid residues of intron 7 of SMN comprises any number of nucleotides of intron 7 required for a functional, minimum intron; (c) a fragment of the nucleic acid residues of exon 8 of SMN; and (d) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN), wherein a single guanine residue is inserted into the fragment of the nucleic acid residues of exon 7 of SMN at the location that corresponds to the location in exon 7 of SMN that is after the 48th nucleotide from the 5' end of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In a specific embodiment, a nucleic acid construct comprises, in 5' to 3' order: (a) a minimum of one nucleotide; (b) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN) and wherein a single guanine residue is inserted upstream (5') of the fragment of the nucleic acid residues of exon 7 of SMN; (c) the nucleic acid residues of exon 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the minimum one nucleotide. In accordance with such embodiments, the first start codon and the stop codon upstream of the reporter gene coding sequence in the mRNA transcript are in the same contiguous open reading frame without any interruption by, e.g., a stop codon.

In a specific embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN) and wherein a single guanine residue is inserted upstream (5') of the fragment of the nucleic acid residues of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In a specific embodiment, a nucleic acid construct comprises, in 5' to 3' order: (a) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN), wherein a single guanine residue is inserted upstream (5') of the fragment of the nucleic acid residues of exon 7 of SMN, and wherein the fragment of the nucleic acid residues of exon 7 of SMN comprises any number of nucleotides of exon 7 required for splicing; (b) the nucleic acid residues of intron 7 of SMN or a fragment thereof, wherein the fragment of the nucleic acid residues of intron 7 of SMN comprises any number of nucleotides of intron 7 required for a functional, minimum intron; (c) a fragment of the nucleic acid residues of exon 8 of SMN; and (d) a reporter gene coding sequence lacking a start codon, wherein (i) in the mRNA transcript transcribed from the nucleic acid construct, open reading of the fragment of the nucleic acid residues of exon 7 of SMN and the open reading frame of the fragment of the nucleic acid residues of exon 8 of SMN are in frame with each other; (ii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iii) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, the nucleic acid construct comprises a start codon upstream (5') to the fragment of the nucleic acid residues of exon 7 of SMN. In accordance with such embodiments, the first start codon and the stop codon upstream of the reporter gene coding sequence in the mRNA transcript are in the same contiguous open reading frame without any interruption by, e.g., a stop codon.

In a specific embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN), wherein a single guanine residue is inserted upstream (5') of the fragment of the nucleic acid residues of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SAM at the location that corresponds to the location in exon 7 of SMN that is after the 48th nucleotide from the 5' end of exon 7 of SMN; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the fragment of the nucleic acid residues of exon 6 of SMN comprises any number of nucleotides of exon 6 of SMN so long as in the mRNA transcript transcribed from the nucleic acid construct the open reading frame of the fragment of the nucleic acid resides of exon 6 of SMN, the open reading frame of the fragment of the nucleic acid residues of exon 7 of SMN and the open reading frame of the fragment of the nucleic acid residues of exon 8 of SMN are in frame with each other; (ii) the open reading frame of the nucleic acid residues of exon 6 of SMN, the open reading frame of the fragment of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iv) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon; (b) the nucleic acid residues of exon 6 of SMN or a fragment thereof; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of SMN comprises any number of nucleotides of intron 6 of SMN for a functional, minimum intron; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the fragment of the nucleic acid residues of exon 6 of SMN comprises a minimum of the nucleotides of exon 6 of SMN required for splicing and in the mRNA transcript transcribed from the nucleic acid construct the open reading frame of the fragment of the nucleic acid resides of exon 6 of SMN, the open reading frame of the fragment of the nucleic acid residues of exon 7 of SMN and the open reading frame of the fragment of the nucleic acid residues of exon 8 of SMN are in frame with each other; (ii) the open reading frame of the nucleic acid residues of exon 6 of SMN, the open reading frame of the fragment of the nucleic acid residues of exon 7 of SMN, and the open reading frame of the fragment of the nucleic acid residues of exon 8 of SMN are in frame with each other in the mRNA transcript transcribed from the nucleic acid construct; (iii) the reporter gene coding sequence is fused to the fragment of the nucleic acid residues of exon 8 of SMN such that the reporter gene coding sequence and the fragment are out of frame with each other in the mRNA transcript transcribed from the nucleic acid construct; and (iv) the production of the mRNA transcript generates a stop codon in the region of the mRNA transcript that corresponds to the fragment of the nucleic acid residues of exon 8 of SMN (i.e., upstream of the reporter gene coding sequence). In a specific embodiment, the fragment of the nucleic acid residues of exon 8 of SMN consists of the first 21 or 23 nucleotides from the 5' end of exon 8 of SMN. In another specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In another specific embodiment, the fragment of exon 6 of SMN comprises a minimum of the first two nucleotides from the 3' end of exon 6 of SMN. In certain embodiments, an internal start codon (e.g., ATG) in the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) start codon; (b) the nucleic acid residues of exon 6 of SMN or a fragment thereof; (c) the nucleic acid residues of intron 6 of SMN or a fragment thereof, wherein the fragment of the nucleic acid residues of SMN comprises any number of nucleotides of intron 6 of SMN for a functional, minimum intron; (d) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (e) the nucleic acid residues of intron 7 of SMN or a fragment thereof, wherein the fragment of the nucleic acid residues of intron 7 of SMN comprises any number of nucleotides of intron 7 required for a functional, minimum intron; (f) a fragment of the nucleic acid residues of exon 8 of SMN; and (g) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon.

In certain aspects of the invention, an RNA transcript transcribed from a nucleic acid construct described above is utilized in the cell-based and cell-free screening assays to identify or validate compounds that modulate ribosomal frameshifting (e.g., programmed ribosomal frameshifting). In a specific embodiment, a mRNA transcript transcribed from a nucleic acid construct described above is utilized in the cell-based and cell-free screening assays to identify or validate compounds that modulate ribosomal frameshifting (e.g., programmed ribosomal frameshifting).

In one embodiment, the invention provides a method for the identification or validation of a compound that modulates of ribosomal frameshifting comprising: (a) contacting a compound with a host cell containing a nucleic acid construct described herein; and (b) detecting the activity or amount of a fusion protein expressed from the nucleic acid construct, wherein an increase in the activity or amount of the fusion protein expressed by the host cell in the presence of a compound when compared to (i) a previously determined reference range for a negative control, (ii) the activity or amount of the fusion protein expressed by the host cell in the absence of the compound, or (iii) the activity or amount of the fusion protein expressed by the host cell in the presence of a negative control indicates that the compound modulates ribosomal frameshifting.

In another embodiment, the invention provides a method for the identification or validation of a compound that modulates ribosomal frameshifting comprising: (a) contacting a compound with a host cell containing an RNA transcript transcribed from a nucleic acid construct described herein; and (b) detecting the activity or amount of a fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, or (iii) the activity or amount of the fusion protein translated from the RNA transcript in the presence of a negative control indicates that the compound modulates ribosomal frameshifting.

In one embodiment, the invention provides a method for the identification or validation of a compound that modulates the efficiency of programmed ribosomal frameshifting comprising: (a) contacting a compound with a host cell containing a nucleic acid construct described herein; and (b) detecting the activity or amount of a fusion protein expressed from the nucleic acid construct, wherein an increase in the activity or amount of the fusion protein expressed by the host cell in the presence of a compound when compared to (i) a previously determined reference range for a negative control, (ii) the activity or amount of the fusion protein expressed by the host cell in the absence of the compound, or (iii) the activity or amount of the fusion protein expressed by the host cell in the presence of a negative control indicates that the compound modulates the efficiency of programmed ribosomal frameshifting.

In another embodiment, the invention provides a method for the identification or validation of a compound that modulates the efficiency of programmed ribosomal frameshifting comprising: (a) contacting a compound with a host cell containing an RNA transcript transcribed from a nucleic acid construct described herein; and (b) detecting the activity or amount of a fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, or (iii) the activity or amount of the fusion protein translated from the RNA transcript in the presence of a negative control indicates that the compound modulates the efficiency of programmed ribosomal frameshifting.

In another embodiment, the invention provides a method for identifying or validating a compound that modulates ribosomal frameshifting comprising: (a) contacting a compound with a cell-free extract and an RNA transcript transcribed from a nucleic acid construct described herein; and (b) detecting the amount or activity of the fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, or (iii) the activity or amount of the fusion protein translated from the RNA transcript in the presence of a negative control indicates that the compound modulates ribosomal frameshifting.

In another embodiment, the invention provides a method for identifying or validating a compound that modulates the efficiency of programmed ribosomal frameshifting comprising: (a) contacting a compound with a cell-free extract and an RNA transcript transcribed from a nucleic acid construct described herein; and (b) detecting the amount or activity of the fusion protein translated from the RNA transcript, wherein an increase in the activity or amount of the fusion protein translated from the RNA transcript in the presence of a compound when compared to (i) a previously determined reference range for a negative control, (ii) the activity or amount of the fusion protein translated from the RNA transcript in the absence of the compound, or (iii) the activity or amount of the fusion protein translated from the RNA transcript in the presence of a negative control indicates that the compound modulates the efficiency of programmed ribosomal frameshifting.

The compounds identified or validated in the cell-based or cell-free assays may be used to modulate the efficiency of viral programmed ribosomal frameshifting and may be used to inhibit or reduce viral replication, inhibit or reduce viral infectivity, treat a viral infection, prevent a viral disease, or treat a viral disease. In one embodiment, the invention provides a method for modulating the efficiency of viral programmed ribosomal frameshifting, comprising contacting a compound with a mixture of a cell and a virus that employs ribosomal frameshifting, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for modulating the efficiency of viral programmed ribosomal frameshifting, comprising contacting a compound with a cell containing a virus or provirus that employs programmed ribosomal frameshifting, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for altering the ratio of two viral genes expressed from overlapping reading frames in which programmed ribosomal frameshifting regulates the expression of the two genes, comprising contacting a compound with a mixture of a cell and a virus that employs programmed ribosomal frameshifting, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for altering the ratio of two viral genes expressed from overlapping reading frames in which programmed ribosomal frameshifting regulates the expression of the two genes, comprising contacting a compound with a cell containing a virus or provirus that employs programmed ribosomal frameshifting, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In certain embodiments, the cells used in the cell-based assays described herein are susceptible to infection with a virus.

A compound identified or validated in the cell-based or cell-free assays that modulate the efficiency of viral programmed ribosomal frameshifting may be used as an antiviral agent. Compounds that modulate the efficiency of programmed ribosomal frameshifting have several advantages over other antiviral agents currently in use. For example, a compound that modulates the efficiency of programmed ribosomal frameshifting is expected to have limited adverse effects on cellular gene expression because it is likely that mammalian ribosomal frameshifting may be the result of cis-acting sequences and transacting factors that are different from those of viral (e.g., HIV-1) programmed −1 ribosomal frameshifting. There are only two known mammalian genes (Edr and Ma3) that are expressed by −1 ribosomal frameshifting (Shigemoto, et al., 2001, *Nucleic Acids Res.* 29:4079-4088; Wills, et al., 2006, *J. Biol. Chem.* 281:7082-7088). Edr is expressed during embryogenesis. Ma3 is a member of family of mammalian genes whose protein products are the target of immunity associated with paraneoplastic disorders. However, downstream of both Edr and Ma3 ribosomal frameshifting signals there is a pseudoknot structure (see, Shigemoto, et al., 2001, *Nucleic Acids Res.* 29:4079-4088; Wills, et al., 2006, *J. Biol. Chem.* 281:7082-7088), which is fundamentally different from that of the HIV ribosomal frameshifting stem-loop (Gaudin, et al., 2005, *J. Mol. Biol.* 349:1024-1035).

In one embodiment, the invention provides a method for reducing or inhibiting viral replication, comprising contacting a cell or a population of cells containing a virus or provirus that employs programmed ribosomal frameshifting with a compound, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for reducing or inhibiting viral replication, comprising contacting a compound with a mixture of a cell or a population of cells and a virus that employs programmed ribosomal frameshifting, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for reducing or inhibiting a viral infection, comprising contacting a cell or a population of cells containing a virus or provirus that employs programmed ribosomal frameshifting with a compound, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for reducing or inhibiting a viral infection, comprising contacting a compound with a mixture of a cell or a population of cells and a virus that employs programmed ribosomal frameshifting, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for inhibiting or reducing viral replication in a subject, comprising administering to a subject in need thereof an effective amount of a compound or a pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for reducing viral titers in a subject, comprising administering to a subject in need thereof an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for treating a viral infection in a subject, comprising administering to a subject in need thereof an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for preventing a viral disease in a subject, comprising administering to a subject in need thereof an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for treating a viral disease in a subject, comprising administering to a subject in need thereof an effective amount of a compound or pharmaceutical composition thereof, wherein the compound in vitro or in cells increases the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN. In one embodiment, the compound is a compound of Formula (I) or a form thereof. In another embodiment, the compound is a compound of Formula (II) or a form thereof. In another embodiment, the compound is a compound of Formula (Ia) or a form thereof. In another embodiment, the compound is a compound of Formula (IIa) or a form thereof. In a specific embodiment, the compound is Compound 1.

In another embodiment, the invention provides a method for inhibiting or reducing viral replication comprising contacting a cell or a population of cells containing a virus or provirus with an effective amount of a compound or a pharmaceutical composition thereof, wherein the virus employs programmed ribosomal frameshifting, and wherein the effective amount is an amount sufficient to cause a statistically significant change in viral programmed ribosomal frameshifting efficiency as measured by a technique known to one of skill in the art or as described herein, e.g., a dual luciferase construct assay. In another embodiment, the invention provides a method for inhibiting viral replication comprising contacting a cell or a population of cells containing a virus or provirus with an effective amount of a compound or a pharmaceutical composition thereof, wherein the virus employs programmed ribosomal frameshifting, and wherein the effective amount is an amount effective to alter the efficiency of programmed ribosomal frameshifting by at least 20% (and in some embodiments, at least 25%, at least 30%, at least 40%, at least 50%, or at least 75%) as measured by a technique known to one of skill in the art or described herein, e.g., a dual luciferase construct assay.

In another embodiment, the invention provides a method for inhibiting or reducing viral replication comprising contacting a mixture of a cell or a population of cells and a virus with an effective amount of a compound or a pharmaceutical composition thereof, wherein the virus employs programmed ribosomal frameshifting, and wherein the effective amount is an amount sufficient to cause a statistically significant change in viral programmed ribosomal frameshifting efficiency as measured by a technique known to one of skill in the art or as described herein, e.g., a dual luciferase construct assay. In another embodiment, the invention provides a method for inhibiting or reducing viral replication comprising contacting a mixture of a cell or a population of cells and a virus with an effective amount of a compound or a pharmaceutical composition thereof, wherein the virus employs programmed ribosomal frameshifting, and wherein the effective amount is an amount effective to alter the efficiency of programmed ribosomal frameshifting by at least 20% (and in some embodiments, at least 25%, at least 30%, at least 40%, at least 50% or at least 75%) as measured by a technique known to one of skill in the art or as described herein, e.g., a dual luciferase construct assay.

In another embodiment, the invention provides a method for inhibiting or reducing viral infectivity, comprising contacting a cell or a population of cells containing a virus or provirus with an effective amount of a compound or a pharmaceutical composition thereof, wherein the virus employs programmed ribosomal frameshifting, and wherein the effective amount is an amount sufficient to cause a statistically significant change in viral programmed ribosomal frameshifting efficiency as measured by a technique known to one of skill in the art or as described herein, e.g., a dual luciferase construct assay. In another embodiment, the invention provides a method for inhibiting or reducing viral infectivity, comprising contacting a cell or a population of cells containing a virus or provirus with an effective amount of a compound or a pharmaceutical composition thereof, wherein the virus employs programmed ribosomal frameshifting, and wherein the effective amount is an amount effective to alter the efficiency of programmed ribosomal frameshifting by at least 20% (and in some embodiments, at least 25%, at least 30%, at least 40%, at least 50% or at least 75%) as measured by a technique known to one of skill in the art or as described herein, e.g., a dual luciferase construct assay.

In another embodiment, the invention provides a method for inhibiting or reducing viral infectivity comprising contacting a mixture of a cell or a population of cells and a virus with an effective amount of a compound or a pharmaceutical composition thereof, wherein the virus employs programmed ribosomal frameshifting, and wherein the effective amount is an amount sufficient to cause a statistically significant change in viral programmed ribosomal frameshifting efficiency as measured by a technique known to one of skill in the art or as described herein, e.g., a dual luciferase construct assay. In another embodiment, the invention provides a method for inhibiting or reducing viral infectivity comprising contacting a mixture of a cell or a population of cells and a virus with an effective amount of a compound or a pharmaceutical composition thereof, wherein the virus employs programmed ribosomal frameshifting, and wherein the effective amount is an amount effective to alter the efficiency of programmed ribosomal frameshifting by at least 20% (and in some embodiments, at least 25%, at least 30%, at least 40%, at least 50% or at least 75%) as measured by a technique known to one of skill in the art or as described herein, e.g., a dual luciferase construct assay.

In another embodiment, the invention provides a method for preventing or treating a viral disease in a subject, comprising administering to a subject in need thereof an effective amount of a compound or a pharmaceutical composition thereof, wherein the viral disease is a pathological condition resulting from the presence of a virus, and wherein the effective amount is an amount effective to sufficient to cause a statistically significant change in viral programmed ribosomal frameshifting as measured by a technique known to one of skill in the art or as described herein, e.g., a dual luciferase construct assay. In another embodiment, the invention provides a method for preventing or treating a viral disease in a subject, comprising administering to a subject in need thereof an effective amount of a compound or a pharmaceutical composition thereof, wherein the viral disease is a pathological condition resulting from the presence of a virus, and wherein the effective amount is an amount effective to alter the efficiency of programmed ribosomal frameshifting by at least 20% (and in some embodiments, at least 25%, at least 30%, at least 40%, at least 50%, or at least 75%) as measured by a technique known to one of skill in the art or as described herein, e.g., a dual luciferase construct assay.

In certain embodiments, a compound identified or validated by a method described herein modulates the efficiency of programmed −1 ribosomal frameshifting. In certain embodiments, a compound identified or validated by a method described herein modulates the efficiency of programmed +2 ribosomal frameshifting.

Non-limiting examples of viruses that employ programmed ribosomal frameshifting include the viruses listed in Table 1, infra, which is a modified version of Table 1 in Brierley, 1995, *J. Gen. Virol.* 76:1885-1892. In a specific embodiment, the virus is not a human immunodeficiency virus, hepatitis virus, or human papillomavirus.

TABLE 1

Occurrence of established ribosomal frameshift signals in viral RNAs

| Family/Group | Genus | Virus | Gene or Gene overlap |
|---|---|---|---|
| Retroviridae | Lentivirus | Human immunodeficiency virus type 1 (HIV-1) | gag-pol |
| | | Feline immunodeficiency virus (HIV) | gag-pol |
| | ALSV | Rous sarcoma virus (RSV) | gag-pol |
| | B-type | Mouse mammary tumour virus (MMTV) | gag-pro |
| | D-type | Simian retrovirus type 1 (SRV-1) | gag-pro |
| | HTLV/BLV | Human T cell leukaemia virus type I (HTLV-I) | gag-pro |
| | | HTLV-I | pro-pol |
| | | HTLV-II | gag-pro-pol |
| Coronaviridae | Coronavirus | Infectious bronchitis virus (IBV) | orf1a-orf1b |
| | | Mouse hepatitis virus (MHV) | orf1a-orf1b |
| | | Human coronavirus (HCoV) | orf1a-orf1b |
| | | severe acute respiratory syndrome coronavirus (SARS-CoV) | orf3a |
| | | Transmissible gastroenteritis virus (TGEV) | orf1a-orf1b |
| | Torovirus | Berne virus (BEV) | orf1a-orf1b |
| | Arterivirus | Equine arteritis virus (EAV) | orf1a-orf1b |
| Astroviridae | Astrovirus | Human astrovirus serotype-1 (HAst-1) | orf1a-orf1b |
| Totiviridae | Totivirus | Giardia lamblia virus (GLV) | orf1-orf2 |
| | | Saccharomyces cerevisiae dsRNA virus L-A (ScV/L-A) | gag-pol |
| | | S. cerevisiae dsRNA virus L1 (ScV/L1) | cap-pol |
| Podoviridae | T7 phage | Bacteriophage T7 | 10A-10B |
| Siphoviridae | λ phage group | Bacteriophage λ | gpG-T |
| Luteoviridae | Luteovirus | Barley yellow dwarf virus (BYDV) | 39K-60K |
| | | Beet western yellows virus (BWYV) | orf2-orf3 |
| | | Potato leaf roll virus (PLRV) | orf2a-orf2b |
| Dianthoviridae | Dianthovirus | Red clover necrotic mosaic virus (RCNMV) | p27-p57 |
| Herpesviridae | Simplexvirus | Herpes Simplex Virus (HSV) | thymidine kinase gene |

While not being limited by theory, within the scope of the invention is the identification or validation of compounds that modulate viral programmed ribosomal frameshifting such that an attenuated virus or viral particle is produced. In a specific embodiment, the attenuated virus or viral particle may be used as a vaccine.

TERMINOLOGY

As used herein, the term "about" or "approximately," when used in conjunction with a number, refers to any number within 1, 5 or 10% of the referenced number.

As used herein, the terms "increase," "increases," and "increased," in the context of the amount or activity of a fusion protein refer, in some embodiments, to: (i) an increase of 0.5%, 1%, 1.5%, 2%, 5%, 10%, 20%, 30%, 40%, 50% or more; (ii) an increase of 1.5, 2, 3, 4, or 5 fold or more; or (iii) a statistically significant increase in the amount or activity of the fusion protein relative to a negative control.

As used herein, the terms "change" or "changed," in the context of the efficiency of programmed ribosomal frameshifting refer, in some embodiments, to: (i) a change of 0.5%, 1%, 1.5%, 2%, 5%, 10%, 20%, 30%, 40%, 50% or more; (ii) a change of 1.5, 2, 3, 4, or 5 fold or more; or (iii) a statistically significant change in the efficiency of programmed ribosomal frameshifting.

As used herein, the term "not changed" refers to no detectable change or no statistically significant change (i.e., a change that has a p value of greater than 0.1).

As used herein, the term "statistically significant increase" refers to an increase that has a p value of less than 0.1, 0.05, 0.01, 0.05, or 0.01.

As used herein, the term "not statistically significant increase" refers to an increase that has a p value of more than 0.001, 0.01, 0.05, or 0.1.

As used herein, the term "statistically significantly change" refers to a change that has a p value of less than 0.1, 0.05, 0.01, 0.05, or 0.01.

As used herein, unless otherwise specified, the term "programmed ribosomal frameshifting" refers to a process in which either a structural or sequence element directs the ribosomal machinery to shift translational reading frame.

As used herein, the term "compound," unless otherwise specified or clear from the context of the specification, refers to any agent being tested for its ability to modulate the efficiency of programmed ribosomal frameshifting, or is identified or validated as modulating the efficiency of programmed ribosomal frameshifting using a nucleic acid construct described herein. In one embodiment, the term "compound" refers to a small molecule. In a specific embodiment, the term "compound" refers to a compound of Formula (I) or Formula (II) or a form thereof. In one embodiment, the term "compound" refers to a compound selected from Compound 1.

As used herein, the term "small molecule" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) and forms thereof having a molecular weight of less than about 10,000 grams per mole, or less than about 5,000 grams per mole, or less than about 1,000 grams per mole, or less than about 500 grams per mole, or less than about 100 grams per mole.

As used herein, the term "viral disease" refers to a pathological condition resulting from the presence of a virus in a subject.

As used herein, the term "effective amount" in the context of administering a compound to a subject refers to the amount of a compound which is sufficient to achieve a prophylactic and/or therapeutic effect. In specific embodiments, the term "effective amount" in the context of administering a compound to a subject refers to the amount of a compound which is sufficient to achieve at least one of the following effects: (i) reduce or ameliorate the severity of a viral infection or disease or a symptom associated therewith; (ii) reduce the duration of a viral infection or disease or a symptom associated therewith; (iii) prevent the progression of a viral infection or a disease or a symptom associated therewith; (iv) cause regression of a viral infection or a symptom associated therewith; (v) prevent the development or onset of a viral infection or disease or a symptom associated therewith; (vi) prevent the recurrence of a viral infection or disease or a symptom associated therewith; (vii) reduce or prevent the spread of a virus from one cell to another cell, or from one tissue to another tissue; (viii) reduce or inhibit viral infectivity; (ix) prevent or reduce the spread of a virus from one subject to another subject; (x) reduce organ damage or failure associated with a viral infection or a disease associated therewith; (xi) reduce hospitalization of a subject; (xii) reduce hospitalization length; (xiii) increase the survival of a subject with a viral infection or a disease associated therewith; (xiv) reduce the viral titer in a subject having a viral infection or a disease associated therewith; (xv) eliminate a viral infection or a symptom associated therewith; (xvi) inhibit or reduce viral replication; (xvii) eliminate viral infectivity; (xviii) inhibit or reduce viral pathogenicity; (xix) cure a viral infection or disease associated therewith; and/or (xx) enhance or improve the prophylactic or therapeutic effect(s) of another agent.

As used herein, the term "effective amount" in the context of a compound for use in cell culture-related products refers to an amount of a compound which is sufficient to reduce the viral titer in cells, reduce the replication of a virus in cells or reduce the infectivity of a virus in cells.

As used herein, the term "in combination," in the context of the administration of a compound, refers to the administration of two or more compounds of the present invention that modulate the efficiency of programmed ribosomal frameshifting, or the administration of one or more compounds of the present invention that modulate the efficiency of programmed ribosomal frameshifting and one or more additional agents. The use of the term "in combination" does not restrict the order in which two or more of the instant compounds or one or more of said compounds and another agent are administered to a subject in need thereof. For example, a compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of another agent to a subject with a viral infection.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human toddler" refers to a human that is 1 year to 3 years old.

As used herein, the term "human infant" refers to a newborn to 1 year old year human.

As used herein, the term "premature human infant" refers to a human infant born at less than 37 weeks of gestational age.

As used herein, the term "combination product" refers to a product comprising: (i) two or more of the instant compounds that modulate programmed ribosomal frameshifting; or (ii) one or more of the instant compounds that modulate programmed ribosomal frameshifting and one or more additional agents.

As used herein, the term "form" in the context of a compound refers to a compound isolated for use as a pharmaceutically acceptable salt, ester, hydrate, solvate, clathrate, polymorph, geometric isomer, racemate, enantiomer, diastereomer or tautomer.

As used herein, the italicized term "SMN," unless otherwise specified herein, refers to human SMN1 or human SMN2. Nucleic acid sequences for the human SMN1 and SMN2 are known in the art. See, e.g., GENBANK® Accession Nos. DQ894095, NM_000344, NM_022874, and BC062723 for nucleic acid sequences of human SMN1. For nucleic acid sequences of human SMN2, see, e.g., NM_022875, NM_022876, NM_022877, NM_017411, DQ894734 (Invitrogen, Carlsbad, Calif.), BC000908.2, and BC015308.1.

The SMN1 gene can be found on human chromosome 5 from approximately nucleotide 70,256,524 to approximately nucleotide 70,284,595 using Vega Gene ID: OTTHUMG00000099361 (see website for ensembl.org/Homo_sapiens/geneview?gene=OTTHUMG00000099361; db=vega) at cytogenetics location 5 of 13. See also GENBANK® Accession No. NC 000005, Build 36.3 for the sequence of human chromosome 5.

The approximate locations of exons 6, 7 and 8 and introns 6 and 7 of SMN1 on human chromosome 5 using Vega gene ID: OTTHUMG00000099361 (see website for ensembl.org/Homo_sapiens/geneview?gene=OTTHUMG00000099361; db=vega) are as follows:
   70,277,649-70,277,759 exon 6
   70,277,760-70,283,523 intron 6
   70,283,524-70,283,577 exon 7
   70,283,578-70,284,021 intron 7
   70,284,022-70,284,595 exon 8

In specific embodiments, the nucleotide sequences delineated above for exons 6, 7 and 8 and introns 6 and 7 of SMN1 are used in the nucleic acid constructs described herein. In other specific embodiments, the nucleotide sequences described in the example below for exons 6, 7 and 8 and introns 6 and 7 are used in the nucleic acid constructs described herein.

The SMN2 gene can be found on human chromosome 5 from approximately nucleotide 69,381,106 to approximately nucleotide 69,409,175 using Vega gene ID: OTTHUMG00000099389 (see website for ensembl.org/Homo_sapiens/geneview?gene=OTTHUMG00000099389; db=vega). See also, GENBANK® Accession No. NC 000005, Build 36.3 for the sequence of human chromosome 5.

The approximate locations of exons 6, 7 and 8 and introns 6 and 7 of SMN2 on human chromosome 5 using Vega gene ID: OTTHUMG00000099389 (see website for ensembl.org/Homo_sapiens/geneview?gene=OTTHUMG00000099389; db=vega) are as follows:
   69,402,224-69,402,334 exon 6
   69,402,335-69,408,103 intron 6
   69,408,104-69,408,157 exon 7
   69,408,158-69,408,601 intron 7
   69,408,602-69,409,175 exon 8.

In specific embodiments, the nucleotide sequences delineated above for exons 6, 7 and 8 and introns 6 and 7 of SMN2 are used in the nucleic acid constructs described herein. In other specific embodiments, the nucleotide sequences of exons 6, 7 and 8 and introns 6 and 7 of SMN2 are used in the nucleic acid constructs described herein.

As used herein, the terms "virus," "viral," and analogous terms refer to a virus that employs programmed ribosomal frameshifting. In certain embodiments, the compounds identified and validated using the assays of the present invention are expected to be useful in modulating viral programmed ribosomal frameshifting. In a specific embodiment the viral programmed ribosomal frameshifting is −1 programmed ribosomal frameshifting. In other embodiments, the programmed ribosomal frameshifting is selected from +2 programmed ribosomal frameshifting, +1 programmed ribosomal frameshifting and −2 programmed ribosomal frameshifting.

As used herein, the term "provirus" refers to a provirus that encodes or codes for a virus that employs programmed ribosomal frameshifting.

As used herein, the term "host cell" includes a particular subject cell transformed or transfected with an instant nucleic acid construct and the progeny or potential progeny of such a cell. Progeny of such a cell may not be identical to the parent cell transfected with the nucleic acid construct due to mutations or environmental influences that may occur in succeeding generations or integration of the nucleic acid construct into the host cell genome.

As used herein, the term "isolated," as it refers to a compound, means the physical state of a compound after being separated and/or purified from precursors and other substances found in a synthetic process (e.g., from a reaction mixture) or natural source or combination thereof according to a process or processes described herein or which are well known to the skilled artisan (e.g., chromatography, recrystallization and the like) in sufficient purity to be capable of characterization by standard analytical techniques described herein or well known to the skilled artisan. In a specific embodiment, the compound is at least 60% pure, at least 65% pure, at least 70% pure, at least 75% pure, at least 80% pure, at least 85% pure, at least 90% pure or at least 99% pure as assessed by techniques known to one of skill in the art.

As used herein, the term "isolated," as it refers to a nucleic acid, means the physical state of a nucleic acid after being separated and/or purified from precursors and other substances found in a synthetic process (e.g., from a reaction mixture) or natural source or combination thereof according to a process or processes described herein or which are well known to the skilled artisan in sufficient purity to be capable of characterization by standard analytical techniques described herein or well known to the skilled artisan.

In some embodiments, the term "fragment" refers to a nucleotide sequence comprising 2, 3, 6, 9, 12, 15, 21, 24, 27, 30 or more nucleotides from a longer nucleotide sequence. In certain embodiments, the nucleotide sequences comprises 2, 3, 6, 9, 12, 15, 21, 24, 27, 30 or more contiguous nucleotides from a longer nucleotide sequence.

In some embodiments, the terms "nucleic acid" and "nucleotides" refer to deoxyribonucleotides, deoxyribonucleic acids, ribonucleotides, and ribonucleic acids, and polymeric forms thereof, and includes either single- or double-stranded forms. In certain embodiments, such terms include known analogues of natural nucleotides, for example, peptide nucleic acids ("PNA"s), that have similar binding properties as the reference nucleic acid. In some embodiments, nucleic acid refers to deoxyribonucleic acids (e.g., cDNA or DNA). In other embodiments, nucleic acid refers to ribonucleic acids (e.g., mRNA or pre-mRNA).

As used herein, the term "nucleic acid residues of exon 6 of SMN," unless otherwise specified herein, refers to a complete, intact, non-truncated nucleic acid sequence exon 6 of SMN1 or SMN2. In certain embodiments, a nucleic acid construct described herein comprises, in part, a complete, intact, non-truncated nucleic acid sequence of exon 6 of SMN1 or SMN2.

As used herein, the term "nucleic acid residues of intron 6 of SMN," unless otherwise specified herein, refers to a complete, intact, non-truncated nucleic acid sequence of intron 6 of SMN1 or SMN2. In certain embodiments, a nucleic acid construct described herein comprises, in part, a complete, intact, non-truncated nucleic acid sequence of intron 6 of SMN1 or SMN2.

As used herein, the term "nucleic acid residues of exon 7 of SMN," unless otherwise specified herein, refers to a complete, intact, non-truncated nucleic acid sequence of exon 7 of SMN1 or SMN2. In certain embodiments, a nucleic acid construct described herein comprises, in part, a complete, intact, non-truncated nucleic acid sequence of exon 7 of SMN1 or SMN2.

As used herein, the term "nucleic acid residues of intron 7 of SMN," unless otherwise specified herein, refers to a complete, intact, non-truncated nucleic acid sequence of intron 7 of SMN1 or SMN2. In certain embodiments, a nucleic acid construct described herein comprises, in part, a complete, intact, non-truncated nucleic acid sequence of intron 7 of SMN1 or SMN2.

As used herein, the term "nucleic acid residues of exon 8 of SMN," unless otherwise specified herein, refers to a complete, intact, non-truncated nucleic acid sequence of exon 8 of SMN1 or SMN2.

As used herein, the term "ORF" refers to a mRNA open reading frame, i.e., the region of the mRNA that can translated into protein.

Reference to the term "open reading frame" in the context of two or more open reading frames being in frame with each other refers to two nucleic acid sequences (e.g., nucleic acid residues of an exon(s) of SMN or a fragment thereof and/or a nucleotide sequence encoding an amino acid sequence), wherein each of the two or more nucleic acid sequences are in the same contiguous open reading frame which is defined by the first start codon and an aberrant stop codon, i.e., the stop codon upstream (5') of the reporter gene coding sequence.

Reference to the term "open reading frame" in the context of two or more open reading frames being out of frame with each other refers to two nucleic acid sequences (e.g., nucleic acid residues of an exon(s) of SMN or a fragment thereof and/or a reporter gene coding sequence), wherein each of the two or more nucleic acid sequences are not in the same contiguous open reading frame which is defined by the first start codon and an aberrant stop codon, i.e., the stop codon upstream (5') of the reporter gene coding sequence.

As used herein, the term "previously determined reference range" in the context of detecting the amount or activity of a protein refers to a reference range for the amount or the activity of a fusion protein encoded by a nucleic acid construct or transcribed from a mRNA transcript. Ideally, testing laboratories will establish a reference range for each cell type and each cell-free extract in the practice of such assays. In a specific embodiment, at least one positive control or at least one negative control is included for each compound analyzed. In a specific embodiment, the previously determined reference range is the amount or activity of a fusion protein detected in the presence of a negative control, such as phosphate-buffered saline ("PBS") or dimethyl sulfoxide ("DMSO").

As used herein, the terms "subject" and "patient" are used interchangeably, and refer to an animal (e.g., birds, reptiles, and mammals), such as a mammal including a non-primate (e.g., a camel, donkey, zebra, cow, pig, horse, goat, sheep, cat, dog, rat, and mouse) and a primate (e.g., a monkey, chimpanzee, and a human). In a specific embodiment, the subject is a human.

As used herein, the term "infection" means the invasion by a virus, the multiplication of a virus and/or presence of a virus or provirus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. In another embodiment, an infection is a latent infection, i.e., one in which the virus is not actively replicating in a cell or a subject but has the potential to replicate or one in which viral particles are present in the cell or subject without the ability to replicate. In another embodiment, an infection is a "persistent" infection, i.e., one in which the virus is not cleared but remains in cells or a subject. A persistent infection may involve stages of both silent and productive infection without rapidly killing or even producing excessive damage of cells. In a specific embodiment, an infection refers to the pathological state resulting from the presence of the virus in a cell or a subject, or by the invasion of a cell or subject by the virus.

As used herein, the term "infectivity" means the ability of a virus or viral particles to establish an infection.

As used herein, the terms "prevent," "preventing," and "prevention," in the context of the administration of a compound of the present invention either alone or in combination with another agent to a subject in need thereof to prevent a viral disease (i.e., a pathological condition resulting from the presence of a virus or provirus in a subject), refer to the inhibition of the development or onset of a viral disease or the inhibition of the recurrence of a viral disease.

As used herein, the terms "treat," "treatment," and "treating" refer, in the context of the administration of a compound alone or in combination with another agent to a subject to treat a viral infection or a viral disease, to a therapeutic benefit achieved. In a specific embodiment, such terms refer to at least one or more of the following effects resulting from the administration of a compound or other agent to a subject: (i) the reduction or amelioration of the severity of a viral infection or disease or a symptom associated therewith; (ii) the reduction in the duration of a viral infection or disease or a symptom associated therewith; (iii) the regression of a viral infection or a symptom associated therewith; (iv) the prevention of the development, onset or recurrence of a symptom associated with a viral infection or disease associated therewith; (v) the reduction of the titer of a virus; (vi) the reduction in organ damage or failure associated with a viral infection or disease associated therewith; (vii) the reduction in hospitalization of a subject; (viii) the reduction in hospitalization length; (ix) the increase in the survival of a subject with a viral infection or disease associated therewith; (x) the elimination of viral infectivity; (xi) the elimination of a viral infection or a symptom associated therewith; (xii) the inhibition of the progression of a viral infection or disease or a symptom associated therewith; (xiii) the prevention or reduction in the spread of a virus from a cell, tissue or subject to another cell, tissue or subject; (xiv) the inhibition or reduction in viral pathogenicity; (xv) the cure of a viral infection or disease associated therewith; and/or (xvi) the enhancement or improvement the therapeutic effect of another agent. In some embodiments, treatment does not refer to a cure for a viral infection or disease associated therewith, but the inhibition of the progression or worsening of the viral infection or disease associated therewith.

BRIEF DESCRIPTION OF THE DRAWINGS

FIG. 2: DNA sequence of the minigene from the SMN2-G minigene construct (SEQ ID NO:11). Within the sequence shown in FIG. 2, the following subsequences can be found:

Figure 1:
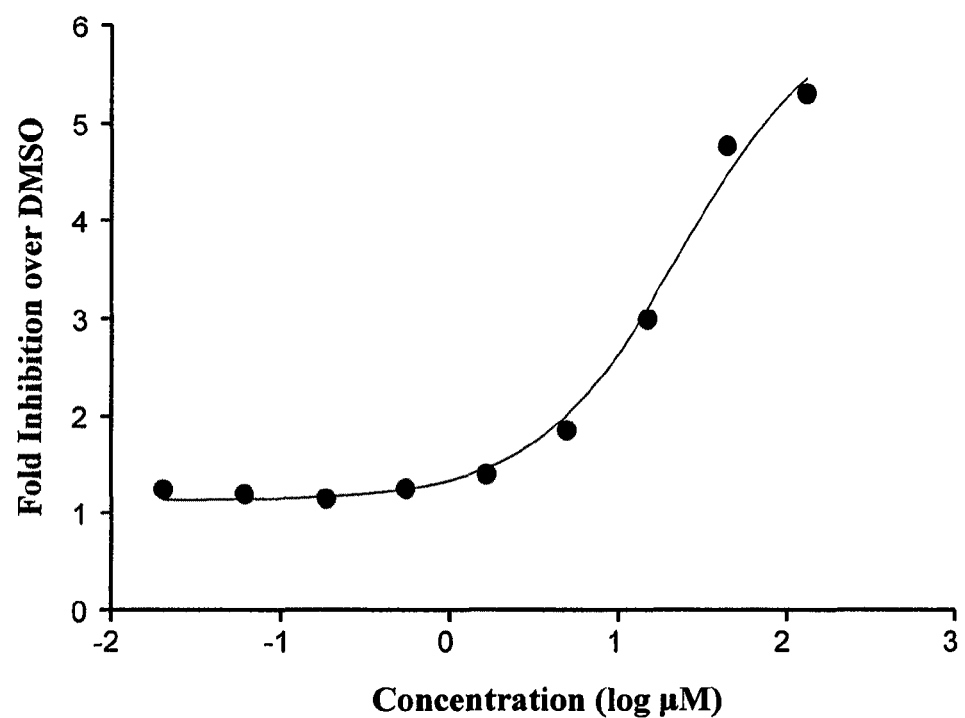
FIG. 1: Fold inhibition of luciferase activity in the presence of Compound 1.

1-70: 5'UTR (deg)
71-79: start codon and BamHI site (atgggatcc)
80-190: exon 6
191-5959: intron 6
5960-6014: exon 7 with G insert (position 6008)
6015-6458: intron 7
6459-6481: part of exon 8
6482-8146: BamHI site, luciferase coding sequence starting with codon 2, NotI site, TAA stop codon
8147-8266: 3'UTR (deg). (A) nucleic acids 1-4009 of the DNA sequence; (B) nucleic acids 4010-7885 of the DNA sequence; (C) nucleic acids 7886-8266 of the DNA sequence.

DETAILED DESCRIPTION OF THE INVENTION

The present invention relates to compounds that modulate ribosomal frameshifting and nucleic acid constructs for use in methods for identifying or validation such compounds. In particular, the present invention provides nucleic acid constructs and screening assays for the identification and validation of compounds that are capable of modulating the efficiency of programmed ribosomal frameshifting. Compounds identified or validated according to the methods of the invention are expected to be useful in the treatment of viral infections, as well as the treatment and possibly the prevention of viral disease.

In one aspect, the invention provides a method for identifying or validating a compound that modulates the efficiency of ribosomal frameshifting. In another aspect, the invention provides a method for identifying or validating a compound that modulates the efficiency of programmed ribosomal frameshifting. In another aspect, the invention provides compounds that modulate the efficiency of programmed ribosomal frameshifting, and which may be used to treat a viral infection, or prevent or treat a viral disease. In one embodiment, a compound of Formula (I) or a form thereof is used to treat a viral infection, or prevent or treat a viral disease. In another embodiment, a compound of Formula (II) or a form thereof is used to treat a viral infection, or prevent or treat a viral disease. In another embodiment, a compound of Formula (Ia) or a form thereof is used to treat a viral infection, or prevent or treat a viral disease. In another embodiment, a compound of Formula (IIa) or a form thereof is used to treat a viral infection, or prevent or treat a viral disease. In a specific embodiment, Compound I is used to treat a viral infection, or prevent or treat a viral disease.

Compounds

The compounds described in International Publication WO2007/109211 (which is incorporated by reference in its entirety) may be used in accordance with the methods described herein.

Embodiments of the present invention include uses of compounds of Formula (I) or a form thereof or Formula (II) or a form thereof, wherein Formula (I) and Formula (II) have the following structures:

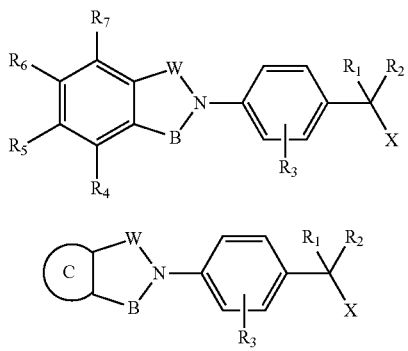

Formula (I)

Formula (II)

wherein,

W is selected from the group consisting of C(O), C(S), and CH$_2$;

B is CH$_2$ or CH(CH$_n$H$_{2n+1}$), wherein n is an integer from 1 to 8;

Ring C is selected from the group consisting of a fused thienyl ring, a fused pyridinyl ring, and a fused cyclohexyl ring, any of which can be saturated or contain, one or two non-conjugated double bonds;

R$_1$ and R$_2$ are independently selected from the group consisting of H and C$_1$-C$_3$ alkyl, or R$_1$ and R$_2$ may be taken together with the carbon atom to which they are attached to form a C$_3$-C$_6$ cycloalkyl ring or a carbonyl group;

R$_3$ is selected from the group consisting of H, halogen, C$_1$-C$_4$ alkyl, C$_1$-C$_4$ alkoxy, C$_1$-C$_4$ haloalkyl, CN, NO$_2$, heteroaryl, and phenyl optionally substituted with any combination of one to five halogen, NO$_2$, CN, C$_1$-C$_4$ alkyl, C$_1$-C$_4$ haloalkyl, or C$_1$-C$_4$ alkoxy substituents;

R$_4$, R$_5$, R$_6$ and R$_7$ are independently selected from the group consisting of H, hydroxyl, halogen, CN, NO$_2$, sulfonamide, C$_1$-C$_8$ alkyl, C$_3$-C$_6$ cycloalkyl, cycloalkyloxy, C$_1$-C$_6$ alkoxy, C$_1$-C$_6$ haloalkoxy, C$_1$-C$_4$ haloalkyl, C$_2$-C$_8$ alkenyl, amino, C$_1$-C$_4$ alkylamino, C$_1$-C$_4$ dialkylamino, C$_3$-C$_6$ cycloalkylamino, morpholinyl, heteroaryl, arylamino, arylalkylamino, phenyl, C(O)R', NR'(COR''), NR'SO$_2$R'' and NR'(CONR''R'''), wherein R', R'' and R''' are independently H, C$_1$-C$_6$ alkyl, phenyl, or substituted phenyl, and wherein C$_1$-C$_8$ alkyl is optionally substituted with one or more substituents selected from the group consisting of C$_1$-C$_4$ alkoxy, C$_1$-C$_4$ haloalkyl, C$_1$-C$_6$ dialkylamino, C$_1$-C$_6$ alkylamino, cycloalkylamino, and morpholinyl, and the phenyl is optionally substituted with one or more substituents selected from the group consisting of halogen, NO$_2$, CN, C$_1$-C$_4$ alkyl, C$_1$-C$_4$ haloalkyl, and C$_1$-C$_4$ alkoxy, or R$_4$ and R$_5$, R$_5$ and R$_6$, or R$_6$ and R$_7$, taken together with the carbon to which they are attached, form a ring;

X is selected from the group consisting of H; CN; C(O)OR$_8$, wherein R$_8$ is H or C$_1$-C$_8$ alkyl, and C$_1$-C$_8$ alkyl optionally is substituted with one or more substituents selected from the group consisting of C$_1$-C$_4$ alkoxy, C$_1$-C$_4$ haloalkyl, C$_1$-C$_6$ dialkylamino, C$_1$-C$_6$ alkylamino, cycloalkylamino, phenyl, and morpholinyl; C(O)NR$_9$R$_{10}$ or CH$_2$NR$_9$R$_{10}$, wherein R$_9$ and R$_{10}$ are independently selected from the group consisting of H and C$_1$-C$_6$ alkyl, or R$_9$ and R$_{10}$ together with the nitrogen to which they are attached form a heterocyclyl ring; CH$_2$OR$_{11}$, wherein R$_{11}$ is H, C$_1$-C$_8$ alkyl, or C$_3$-C$_6$ cycloalkyl, wherein C$_1$-C$_8$ alkyl is optionally substituted with one or more substituents selected from the group consisting of C$_1$-C$_4$ alkoxy, C$_1$-C$_4$ haloalkyl, C$_1$-C$_6$ dialkylamino, C$_1$-C$_6$ alkylamino, cycloalkylamino, and morpholinyl; CH$_2$Z, wherein Z is halogen; C(O)NHOH; C(O)NHCN; C(O)N(R$_1$)SO$_2$R$_{13}$, wherein R$_{13}$ is C$_1$-C$_4$ alkyl, phenyl, or substituted phenyl; C$_1$-C$_8$ alkyl, optionally substituted with one or more substituents selected from the group consisting of C$_1$-C$_4$ alkoxy, C$_1$-C$_4$ haloalkyl, C$_1$-C$_6$ dialkylamino, and C$_1$-C$_6$ alkylamino; and C$_2$-C$_8$ alkenyl, optionally substituted with one or more substituents selected from the group consisting of C$_1$-C$_4$ alkoxy, C$_1$-C$_4$ haloalkyl, C$_1$-C$_6$ dialkylamino, and C$_1$-C$_6$ alkylamino.

In certain embodiments, the present invention includes the use of compounds of Formula (Ia) or a form thereof or Formula (IIa) or a form thereof, wherein Formula (Ia) and Formula (IIa) have the following structures:

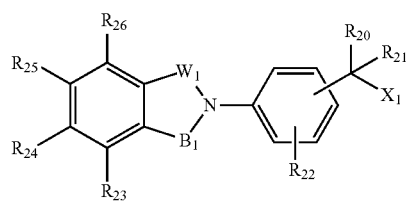

Formula (Ia)

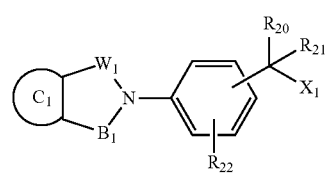

Formula (IIa)

wherein,

W$_1$ is selected from the group consisting of C(O), C(S), and CH$_2$;

B$_1$ is CH$_2$ or CH(C$_m$H$_{2m+1}$), wherein m is an integer from 1 to 8;

Ring C$_1$ is selected from the group consisting of a thienyl ring, a pyridinyl ring, a cyclohexyl ring, a benzo[d][1,3]dioxolyl ring and a 2,3-dihydrobenzo[b][1,4]dioxinyl ring, each of said rings fused to the moiety of Formula (IIa), wherein benzo[d][1,3]dioxolyl and 2,3-dihydrobenzo[b][1,4]dioxinyl, each having a benzo ring portion, are fused via said benzoportion, and wherein any of the foregoing rings may optionally be fully or partially saturated;

R$_{20}$ and R$_{21}$ are independently selected from the group consisting of H and C$_1$-C$_3$ alkyl, or R$_{20}$ and R$_{21}$ may be taken together with the carbon atom to which they are attached to form a C$_3$-C$_6$ cycloalkyl ring or a carbonyl group;

R$_{22}$ is selected from the group consisting of H, halogen, C$_1$-C$_4$ alkyl, C$_1$-C$_4$ alkoxy, C$_1$-C$_4$ haloalkyl, cyano, nitro, heteroaryl, and phenyl optionally substituted with any combination of one to five halogen, nitro, cyano, C$_1$-C$_4$ alkyl, C$_1$-C$_4$ haloalkyl or C$_1$-C$_4$ alkoxy substituents;

R$_{23}$, R$_{24}$, R$_{25}$ and R$_{26}$ are independently selected from the group consisting of H, hydroxyl, halogen, cyano, nitro, sulfonamide, C$_1$-C$_8$ alkyl, C$_1$-C$_6$ alkoxy, C$_1$-C$_6$ alkoxyalkoxy, C$_1$-C$_6$ alkoxyalkyl, C$_1$-C$_6$ haloalkoxy, C$_1$-C$_4$ haloalkyl, C$_2$-C$_6$ alkenyl, C$_2$-C$_4$ haloalkenyl, formyl, C$_1$-C$_6$ alkylcarbonyl, amino, C$_1$-C$_4$ alkylamino, C$_1$-C$_4$ dialkylamino, C$_1$-C$_4$ aminoalkyl, C$_1$-C$_4$ alkylaminoalkyl, C$_1$-C$_4$ dialkylaminoalkyl, phenyl, C$_3$-C$_6$ cycloalkyl, C$_3$-C$_6$ cycloalkylalkyl, C$_3$-C$_6$ cycloalkylalkoxy, cycloalkyloxy, heterocyclyl, heterocyclylalkyl, heteroaryl, and phenylcarbonyl, wherein amino is optionally disubstituted with one substituent selected from hydrogen, C$_1$-C$_6$ alkyl or phenyl and the other is selected from formyl, phenyl, C$_3$-C$_6$ cycloalkyl, $C_1$-$C_6$ alkylcarbonyl, aminocarbonyl, $C_1$-$C_6$ alkylaminocarbonyl, $C_1$-$C_6$ dialkylaminocarbonyl, phenylcarbonyl, phenylaminocarbonyl, N-phenyl-N—$C_1$-$C_6$ alkyl-aminocarbonyl, $C_1$-$C_6$ alkylsulfonyl, aminosulfonyl, $C_1$-$C_6$ alkylaminosulfonyl, $C_1$-$C_6$ dialkylaminosulfonyl or phenylsulfonyl, wherein each instance of $C_1$-$C_6$ alkylcarbonyl is optionally substituted on the alkyl portion with one or more substituents selected from the group consisting of halogen, $C_1$-$C_4$ alkoxy, $C_1$-$C_6$ alkylamino, $C_1$-$C_6$ dialkylamino, cycloalkylamino and heterocyclyl, wherein each instance of phenyl is optionally substituted with one or more substituents selected from the group consisting of halogen, nitro, cyano, $C_1$-$C_4$ alkyl, $C_1$-$C_4$ haloalkyl and $C_1$-$C_4$ alkoxy, and alternatively, $R_{23}$ and $R_{24}$, $R_{24}$ and $R_{25}$ or $R_{25}$ and $R_{26}$ may be taken together with the carbon to which they are attached to form a $C_3$-$C_6$ cycloalkyl ring fused to the moiety of Formula (Ia);

$X_1$ is absent or is selected from the group consisting of H, cyano, $C_1$-$C_8$ alkyl, $C_1$-$C_4$ alkoxy, amino, $C_1$-$C_4$ alkylamino, $C_1$-$C_4$ dialkylamino, carboxy, $C_1$-$C_8$ alkoxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, aminosulfonylaminocarbonyl, $C_1$-$C_8$ alkylaminosulfonylaminocarbonyl, $C_1$-$C_8$ dialkylaminosulfonylaminocarbonyl, $C_1$-$C_8$ alkylsulfonylaminocarbonyl, phenylsulfonylaminocarbonyl and heterocyclylcarbonyl, wherein $C_1$-$C_4$ alkoxy and the $C_1$-$C_8$ alkoxy portion of $C_1$-$C_8$ alkoxycarbonyl is optionally substituted with one or more substituents selected from the group consisting of halogen, $C_1$-$C_4$ alkoxy, $C_1$-$C_4$ haloalkyl, amino, $C_1$-$C_6$ alkylamino, $C_1$-$C_6$ dialkylamino, cycloalkylamino, phenyl and heterocyclyl, wherein $C_1$-$C_8$ alkyl is optionally substituted with one or more substituents selected from the group consisting of halogen, hydroxyl, $C_1$-$C_4$ haloalkyl, $C_2$-$C_8$ alkenyl, $C_1$-$C_6$ alkoxy, $C_1$-$C_4$ alkoxyalkoxy, $C_3$-$C_6$ cycloalkyloxy, amino, $C_1$-$C_6$ alkylamino, $C_1$-$C_6$ dialkylamino, cycloalkylamino, aminocarbonyl, $C_1$-$C_6$ alkylaminocarbonyl, $C_1$-$C_6$ dialkylaminocarbonyl, hydroxylaminocarbonyl, cyanoaminocarbonyl, $C_1$-$C_6$ alkylsulfonylaminocarbonyl, phenylsulfonylaminocarbonyl and heterocyclyl, wherein $C_1$-$C_4$ alkoxy or $C_2$-$C_8$ alkenyl are each further optionally substituted with one or more substituents selected from the group consisting of $C_1$-$C_4$ alkoxy, $C_1$-$C_4$ haloalkyl, amino, $C_1$-$C_6$ alkylamino and $C_1$-$C_6$ dialkylamino.

As used herein, unless otherwise specified, the term "alkyl" means a saturated straight chain or branched non-cyclic hydrocarbon chain radical having an indicated number of carbon atoms (e.g., $C_1$-$C_{20}$, $C_1$-$C_{10}$, $C_1$-$C_8$, $C_1$-$C_6$, $C_1$-$C_4$, $C_1$-$C_3$, etc.). Representative saturated straight chain alkyl radicals include methyl, ethyl, n-propyl, n-butyl, n-pentyl, n-hexyl, n-heptyl, n-octyl, n-nonyl and n-decyl; while representative saturated branched chain alkyl radicals include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl radical can be unsubstituted or substituted.

As used herein, unless otherwise specified, the term "cycloalkyl" means a monocyclic or polycyclic saturated ring comprising carbon and hydrogen atoms and having no carbon-carbon multiple bonds. Examples of cycloalkyl radicals include, but are not limited to cyclopropyl, cyclobutyl, cyclopentyl, cyclohexyl, and cycloheptyl, and saturated cyclic and bicyclic terpenes. A cycloalkyl radical can include $C_3$-$C_{14}$ cycloalkyl, $C_5$-$C_8$ cycloalkyl, $C_3$-$C_8$ cycloalkyl, $C_5$-$C_6$ cycloalkyl, $C_3$-$C_6$ cycloalkyl, $C_3$-$C_5$ cycloalkyl, and the like, each of which may be unsubstituted or substituted. Preferably, the cycloalkyl radical is a monocyclic ring or bicyclic ring.

As used herein, unless otherwise specified, the term "alkenyl" means a straight chain or branched non-cyclic hydrocarbon chain radical having an indicated number of carbon atoms (e.g., $C_2$-$C_{20}$, $C_2$-$C_{10}$, $C_2$-$C_8$, $C_2$-$C_6$, $C_2$-$C_4$, etc.) and including at least one carbon-carbon double bond. Representative straight chain and branched chain alkenyl radicals include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. The double bond of an alkenyl radical can be unconjugated or conjugated to another unsaturated radical. An alkenyl radical can be unsubstituted or substituted.

As used herein, unless otherwise specified the term "alkynyl" means a straight chain or branched non-cyclic hydrocarbon chain radical having an indicated number of carbon atoms (e.g., $C_2$-$C_{20}$, $C_2$-$C_{10}$, $C_2$-$C_8$, $C_2$-$C_6$, $C_2$-$C_4$, etc.), and including at least one carbon-carbon triple bond. Representative straight chain and branched chain alkynyl radicals include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. The triple bond of an alkynyl radical can be unconjugated or conjugated to another unsaturated group. An alkynyl radical can be unsubstituted or substituted.

As used herein, unless otherwise specified, the term "halogen" or "halo" means fluorine, chlorine, bromine, or iodine. Furthermore, unless otherwise specified, the term "haloalkyl" means alkyl substituted with one or more halogens, wherein alkyl and halogen are defined as above.

As used herein, unless otherwise specified, the term "alkoxy" means —O-(alkyl), wherein alkyl is defined above.

Furthermore, as used herein, the term "haloalkoxy" means alkoxy substituted with one or more halogens, wherein alkoxy and halogen are defined as above.

As used herein, unless otherwise specified, the term "heteroaryl" means an carbocyclic aromatic ring containing from 5 to 14 ring atoms comprising at least one heteroatom, preferably 1 to 3 heteroatoms, independently selected from a nitrogen, oxygen, and sulfur atom. Heteroaryl ring structures include compounds having one or more ring structures, such as mono-, bi-, or tricyclic compounds, as well as fused heterocyclic moieties. Representative heteroaryls are triazolyl, tetrazolyl, thiadiazolyl, oxadiazolyl, pyridyl, furanyl, benzofuranyl, thiophenyl (also referred to as thienyl), thiazolyl, benzothiophenyl, benzoisoxazolyl, benzoisothiazolyl, quinolinyl, isoquinolinyl, pyrrolyl, indolyl, indazolyl, isoindolyl, azaindolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl and the like. A heteroaryl ring can be substituted or unsubstituted on a carbon or nitrogen atom, wherein substitution on a nitrogen atom may optionally form a quaternary salt moiety.

As used herein, unless otherwise specified, the term "heterocyclyl" means a saturated or partially saturated monocyclic, bicyclic or polycyclic carbocyclic ring containing from 5 to 14 ring atoms comprising at least one heteroatom, preferably 1 to 3 heteroatoms, independently selected from, a nitrogen, oxygen, and sulfur atom. Representative heterocyclyls are oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like. A heterocyclyl radical can be unsubstituted or substituted on a carbon or nitrogen atom, wherein substitution on a nitrogen atom may form a quaternary salt moiety.

As used herein, unless otherwise specified, the term "CH ($C_nH_{2n+1}$)," wherein n is an integer from 1 to 8, refers to an alkyl chain radical of the formula: —$(CH_2)_{1-7}$—$CH_3$ substituted on the B variable of either Formula (I) or Formula (II), wherein B is —CH—.

As used herein, unless otherwise specified, the term "CH ($C_mH_{2m+1}$)," wherein m is an integer from 1 to 8, refers to an alkyl chain radical of the formula: —$(CH_2)_{1-7}$—$CH_3$ substituted on the $B_1$ variable of either Formula (Ia) or Formula (IIa), wherein $B_1$ is —CH—.

As used herein, unless otherwise specified, the term "alkanoyl" refers to a radical of the formula: —C(O)-alkyl, wherein alkyl is defined above.

As used herein, unless otherwise specified, the term "alkanoylamino" refers to a radical of the formula: —NH—C(O)-alkyl, wherein alkyl is defined above.

As used herein, unless otherwise specified, the term "alkanoyloxy" refers to a radical of the formula: —O—C(O)-alkyl, wherein alkyl is defined above.

As used herein, the term "alkoxyalkoxy" refers to a radical of the formula: —O-alkyl-O-alkyl, wherein alkyl is defined above (e.g., $C_1$-$C_6$ alkoxyalkoxy and the like).

As used herein, the term "alkoxyalkyl" refers to a radical of the formula: -alkyl-O-alkyl, wherein alkyl is defined above (e.g., $C_1$-$C_6$ alkoxyalkyl and the like).

As used herein, the term "alkoxycarbonyl" refers to a radical of the formula: —C(O)—O-alkyl, wherein alkyl is defined above.

As used herein, unless otherwise specified, the term "alkylamino" refers to a radical of the formula: —NH-alkyl, wherein alkyl is defined above.

As used herein, unless otherwise specified, the term "alkylaminoalkyl" refers to a radical of the formula: -alkyl-NH-alkyl, wherein alkyl is defined above.

As used herein, unless otherwise specified, the term "alkylaminocarbonyl" refers to a radical of the formula: —C(O)—NH-alkyl, wherein alkyl is defined above.

As used herein, unless otherwise specified, the term "alkylaminosulfonyl" refers to a radical of the formula: —$SO_2$—NH-alkyl, wherein alkyl is defined above.

As used herein, unless otherwise specified, the term "alkylaminosulfonylaminocarbonyl" refers to a radical of the formula: —C(O)—NH—$SO_2$—NH-alkyl, wherein alkyl is defined above.

As used herein, the term "alkylcarbonyl" refers to a radical of the formula: —C(O)-alkyl, wherein alkyl is defined above.

As used herein, unless otherwise specified, the term "alkylsulfonyl" refers to a radical of the formula: —$SO_2$-alkyl, wherein alkyl is defined above.

As used herein, unless otherwise specified, the term "alkylsulfonylaminocarbonyl" refers to a radical of the formula: —C(O)—NH—$SO_2$-alkyl, wherein alkyl is defined above.

As used herein, unless otherwise specified, the terms "alkylthio" and "alkylthioether" refer to a radical of the formula: —S-alkyl, wherein alkyl is defined above.

As used herein, unless otherwise specified, the term "alkylthiono" refers to a radical of the formula: —C(S)-alkyl, wherein alkyl is defined above.

As used herein, unless otherwise specified, the term "amino" refers to a radical of the formula: —$NH_2$.

As used herein, unless otherwise specified, the term "aminoalkyl" refers to a radical of the formula: -alkyl-$NH_2$, wherein alkyl is defined above.

As used herein, unless otherwise specified, the term "aminocarbonyl" refers to a radical of the formula: —C(O)—$NH_2$, wherein alkyl is defined above.

As used herein, unless otherwise specified, the terms "aminosulfonyl", "sulfonamide" and "sulfonamido" refer to a radical of the formula: —$SO_2$—$NH_2$.

As used herein, unless otherwise specified, the term "aminosulfonylaminocarbonyl" refers to a radical of the formula: —C(O)—NH—$SO_2$—$NH_2$.

As used herein, unless otherwise specified, the term "aralkanoylamino" refers to a radical of the formula: —NH—C(O)-alkyl-aryl, wherein alkyl and aryl are defined above.

As used herein, unless otherwise specified, the terms "aroyl" and "arylcarbonyl" refer to a radical of the formula: —C(O)-aryl, wherein aryl is defined above (e.g., phenylcarbonyl and the like).

As used herein, unless otherwise specified, the term "aroylamino" refers to a radical of the formula: —NH—C(O)-aryl, wherein aryl is defined above.

As used herein, unless otherwise specified, the term "arylalkoxycarbonyl" refers to a radical of the formula: —C(O)—O-alkyl-aryl, wherein alkyl and aryl are defined above (e.g., benzyloxycarbonyl, and the like).

As used herein, unless otherwise specified, the term "arylalkyl" refers to a radical of the formula: -alkyl-aryl, wherein alkyl and aryl are defined above.

As used herein, unless otherwise specified, the term "arylalkylamino" refers to a radical of the formula: —NH-alkyl-aryl, wherein alkyl and aryl are defined above.

As used herein, unless otherwise specified, the term "N-aryl-N-alkyl-aminocarbonyl" refers to a radical, wherein amino is disubstituted, of the formula: —C(O)—N(aryl-alkyl), wherein alkyl and aryl are defined above (e.g., N-phenyl-N-alkyl-aminocarbonyl and the like).

As used herein, unless otherwise specified, the term "arylalkylsulfonyl" refers to a radical of the formula: —$SO_2$-alkyl-aryl, wherein alkyl and aryl are defined above.

As used herein, unless otherwise specified, the term "arylalkylthio" refers to a radical of the formula: —S-alkyl-aryl, wherein alkyl and aryl are defined above.

As used herein, unless otherwise specified, the term "arylalkylthiono" refers to a radical of the formula: —C(S)-alkyl-aryl, wherein alkyl and aryl are defined above.

As used herein, unless otherwise specified, the term "arylamino" refers to a radical of the formula: —NH-aryl, wherein aryl is defined above.

As used herein, unless otherwise specified, the term "arylaminocarbonyl" refers to a radical of the formula: —C(O)—NH-aryl, wherein aryl is defined above (e.g., phenylaminocarbonyl and the like).

As used herein, unless otherwise specified, the term "aryloxy" refers to a radical of the formula: —O-aryl, wherein aryl is defined above.

As used herein, unless otherwise specified, the term "arylsulfonyl" refers to a radical of the formula: —$SO_2$-aryl, wherein aryl is defined above (e.g., phenylsulfonyl and the like).

As used herein, unless otherwise specified, the term "arylsulfonylaminocarbonyl" refers to a radical of the formula: —C(O)—NH—$SO_2$-aryl, wherein aryl is defined above (e.g., phenylsulfonylaminocarbonyl, and the like).

As used herein, unless otherwise specified, the term "arylthio" refers to a radical of the formula: —S-aryl, wherein aryl is defined above.

As used herein, unless otherwise specified, the term "arylthiono" refers to a radical of the formula: —C(S)-aryl, wherein aryl is defined above.

As used herein, the term "carbamyl" refers to a radical of the formula: —C(O)—$NH_2$.

As used herein, the term "carbonyl" refers to a radical of the formula: —C(O)—.

As used herein, the term "carboxy" refers to a radical of the formula: —COOH or —$CO_2$H.

As used herein, unless otherwise specified, the term "cyanoaminocarbonyl" refers to a radical of the formula: —C(O)—NH—C≡N or —C(O)—NH—CN.

As used herein, unless otherwise specified, the term "cycloalkylalkoxy" refers to a radical of the formula: —O-alkyl-cycloalkyl, wherein cycloalkyl is defined above (e.g., cyclopentyl-alkoxy, cyclobutyl-alkoxy and the like).

As used herein, unless otherwise specified, the term "cycloalkylalkyl" refers to a radical of the formula: -alkyl-cycloalkyl, wherein cycloalkyl is defined above (e.g., $C_3$-$C_6$ cycloalkylalkyl and the like).

As used herein, unless otherwise specified, the term "cycloalkylamino" refers to a radical of the formula: —NH-cycloalkyl, wherein cycloalkyl is defined above.

As used herein, unless otherwise specified, the term "cycloalkyloxy" refers to a radical of the formula: —O-cycloalkyl, wherein cycloalkyl is defined above (e.g., $C_3$-$C_6$ cycloalkyloxy and the like).

As used herein, unless otherwise specified, the term "cycloalkylthio" refers to a radical of the formula: —S-cycloalkyl, wherein cycloalkyl is defined above.

As used herein, unless otherwise specified, the term "dialkylamino" refers to a radical of the formula: —N(alkyl)$_2$, wherein alkyl is defined above.

As used herein, unless otherwise specified, the term "dialkylaminoalkyl" refers to a radical of the formula: -alkyl-N(alkyl)$_2$, wherein alkyl is defined above.

As used herein, unless otherwise specified, the term "dialkylaminocarbonyl" refers to a radical of the formula: —C(O)—N(alkyl)$_2$, wherein alkyl is defined above (e.g., $C_1$-$C_6$ dialkylaminocarbonyl and the like).

As used herein, unless otherwise specified, the term "dialkylaminosulfonyl" refers to a radical of the formula: —$SO_2$—N(alkyl)$_2$, wherein alkyl is defined above (e.g., $C_1$-$C_6$ dialkylaminosulfonyl and the like).

As used herein, unless otherwise specified, the term "dialkylaminosulfonylaminocarbonyl" refers to a radical of the formula: —C(O)—NH—$SO_2$—N(alkyl)$_2$, wherein alkyl is defined above.

As used herein, the term "formyl" refers to a radical of the formula: —C(O)H.

As used herein, the term "guanidino" refers to a radical of the formula: —NH—C(NH)—$NH_2$.

As used herein, the term "halo" or "halogen" generally refers to a halogen atom radical, such as fluoro, chloro, bromo and iodo.

As used herein, the term "haloalkenyl" refers to a radical of the formula: -alkenyl-halo, wherein alkenyl and halo are defined above and may be partially or completely substituted where allowed by available valences with one or more halogen atoms (e.g., trifluoroalkenyl, and the like).

As used herein, the term "haloalkoxy" refers to a radical of the formula: —O-alkyl-halo, wherein alkyl and halo are defined above and may be partially or completely substituted where allowed by available valences with one or more halogen atoms (e.g., trifluoroalkoxy, difluoroalkoxy, and the like).

As used herein, the term "haloalkyl" refers to a radical of the formula: -alkyl-halo, wherein alkyl and halo are defined above and may be partially or completely substituted where allowed by available valences with one or more halogen atoms (e.g., trifluoroalkyl and the like).

As used herein, unless otherwise specified, the term "heteroarylalkyl" refers to a radical of the formula: -alkyl-heteroaryl, wherein alkyl and heteroaryl are defined above.

As used herein, unless otherwise specified, the terms "heterocyclylalkyl" and "alkylheterocyclyl" refer to a radical of the formula: -alkyl-heterocyclyl, wherein alkyl and heterocyclyl are defined above (e.g., $C_1$-$C_4$ morpholinylalkyl and the like)).

As used herein, unless otherwise specified, the term "heterocyclylamino" refers to a radical of the formula: —NH-heterocyclyl, wherein heterocyclyl is defined above.

As used herein, unless otherwise specified, the term "heterocyclylcarbonyl" refers to a radical of the formula: —C(O)-heterocyclyl, wherein alkyl and aryl are defined above (e.g., morpholinylcarbonyl, piperidinylcarbonyl, and the like).

As used herein, unless otherwise specified, the term "heterocyclyloxy" refers to a radical of the formula: —O-heterocyclyl, wherein heterocyclyl is defined above.

As used herein, unless otherwise specified, the term "heterocyclylthio" refers to a radical of the formula: —S-heterocyclyl, wherein heterocyclyl is defined above.

As used herein, the term "hydroxylalkyl" refers to a radical of the formula: -alkyl-OH, wherein alkyl is defined above and may be partially or completely substituted where allowed by available valences with one or more hydroxyl substituents.

As used herein, unless otherwise specified, the term "hydroxylaminocarbonyl" refers to a radical of the formula: —C(O)—NH—OH.

As used herein, the term "thiol" refers to a radical of the formula: —SH.

For the purposes of this invention, where one or more functionalities encompassing substituent variables for a compound of Formula (I) are incorporated into a compound of Formula (I), each functionality appearing at any location within the disclosed compound may be independently selected, and as appropriate, independently and/or optionally substituted.

As used herein, the term "substituent" means positional variables on the atoms of a core molecule that are known to those skilled in the art to be chemical moieties that are appropriate for substitution at a designated atom position, replacing one or more hydrogens on the designated atom with a selection from the indicated group, provided that the designated atom's normal valency under the existing circumstances is not exceeded, and that the substitution results in a stable compound. Combinations of substituents and/or variables are permissible only if such combinations result in stable compounds. It should also be noted that any carbon as well as heteroatom with unsatisfied valences as described or shown herein is assumed to have a sufficient number of hydrogen atom(s) to satisfy the valences described or shown.

As used herein, the terms "independently substituted," or "each selected from", and variations thereof, mean that, when any substituent occurs more than once in a substituent list or as a portion of a substituent in the list for Formula (I) or another structural formulae of the invention, the pattern of substitution on any particular substituent at each occurrence is independent of the pattern at any other occurrence. Further, the use of a generic substituent variable on any formula or structure position for a compound of the present invention is understood to include the replacement of the generic substituent with species substituents that are included within the particular genus, e.g., aryl may be replaced with phenyl or naphthalenyl and the like, and that the resulting compound is to be included within the scope of the compounds representative of the present invention.

As used herein, the term "optionally substituted" means optional substitution with the specified groups, radicals or moieties.

As used herein, unless otherwise specified, the term "substituted" means a group substituted by one to four or more substituents, such as, alkyl, alkenyl, alkynyl, cycloalkyl, aroyl, halo, haloalkyl (e.g., trifluoromethyl), haloalkoxy (e.g., trifluoromethoxy), hydroxyl, alkoxy, alkylthioether, cycloalkyloxy, heterocyclyloxy, oxo, alkanoyl, aryl, arylalkyl, heteroaryl, heteroarylalkyl, heterocyclyl, aryloxy, alkanoyloxy, amino, arylamino, arylalkylamino, cycloalkylamino, heterocyclylamino, mono- and di-substituted amino (in which the one or two substituents on the amino group are selected from alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, cycloalkylthio, heterocyclylthio, alkylthiono, arylthiono, arylalkylthiono, alkylsulfonyl, arylsulfonyl, arylalkylsulfonyl, sulfonamido (e.g., $SO_2NH_2$), substituted sulfonamido, nitro, cyano, carboxy, carbamyl (e.g., $CONH_2$), substituted carbamyl (e.g., CONH-alkyl, CONH-aryl, CONH-arylalkyl or instances where there are two substituents on nitrogen selected from alkyl or arylalkyl), alkoxycarbonyl, aryl, substituted aryl, guanidino, substituted or unsubstituted heterocyclylalkyl, substituted or unsubstituted heteroaryl.

Whenever a range of the number of atoms in a structure is indicated (e.g., a $C_1$-$C_8$, $C_1$-$C_6$, $C_1$-$C_4$, or $C_1$-$C_3$ alkyl, $C_1$-$C_4$ haloalkyl or $C_1$-$C_4$ alkylamino, $C_2$-$C_8$ alkenyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), 2-8 carbon atoms (e.g., $C_2$-$C_8$) as used with respect to any chemical group (e.g., alkyl, haloalkyl, alkylamino, alkenyl, etc.) referenced herein encompasses and specifically describes 1, 2, 3, 4, 5, 6, 7, or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, 5-6 carbon atoms, 5-7 carbon atoms, 5-8 carbon atoms, 6-7 carbon atoms, or 6-8 carbon atoms, as appropriate).

Compound names used herein were obtained using the Autonom batch naming feature of ChemDraw Ultra Version 10.0.4, provided by CambridgeSoft. When the compound name disclosed herein conflicts with the structure depicted, the structure shown will supercede the use of the name to define the compound intended.

The invention encompasses uses of all compounds described by Formulas (I) and (II) without limitation. However, for the purposes of further illustration, preferred aspects and elements of the invention are discussed herein.

With respect to Formulas (I) and (II), W is selected from the group consisting of C(O), C(S), and $CH_2$. According to certain aspects of the invention, W is C(O), especially with respect to compounds of Formula (I) and B is $CH_2$ or $CH(C_nH_{2n+1})$, wherein n is an integer from 1 to 8.

$R_1$ and $R_2$ can be the same or different, and are selected from the group consisting of H and $C_1$-$C_3$ alkyl, or $R_1$ and $R_2$ may be taken together with the carbon atom to which they are attached to form a $C_3$-$C_5$ or $C_3$-$C_6$ cycloalkyl ring or a carbonyl group. Preferably, $R_1$ and $R_2$ are H or $C_1$-$C_3$ alkyl. More preferably, $R_1$ is H and $R_2$ is $C_1$-$C_3$ alkyl.

$R_3$ is selected from the group consisting of H, halogen, $C_1$-$C_4$ alkyl, $C_1$-$C_4$ alkoxy, $C_1$-$C_4$ haloalkyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy substituents. However, $R_3$ preferably is H.

According to one aspect of the invention, at least one of $R_4$, $R_5$, $R_6$ and $R_7$ is not H. Thus, according to this aspect of the invention, at least one of $R_4$, $R_5$, $R_6$ and $R_7$, and in one embodiment $R_5$, $R_6$, and/or $R_7$, is selected from the group consisting of hydroxyl, halogen, CN, $NO_2$, sulfonamide, $C_1$-$C_8$ alkyl, $C_3$-$C_6$ cycloalkyl, cycloalkyloxy, $C_1$-$C_6$ alkoxy, $C_1$-$C_6$ haloalkoxy, $C_1$-$C_4$ haloalkyl, $C_2$-$C_8$ alkenyl, amino, $C_1$-$C_4$ dialkylamino, $C_1$-$C_4$ alkylamino, morpholinyl, heteroaryl, arylamino, arylalkylamino, phenyl, and C(O)R', NR' (COR"), NR'$SO_2$R" and NR'(CONR"R'''), wherein R', R" and R''' are independently H, $C_1$-$C_6$ alkyl, phenyl or substituted phenyl, and wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl, and the phenyl is optionally substituted with one or more substituents selected from the group consisting of halogen, $NO_2$, CN, $C_1$-$C_4$ alkyl, $C_1$-$C_4$ haloalkyl, and $C_1$-$C_4$ alkoxy, or any sub-group or sub-combination thereof.

In a further embodiment, either $R_5$ or $R_6$, or both, are not H. Thus, either $R_5$ or $R_6$, or both, are independently selected as above or from the group consisting of halogen, $C_1$-$C_8$ alkyl, $C_3$-$C_6$ cycloalkyl, cycloalkyloxy, $C_1$-$C_6$ alkoxy, $C_1$-$C_4$ haloalkyl, amino, $C_1$-$C_4$ dialkylamino, $C_1$-$C_4$ alkylamino, and morpholinyl, wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl.

In one embodiment, $R_5$ is H and $R_6$ is selected as described above, or $R_6$ is selected from the group consisting of halogen, $C_1$-$C_3$ alkyl, $C_1$-$C_6$ alkoxy, cycloalkyloxy, $C_1$-$C_4$ dialkylamino, and $C_1$-$C_4$ haloalkyl. More specific examples of suitable $R_6$ groups include chloro, bromo, methyl, ethyl, propyl, i-propyl, methoxy, ethoxy, propoxy, i-propoxy, cyclohexyloxy, dimethylamino, and $CF_3$. When $R_6$ is not H, it is suitable that each of $R_4$, $R_5$, and $R_7$ are H.

When $R_5$ is not H, $R_5$ advantageously can be selected as described above, or from the group consisting of CN, halogen, $C_1$-$C_6$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino and morpholinyl, wherein the $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl. Specific examples of suitable $R_5$ groups include methyl, ethyl, propyl, or CN. When $R_5$ is not H, it is suitable that each of $R_4$, $R_6$, and $R_7$ are H.

When $R_7$ is not H, $R_7$ can be selected as described above, or from the group consisting of halogen, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkylamino, $C_1$-$C_4$ alkylamino, $C_3$-$C_6$ cycloalkylamino, and morpholinyl, wherein the $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl. More specific examples of $R_7$ include $C_1$-$C_8$ alkyl, amino, or $C_1$-$C_4$ alkylamino, such as methyl, ethyl, propyl, or amino. When $R_7$ is not H, it is suitable that $R_4$, $R_5$, and $R_6$ are H.

Alternatively, or in addition, $R_4$ and $R_5$, $R_5$ and $R_6$, or $R_6$ and $R_7$, may be taken together with the carbon atoms to which they are attached to form a ring, preferably a 5 or 6 membered heterocyclyl ring, fused to the benzo portion of the compound of Formula (I). Non-limiting examples of such fused heterocyclyl rings include a fused [1,4]dioxanyl or fused [1,3]dioxolanyl ring.

Additional compounds of Formula (I) are those in which wherein at least one of $R_3$, $R_4$, $R_5$, $R_6$, or $R_7$ is hydroxyl, $C_1$-$C_6$ haloalkoxy, $C_2$-$C_6$ alkenyl, or $C_1$-$C_8$ alkyl substituted with an arylamino or arylalkylamino. In a further embodiment, at least one of $R_3$, $R_4$, $R_5$, $R_6$, or $R_7$ is a $C_1$-$C_6$ haloalkoxy. Non-limiting examples of haloalkoxy groups include —$OCHF_2$.

Alternatively, or in addition, at least one of $R_3$, $R_4$, $R_5$, $R_6$, or $R_7$ is C(O)R', NR'(COR"), NR'SO$_2$R" and NR' (CONR"R'''), wherein R', R" and R''' are independently H, $C_1$-$C_6$ alkyl, phenyl or substituted phenyl. Non-limiting examples of such NR'(CONR"R''') groups include urea (e.g., $NH(CO)NH_2$).

X is selected from the group consisting of H, CN, C(O)OR$_8$, wherein R$_8$ is H or $C_1$-$C_8$ alkyl, and $C_1$-$C_8$ alkyl optionally is substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, phenyl, and morpholinyl; C(O)NR$_9$R$_{10}$, wherein R$_9$ and R$_{10}$ are independently selected from the group consisting of H and $C_1$-$C_6$ alkyl, or R$_9$ and R$_{10}$ together with the nitrogen to which they are attached form a heterocyclyl ring such as morpholinyl; $CH_2OR_{11}$, wherein R$_{11}$ is H, $C_1$-$C_8$ alkyl, or $C_3$-$C_6$ cycloaklyl, wherein $C_1$-$C_8$ alkyl optionally is substituted with one or substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2NR_9R_{10}$, wherein R$_9$ and R$_{10}$ are as defined above; $CH_2Z$, wherein Z is halogen; C(O)NHOH; C(O)NHCN; C(O)N(R$_1$)SO$_2$R$_{13}$, wherein R$_{13}$ is $C_1$-$C_4$ alkyl, phenyl, or substituted phenyl; $C_1$-$C_8$ alkyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino; provided that when the compound is a compound of Formula (I), and each of $R_4$, $R_5$, $R_6$ and $R_7$ are H, then X is not C(O)OH.

While X can be chosen as described above, X can also be selected from the group consisting of CN; C(O)OR$_8$, wherein R$_8$ is $C_1$-$C_8$ alkyl, optionally substituted with phenyl; C(O) NR$_9$R$_{10}$, wherein R$_9$ and R$_{10}$ are independently selected from the group consisting of H and $C_1$-$C_6$ alkyl, or R$_9$ and R$_{10}$ together with the nitrogen to which they are attached form a heterocyclyl ring such as morpholinyl; $CH_2OR_{11}$, wherein R$_{11}$ is H, $C_1$-$C_8$ alkyl, or $C_3$-$C_6$ cycloaklyl, wherein $C_1$-$C_8$ alkyl optionally is substituted with one or substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2NR_9R_{10}$, wherein R$_9$ and R$_{10}$ are as defined above; and $CH_2Z$, wherein Z is halogen; C(O) NHOH; C(O)NHCN; C(O)N(R$_1$)SO$_2$R$_{13}$, wherein in R$_{13}$ is $C_1$-$C_4$ alkyl, phenyl, or substituted phenyl.

In another embodiment, X is selected from the group consisting of CN; C(O)OR$_8$, wherein R$_8$ is $C_1$-$C_8$ alkyl, optionally substituted with a phenyl; $CH_2OR_{11}$, wherein R$_{11}$ is H, $C_1$-$C_8$ alkyl, or $C_3$-$C_6$ cycloalkyl, wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2NR_9R_{10}$, wherein R$_9$ and R$_{10}$ are independently selected from the group consisting of H and $C_1$-$C_6$ alkyl, or R$_9$ and R$_{10}$ together with the nitrogen to which they are attached form a heterocyclyl ring such as morpholinyl; and $CH_2Z$, wherein Z is halogen. X can be selected as C(O) OR$_8$, wherein R$_8$ is $C_1$-$C_6$ alkyl, optionally substituted with a phenyl, or $CH_2Z$, wherein Z is halogen. More specific examples of suitable X groups include C(O)OR$_8$, wherein R$_8$ is methyl, ethyl, propyl, butyl, t-butyl, or benzyl.

According to another aspect of the invention, when X is selected as described above, and is not C(O)OH, each of $R_4$, $R_5$, $R_6$ and $R_7$ can be H. Also, when at least one of $R_4$, $R_5$, $R_6$ and $R_7$ is not H, and is instead selected as described above, X can be C(O)OH. This aspect of the invention is especially applicable to Formula (I) compounds.

According to another aspect of the invention, compounds of Formula (I) are selected such that W is C(S) or $CH_2$, B is $CH_2$, and $R_1$-$R_7$ are selected as described above.

In other embodiments, W$_1$ is selected from C(O) or $CH_2$. In certain embodiments, W$_1$ is selected from CH($C_mH_{2m+1}$) and m is an integer selected from 1, 2 or 3. In certain embodiments, Ring $C_1$ is selected from the group consisting of a thienyl ring, a pyridinyl ring, a cyclohexyl ring, a cyclohexenyl ring, a cyclohexa-1,4-dienyl ring, a benzo[d][1,3]dioxolyl ring and a 2,3-dihydrobenzo[b][1,4]dioxinyl ring, each of said rings fused to the moiety of Formula (IIa), wherein benzo[d][1,3]dioxolyl and 2,3-dihydrobenzo[b][1,4]dioxinyl, each having a benzo ring portion, are fused via said benzoportion.

In other embodiments, $R_{20}$ and $R_{21}$ are each H. In certain embodiments, $R_{20}$ and $R_{21}$ are each $C_1$-$C_3$ alkyl. In certain embodiments, $R_{20}$ and $R_{21}$ are taken together with the carbon atom to which they are attached to form carbonyl. In certain embodiments, when X is absent, then $R_{20}$ and $R_{21}$ may be taken together with the carbon atom to which they are attached to form a $C_3$-$C_5$ or $C_3$-$C_6$ cycloalkyl ring selected from cyclopropyl, cyclopentyl or cyclohexyl.

In certain embodiments, $R_{22}$ is selected from the group consisting of H, halogen, $C_1$-$C_4$ alkyl, $C_1$-$C_4$ alkoxy, $C_1$-$C_4$ haloalkyl, cyano, thienyl, furanyl, pyridinyl, pyrimidinyl and phenyl, wherein phenyl is optionally substituted with one or two halogen, $C_1$-$C_4$ alkyl or $C_1$-$C_4$ alkoxy substituents.

In certain embodiments, when one, two or three of $R_{23}$, $R_{24}$, $R_{25}$ and $R_{26}$ are each H, then three, two or one of $R_{23}$, $R_{24}$, $R_{25}$ and $R_{26}$, respectively, are each selected from hydroxyl, halogen, cyano, nitro, $C_1$-$C_8$ alkyl, $C_1$-$C_6$ alkoxy, $C_1$-$C_6$ alkoxyalkoxy, $C_1$-$C_6$ alkoxyalkyl, $C_1$-$C_6$ difluoroalkoxy, $C_1$-$C_6$ trifluoroalkoxy, $C_1$-$C_4$ trifluoroalkyl, $C_2$-$C_6$ alkenyl, $C_2$-$C_4$ trifluoroalkenyl, amino, $C_1$-$C_4$ alkylamino, $C_1$-$C_4$ dialkylamino, $C_1$-$C_4$ aminoalkyl, $C_1$-$C_4$ alkylaminoalkyl or $C_1$-$C_4$ dialkylaminoalkyl.

In certain embodiments, when three of $R_{23}$, $R_{24}$, $R_{25}$ and $R_{26}$ are each H, then one of $R_{23}$, $R_{24}$, $R_{25}$ and $R_{26}$ is selected from phenyl, cyclopentyl, cyclopropyl, benzyloxy, $C_1$-$C_4$ cyclopentylalkoxy, $C_1$-$C_4$ cyclobutylalkoxy, cyclopentyloxy, pyrrolidinyl, piperidinyl, morpholinyl, $C_1$-$C_4$ morpholinylalkyl, thienyl, pyridinyl, pyrimidinyl, or amino, wherein amino is optionally disubstituted with one substituent selected from hydrogen or $C_1$-$C_6$ alkyl and the other is selected from phenyl, $C_1$-$C_4$ alkylcarbonyl, aminocarbonyl, $C_1$-$C_4$ alkylaminocarbonyl, $C_1$-$C_4$ dialkylaminocarbonyl, phenylcarbonyl, phenylaminocarbonyl, N-phenyl-N—$C_1$-$C_4$ alkyl-aminocarbonyl, $C_1$-$C_6$ alkylsulfonyl or phenylsulfonyl, and wherein each instance of phenyl is optionally substituted with one or two substituents selected from halogen, $C_1$-$C_4$ alkyl or $C_1$-$C_4$ alkoxy.

In certain embodiments, $X_1$ is absent or is selected from the group consisting of H, cyano, $C_1$-$C_4$ alkyl, $C_1$-$C_4$ alkoxy, $C_1$-$C_4$ haloalkyl, $C_1$-$C_6$ hydroxylalkyl, $C_1$-$C_6$ alkoxyalkyl, $C_1$-$C_4$ morpholinylalkyl, amino, $C_1$-$C_4$ alkylamino, $C_1$-$C_4$ dialkylamino, $C_1$-$C_4$ aminoalkyl, $C_1$-$C_4$ alkylaminoalkyl, $C_1$-$C_4$ dialkylaminoalkyl, carboxy, $C_1$-$C_6$ alkoxycarbonyl, benzyloxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, amino sulfonylaminocarbonyl, $C_1$-$C_8$ alkylaminosulfonylaminocarbonyl $C_1$-$C_8$ dialkylaminosulfonylaminocarbonyl, $C_1$-$C_8$ alkylsulfonylaminocarbonyl, phenylsulfonylaminocarbonyl, morpholinylcarbonyl and piperidinylcarbonyl.

In one embodiment, a compound useful for the methods provided herein is Compound 1:

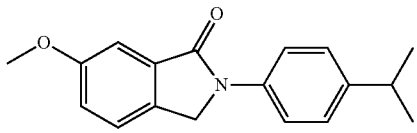

Compound 1

In other embodiments, Compound 1 is also referred to as 2-(4-isopropylphenyl)-6-methoxyisoindolin-1-one.

As those of ordinary skill in the art will appreciate, many of the molecules described herein may contain one or more chiral centers, wherein more than one stereoisomer (e.g., diastereomer or enantiomer) of the molecule may exist. If the stereochemistry of a structure or a portion of a structure is not indicated, for example, with bold or dashed lines, the structure or portion of the structure is to be interpreted as encompassing all stereoisomers of it. The invention specifically contemplates any individual stereoisomers (e.g., diastereomers or enantiomers) of the compounds described herein, as well as mixtures thereof (e.g., racemic mixtures).

The compounds described herein can be prepared by any of several techniques known by those skilled in the art. By way of a non-limiting example, the compounds can be prepared as described in International Publication No. WO2007/109211, pub. Sep. 27, 2007, which is incorporated by reference herein in its entirety. In a specific embodiment, the compounds for use in the methods described herein include those described in International Publication No. WO 2007/109211, pub. Sep. 27, 2007, which is incorporated by reference herein in its entirety.

Nucleic Acid Constructs

In one aspect, the present invention provides nucleic acid constructs for use in cell-based and cell-free screening assays for the identification or validation of compounds that modulate ribosomal frameshifting. In another aspect, the present invention provides nucleic acid constructs for use in cell-based and cell-free screening assays for the identification or validation of compounds that modulate the efficiency of programmed ribosomal frameshifting.

Presented herein are nucleic acid constructs comprising nucleic acid residues of an exon(s) of SMN or a fragment thereof, a reporter gene coding sequence lacking a start codon, and in some instances, nucleic acid residues of an intron(s) of SMN. In specific aspects, a nucleic acid construct described herein comprises a fragment of the nucleic residues of an exon 8 of SMN fused to a reporter gene coding sequence lacking the start codon, wherein that the first codon of the reporter gene coding sequence and the first codon of the fragment are out of frame with each other in the mRNA transcript transcribed from the nucleic acid construct and the presence of a stop codon in the mRNA transcript causes translation termination prior to translation of the reporter gene coding sequence (i.e., an aberrant stop codon). In such mRNA transcripts, the first start codon and the aberrant stop codon are in the same contiguous open reading frame without any interruption by, e.g., a stop codon. In the presence of certain compounds, the open reading frame may shift so that the start codon and the aberrant stop codon are no longer in the same open reading frame, and instead the first start codon and the stop codon found at the end of the reporter gene coding sequence are in the same contiguous open reading frame without any interruptions. As a result, an increase in fusion protein with activity of the reporter gene coding sequence can be detected.

In one aspect, the nucleic acid constructs described herein comprise deoxyribonucleic acid (DNA) residues or analogs thereof. In one embodiment, a nucleic acid construct comprises, in 5' to 3' order: (i) a fragment of the nucleic acid residues of exon 8 of SMN; and (ii) a reporter gene coding sequence lacking a start codon, wherein the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and a stop codon is upstream of the reporter gene in the mRNA transcript. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In certain embodiments, the fragment of the nucleic acid residues of exon 8 of SMN consists of the first 3, 5, 7, or 9 nucleotides from the 5' end of exon 8 of SMN. In other embodiments, the fragment of the nucleic acid residues of exon 8 of SMN consists of the first 11, 13, 15, 17, or 19 nucleotides from the 5' end of exon 8 of SMN. In a specific embodiment, the fragment of the nucleic acid residues of exon 8 SMN consists of the first 21 nucleotides from the 5' end of exon 8 of SMN. In another specific embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the fragment of the nucleic acid residues of exon 8 of SMN. In some embodiments, the nucleic acid construct comprises one or more nucleotide sequences encoding one or more amino acid sequence (e.g., peptides or polypeptides), wherein said one or more nucleotide sequences are upstream (5') of the fragment of the nucleic acid residues of exon 8 of SMN, and wherein the first codon of each of the one or more nucleotide sequences and the first codon of the fragment are in frame with the each other in the mRNA transcript transcribed from the nucleic acid construct. In a specific embodiment, the one or more nucleotide sequences encoding one or more amino acid sequence (e.g., peptides or polypeptides) upstream (5') of the fragment of the nucleic acid residues of exon 8 of SMN contains a start codon. In accordance with such embodiments, the first start codon and the stop codon upstream of the reporter gene coding sequence are in the same contiguous open reading frame.

In another embodiment, a nucleic acid construct comprises, in 5' to 3' order: (a) a start codon; (b) a fragment of the nucleic acid residues of exon 8 of SMN; and (c) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and a stop codon is upstream of the reporter gene coding sequence in the mRNA transcript; and (ii) the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) a start codon, (b) a fragment of the nucleic acid residues of exon 7 of SMN; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon; and (iii) the fragment of the nucleic acid residues of exon 7 of SMN comprises any number of nucleotides of exon 7 of SMN so long as in the mRNA transcript transcribed from the nucleic acid construct the first start codon and the stop codon upstream of the reporter gene coding sequence are maintained in the same contiguous open reading frame without any interruption by, e.g., stop codon. In certain embodiments, the first codon of the fragment of the nucleic acid residues of exon 7 of SMN and the first codon of the fragment of the nucleic acid residues of exon 8 of SMN are in frame with each other in the mRNA transcript transcribed from the nucleic acid construct. In certain embodiments, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In some embodiments, the nucleic acid construct comprises one or more nucleotide sequences encoding one or more amino acid sequences (e.g., peptides or polypeptides), wherein said one or more nucleotide sequences are upstream (5') of the fragment of the nucleic acid residues of exon 7 of SMN and downstream (3') to the start codon. In certain embodiments, the first codon of each of the one or more nucleotide sequences encoding the one or more amino acid sequences, the first codon of the fragment of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter coding sequence); (ii) in the mRNA transcript transcribed from the nucleic acid construct, the first start codon and the stop codon upstream of the reporter gene coding sequence are in the same contiguous open reading frame without any interruption by, e.g., a stop codon; and (iii) the fragment of the nucleic acid residues of exon 7 of SMN comprises any number of nucleotides of exon 7 of SMN so long as in the mRNA transcript transcribed from the nucleic acid construct the first start codon and the stop codon upstream of the reporter gene coding sequence are maintained in the same contiguous open reading frame without any interruption by, e.g., stop codon. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, an internal start codon (e.g., ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the first codon of the nucleic acid residues of exon 6 of SMN or a fragment thereof, the first codon of the fragment of the nucleic acid residues of exon 7 of SMN, and the first codon of the fragment of exon 8 of SMN are in frame with each other in the mRNA transcript transcribed from the nucleic acid construct. In some embodiments, the nucleic acid construct comprises one or more nucleotide sequences encoding one or more amino acid sequences (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon; and (iii) the fragment of the nucleic acid residues of exon 7 of SMN comprises any number of nucleotides of exon 7 of SMN required for splicing and so long as in the mRNA transcript transcribed from the nucleic acid construct the start codon and the stop codon upstream of the reporter gene coding sequence are maintained in the same contiguous open reading frame without any interruption by, e.g., stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In some embodiments, the nucleic acid construct comprises one or more nucleotide sequences encoding one or more amino acid sequences (e.g., peptides or polypeptides), wherein said one or more nucleotide sequences are upstream (5') of the fragment of the nucleic acid residues of exon 7 of SMN and downstream (3') to the start codon. In certain embodiments, the first codon of each of the one or more nucleotide sequences encoding the one or more amino acid sequences, the first codon of the fragment of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) the fragment of the nucleic acid residues of exon 6 of SMN comprises any number of nucleotides of exon 6 of SMN so long as in the mRNA transcript transcribed from the nucleic acid construct the first codon of the fragment of the nucleic acid residues of exon 6 of SMN and the first codon of the fragment of the nucleic acid residues of exon 8 of SMN are in frame with each other; and (iii) the fragment of the nucleic acid residues of exon 7 of SMN comprises a minimum of the nucleotides of exon 7 of SMN required for splicing and in the mRNA transcript transcribed from the nucleic acid construct the first start codon and the stop codon upstream of the reporter gene coding sequence are in the same contiguous open reading frame without any interruption by, e.g., a stop codon. In some embodiments, in the mRNA transcript transcribed from the nucleic acid construct, the regions of the mRNA transcript corresponding to the fragments of the nucleic acid residues of exon 6 and exon 7 of SMN do not contain a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In certain embodiments, an internal start codon (e.g., ATG) in the nucleic acid residues of exon 6 of SMN or a fragment thereof is used as a start codon for the nucleic acid construct. In some embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequences (e.g., peptides or polypeptides), wherein said one or more nucleotide sequences are upstream (5') of the nucleic acid residues of exon 6 of SMN or a fragment thereof, and wherein the first codon of each of the one or more nucleotide sequences. In some embodiments, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (c) a fragment of the nucleic acid residues of exon 7 of SMN; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) the fragment of the nucleic acid residues of exon 6 of SMN comprises a minimum of the nucleotides of exon 6 of SMN required for splicing so long as in the mRNA transcript transcribed from the nucleic acid construct the first start codon and the stop codon upstream of the reporter gene coding sequence are in the same contiguous open reading frame without any interruption by, e.g., a stop codon; and (iii) the fragment of the nucleic acid residues of exon 7 of SMN comprises a minimum of the nucleotides of exon 7 of SMN required for splicing so long as in the mRNA transcript transcribed from the nucleic acid construct the first start codon and the stop codon upstream of the reporter gene coding sequence are in the same contiguous open reading frame without any interruption by, e.g., a stop codon. In certain embodiments, the first codon of the nucleic acid residues of exon 6 of SMN or fragment thereof, the first codon of the fragment of the nucleic acid residues of exon 7 of SMN and the first codon of the fragment of the nucleic acid residues of exon 8 of SMN are in frame with each other. In some embodiments, in the mRNA transcript transcribed from the nucleic acid construct, the regions of the mRNA transcript corresponding to the fragments of the nucleic acid residues of exon 6 and exon 7 of SMN do not contain a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In certain embodiments, the fragment of the nucleic acid residues of exon 6 of SMN comprises a minimum of the first two nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) of the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequences (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In some embodiments, the first codon of the nucleic acid residues of exon 6 of SMN or a fragment thereof, the first codon of the fragment of the nucleic acid residues of exon 7 of SMN, and the first codon of the fragment of exon 8 of SMN are in frame with each other in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon. In some embodiments the first codon of the nucleic acid residues of exon 7 of SMN, and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 7 of SMN, and wherein the first codon of each of the one or more nucleotide sequences, the first codon of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) a fragment of the nucleic acid residues of exon 8 of SMN; and (d) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct the first start codon and the stop codon upstream of the reporter gene coding sequence are in the same contiguous open reading frame without any interruption by, e.g., a stop codon; and (iii) the fragment of the nucleic acid residues of exon 6 of SMN comprises any number of nucleotides of exon 6 of SMN so long as in the mRNA transcript transcribed from the nucleic acid construct in the mRNA transcript transcribed from the nucleic acid construct the first start codon and the stop codon upstream of the reporter gene coding sequence are in the same contiguous open reading frame without any interruption by, e.g., a stop codon. In some embodiments, in the mRNA transcript transcribed from the nucleic acid construct, the regions of the mRNA transcript corresponding to the fragment of the nucleic acid residues of exon 6 of SMN and the nucleic acid residues of exon 7 of SMN do not contain a stop codon. In some embodiments, the first codon of the nucleic acid residues of exon 6 of SMN or a fragment thereof, the first codon of the nucleic acid residues of exon 7 of SMN, and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon. In some embodiments, the first codon of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 7 of SMN, and wherein the first codon of each of the one or more nucleotide sequences, the first codon of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (ii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In certain embodiments, an internal start codon (e.g., an ATG) of the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 of SMN required for a functional, minimum intron; (c) the nucleic acid residues of exon 7 of SMN, wherein any number of nucleotides are inserted after the 48th nucleotide residue from the 5' end of exon 7 of SMN (i.e., before the 6th nucleotide from the 3' end of exon 7 of SMN) as long as the native stop codon of exon 7 of SMN is inactivated and any additional stop codon is not generated; (d) the nucleic acid residues of intron 7 of SMN or a fragment thereof, wherein the fragment of the nucleic acid residues of intron 7 comprises any number of nucleotides of intron 7 of SMN required for a functional, minimum intron; (e) a fragment of the nucleic acid residues of exon 8 of SMN; and (f) a reporter gene coding sequence lacking a start codon, wherein: (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the open reading frames of the reporter gene coding sequence and the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); and (iii) in the mRNA transcript transcribed from the nucleic acid construct the first start codon and the stop codon upstream of the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, a single nucleotide residue is inserted after the 48th nucleotide residue from the 5' end of exon 7 of SMN (i.e., before the 6th nucleotide from the 3' end of exon 7 of SMN). In certain embodiments, the fragment of the nucleic acid residues of exon 6 of SMN comprises a minimum of the first three nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) of the nucleic acid residues of exon 6 of SMN or a fragment thereof is used as a start codon for the nucleic acid construct. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, the first codon of the nucleic acid residues of exon 7 of SMN, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of the nucleic acid residues of intron 7 comprises any number of nucleotides of intron 7 of SMN required for a functional, minimum intron; (d) a fragment of the nucleic acid residues of exon 8 of SMN; and (e) a reporter gene coding sequence lacking a start codon, wherein: (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct and there is a stop codon in the region of the mRNA transcript corresponding to the fragment of the nucleic acid residues of exon 8 of SMN (i.e., upstream of the reporter gene coding sequence); (ii) in the mRNA transcript transcribed from the nucleic acid construct, the first start codon and the stop codon upstream of the reporter gene coding sequence are in the same contiguous open reading frame without any interruption by, e.g., a stop codon. In some embodiments, the first codon of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 7 of SMN, and wherein the first codon of each of the one or more nucleotide sequences, the first codon of the nucleic acid residues of exon 7 of SMN, and the first codon of the fragment of the nucleic acid residues of exon 8 of SMN are in frame with one another in the mRNA transcript transcribed from the nucleic acid construct. In accordance with such embodiments, the first start codon and the stop codon upstream of the reporter gene coding sequence in the mRNA transcript are in the same contiguous open reading frame without any interruption by, e.g., a stop codon.

In another embodiment, a nucleic acid construct comprises, in 5' to 3' order: (a) the nucleic acid residues of exon 6 of SMN or a fragment thereof; (b) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (c) the nucleic acid residues of intron 7 of SMN or a fragment thereof, wherein the fragment of intron 7 of SMN comprises any number of nucleotides of intron 7 of SMN required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In some embodiments, the first codon of the nucleic acid residues of exon 6 of SMN or a fragment thereof, the first codon of the nucleic acid residues of exon 7 of SMN, and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, the first codon of the nucleic acid residues of exon 7 of SMN, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of intron 6 of SMN comprises any number of nucleotides of intron 6 required for a functional, minimum intron; (c) the nucleic acid residues of exon 7 of SMN, wherein a single guanine residue is inserted after the 48th nucleotide residue from the 5' end of exon 7 of SMN (i.e., before the 6th nucleotide from the 3' end of exon 7 of SMN); (d) the nucleic acid residues of intron 7 of SMN or a fragment thereof, wherein the fragment of intron 7 of SMN comprises any number of nucleotides of intron 7 of SMN required for a functional, minimum intron; (e) a fragment of the nucleic acid residues of exon 8 of SMN; and (f) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the fragment of the nucleic acid residues of exon 6 of SMN comprises a minimum of the first two nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof. In some embodiments, the nucleic acid construct comprises one or more nucleotide sequences encoding one or more amino acid sequence (e.g., peptides or polypeptides), wherein said one or more nucleotide sequences are upstream (5') of the nucleic acid residues of exon 6 of SMN or a fragment thereof, and wherein the first codon of each of the one or more nucleotide sequences, the first codon of the nucleic acid residues of exon 6 of SMN or a fragment thereof, the first codon of the nucleic acid residues of exon 7 of SMN, and the first codon of the fragment of the nucleic acid residues of exon 8 of SMN are in frame with one another in the mRNA transcript transcribed from the nucleic acid construct. In certain embodiments, the one or more nucleotide sequences encoding amino acid sequences (e.g., peptides or polypeptides) upstream of the nucleic acid residues of exon 6 of SMN or a fragment thereof contains a start codon. In accordance with such embodiments, the first start codon and the stop codon upstream of the reporter gene coding sequence in the mRNA transcript are in the same contiguous open reading frame.

In another embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In some embodiments, the first codon of the fragment of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the minimum of one nucleotide.

In another embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN), wherein a single guanine residue is inserted into the fragment of the nucleic acid residues of exon 7 of SMN at the location that corresponds to the location in exon 7 of SMN that is after the 48th nucleotide from the 5' end of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the fragment of the nucleic acid residues of exon 7 of SMN.

In a specific embodiment, a nucleic acid construct comprises, in 5' to 3' order: (a) a start codon; (b) a minimum of one nucleotide; (c) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN) and wherein a single guanine residue is inserted upstream (5') of the fragment of the nucleic acid residues of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the minimum of one nucleotide.

In a specific embodiment, a nucleic acid construct comprises, in 5' to 3' order: (a) a start codon; (b) a fragment of the nucleic acid residues of exon 7 of SMN, wherein the fragment of the nucleic acid residues of exon 7 of SMN consists of the first six nucleotides from the 3' end of exon 7 of SMN (i.e., nucleotide residues 49 to 54 from the 5' end of exon 7 of SMN), wherein a single guanine residue is inserted upstream (5') of the fragment of the nucleic acid residues of exon 7 of SMN, and wherein the fragment of the nucleic acid residues of exon 7 of SMN comprises any number of nucleotides of exon 7 required for splicing; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon of the fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In some embodiments, the first codon of the fragment of the nucleic acid residues of exon 7 of SMN and the first codon of the fragment of exon 8 of SMN are in frame with each other in the mRNA transcript transcribed from the nucleic acid construct. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, the nucleic acid construct comprises a start codon upstream (5') to the fragment of the nucleic acid residues of exon 7 of SMN.

In another embodiment, a nucleic acid construct comprises, in 5' to 3' order: (a) the nucleic acid residues of exon 6 of SMN or a fragment thereof; (b) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (c) the nucleic acid residues of intron 7 of SMN or a fragment thereof, wherein the fragment of the nucleic acid residues of intron 7 of SMN comprises any number of nucleotides of intron 7 required for a functional, minimum intron; (d) a fragment of the nucleic acid residues of exon 8 of SMN; and (e) a reporter gene coding sequence lacking a start codon, wherein (i) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (ii) the production of the mRNA transcript generates a stop codon in the region of the mRNA transcript that corresponds to the fragment of the nucleic acid residues of exon 8 of SMN (i.e., upstream of the reporter gene coding sequence); and (iii) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In certain embodiments, an internal start codon (e.g., an ATG) in the nucleic acid residues of exon 6 of SAM or a fragment thereof is used as a start codon for the nucleic acid construct. In some embodiments, the nucleic acid construct comprises a start codon upstream (5') of the nucleic acid residues of exon 6 of SMN or a fragment thereof.

In another embodiment, a nucleic acid construct comprises, in 5' to 3' order: (a) the nucleic acid residues of exon 6 of SMN or a fragment thereof; (b) the nucleic acid residues of intron 6 of SMN or a fragment thereof, wherein the fragment of the nucleic acid residues of SMN comprises any number of nucleotides of intron 6 of SMN for a functional, minimum intron; (c) a fragment of the nucleic acid residues of exon 7 of SMN, wherein the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN) and wherein a single guanine residue is inserted into the fragment of the nucleic acid residues of exon 7 of SMN at the location that corresponds to the location in exon 7 of SMN that is after the 48th nucleotide from the 5' end of exon 7 of SMN; (d) the nucleic acid residues of intron 7 of SMN or a fragment thereof, wherein the fragment of the nucleic acid residues of intron 7 of SMN comprises any number of nucleotides of intron 7 required for a functional, minimum intron; (e) a fragment of the nucleic acid residues of exon 8 of SMN; and (f) a reporter gene coding sequence lacking a start codon, wherein (i) the fragment of the nucleic acid residues of exon 6 of SMN comprises a minimum of the nucleotides of exon 6 of SMN required for splicing; (ii) the reporter gene coding sequence is fused to the fragment of the nucleic acid residues of exon 8 of SMN such that the first codon of the reporter gene coding sequence and the first codon fragment are out of frame with each other in the mRNA transcript transcribed from the nucleic acid construct; (iii) the production of the mRNA transcript generates a stop codon in the region of the mRNA transcript that corresponds to the fragment of the nucleic acid residues of exon 8 of SMN (i.e., upstream of the reporter gene coding sequence); and (iv) in the mRNA transcript transcribed from the nucleic acid construct, the first start codon and the stop codon upstream from the reporter gene coding sequence are in the same contiguous open reading frame without any interruption by, e.g., a stop codon. In a specific embodiment, the first codon of the fragment of the nucleic acid residues of exon 8 of SMN and the first codon of the reporter gene coding sequence are out of frame with each other by one nucleotide in the mRNA transcript transcribed from the nucleic acid construct. In one embodiment, the fragment of the nucleic acid residues of exon 8 of SMN consists of the first 21 nucleotides from the 5' end of exon 8 of SMN. In another embodiment, the fragment of the nucleic acid residues of exon 8 of SMN consists of the first 23 nucleotides from the 5' end of exon 8 of SMN. In a specific embodiment, the fragment of the nucleic acid residues of exon 7 of SMN comprises a minimum of the first nucleotide from the 5' end of exon 7 of SMN and the first two nucleotides from the 3' end of exon 7 of SMN (i.e., nucleotide residues 53 and 54 from the 5' end of exon 7 of SMN). In another specific embodiment, the fragment of the nucleic acid residues of exon 7 of SMN comprises a minimum of the first two or six nucleotides from the 3' end of exon 7 of SMN (i.e., nucleotide residues 49 to 54 from the 5' end of exon 7 of SMN). In another specific embodiment, the fragment of the nucleic acid residues of exon 7 of SMN comprises a minimum of the first six nucleotides from the 3' end of exon 7 of SMN (i.e., nucleotide residues 49 to 54 from the 5' end of exon 7 of SMN). In certain embodiments, the fragment of exon 6 of SMN comprises a minimum of the first two nucleotides from the 3' end of exon 6 of SMN. In other embodiments, the fragment of exon 6 of SMN comprises a minimum of the first three nucleotides from the 3' end of exon 6 of SMN. In certain embodiments, an internal start codon (e.g., an ATG) in the nucleic acid residues of exon 6 of SMN or a fragment thereof is used as a start codon for the nucleic acid construct. In other embodiments, the nucleic acid construct comprises a start codon upstream (5') to the nucleic acid residues of exon 6 of SMN or a fragment thereof.

In certain embodiments, the term "a functional, minimum intron" in the context of a fragment of the nucleic acid residues of intron 6 of SMN or a fragment of the nucleic acid residues of intron 7 of SMN refers to a fragment that comprises at least six nucleotides of the 5' splice site of intron 6 or intron 7 of SMN and three nucleotides plus the polypyrimidine tract and the branch-point sequence of the 3' splice site of intron 6 or intron 7 of SMN. In one embodiment, the fragment comprises the minimal number of nucleic acids required for an intron to permit the retention of the nucleotides of the exons flanking the intron after splicing. In one embodiment, the 3' splice site plus the polypyrimidine tract and the branch-point sequence of the 3' splice comprises about 40 nucleic acid residues of the 3' splice site of intron 6 or intron 7 of SMN. In another embodiment, the 3' splice site plus the polypyrimidine tract and the branch-point sequence of the 3' splice comprises 20 nucleic acid residues of the 3' splice site of intron 6 or intron 7 of SMN.

In certain embodiments, the term "minimum of the nucleotides of exon 6 of SMN required for splicing" refers to a fragment of exon 6 of SMN that permits removal of an intron via mRNA splicing and maintains the complete sequence of the mRNA fragment included (or encoded) in a nucleic acid construct. In a specific embodiment, the fragment includes the intact 3' end of exon 6 of SMN. In another embodiment, the fragment of exon 6 of SMN is at least 3, at least 6, at least 9, or at least 12 nucleic acids long. In a specific embodiment, the intact 3' end of the fragment of exon 6 of SMN at least 6, at least 9, or at least 12 nucleic acids long.

In certain embodiments, the term "minimum of the nucleotides of exon 7 of SMN required for splicing" refers to a fragment of exon 7 of SMN that permits removal of an intron via mRNA splicing and maintains the complete sequence of the mRNA fragment included (or encoded) in a nucleic acid construct.

In certain aspects of the invention, an RNA transcript transcribed from a nucleic acid construct described above is utilized in the cell-based and cell-free screening assays to identify or validate compounds that modulate ribosomal frameshifting (e.g., programmed ribosomal frameshifting). Techniques for the production of an RNA transcript (e.g., a pre-mRNA transcript or a mRNA transcript) from a nucleic acid construct are known o one of skill in the art. For example, a mRNA transcript can be produced in a run-off transcription of a linearized form of a nucleic acid construct described herein. In a specific embodiment, the nucleic acid constructs described herein comprise bacteriophage promoters (e.g., a T3, SP6 or T7 bacteriophage promoter) or any other suitable promoter that may be used together with the respective RNA polymerase derived from the corresponding bacteriophage. Techniques for performing run-off transcription are well-known in the art. In a specific embodiment, a mRNA transcript transcribed from a nucleic acid construct described above is utilized in the cell-based and cell-free screening assays to identify or validate compounds that modulate programmed ribosomal frameshifting.

In certain embodiments, a nucleic acid construct described herein is isolated. In some embodiments, an RNA transcript (e.g., a pre-mRNA or mRNA transcript) described herein is isolated.

Screening Assays

Cell-Based Assays

In one aspect, the present invention provides a method for the identification or validation of a compound that modulates ribosomal frameshifting comprising: (a) contacting a compound with a host cell containing a nucleic acid construct described herein; and (b) detecting the activity of a fusion protein expressed from the nucleic acid construct. A compound that increases/causes ribosomal frameshifting will result in an increase in the activity of the fusion protein expressed by the host cell compared with (i) the activity of the fusion protein expressed by the host cell in the absence of the compound, (ii) the activity of the fusion protein expressed by the host cell in the presence of a negative control, and/or (iii) against a previously determined reference range for a negative control. In a specific embodiment, the increase in the activity of the fusion protein is a statistically significant increase. In contrast, a compound that does not modulate or decreases ribosomal frameshifting will not increase or not statistically significantly increase the level of activity of the fusion protein expressed by the host cell compared to (i) the level of activity of the fusion protein expressed by the host cell in the absence of the compound, (ii) the level of activity of fusion protein expressed by the host cell in the presence of a negative control, and/or (iii) a previously determined reference range for a negative control.

In some embodiments, in addition to, or as an alternative to, detecting the activity of a fusion protein expressed from the nucleic acid construct, the amount of the fusion protein can be detected. In accordance with such embodiments, an increase in the amount of the fusion protein expressed by the host cell in the presence of the compound when compared to (i) a previously determined reference range for a negative control, (ii) the amount of the fusion protein expressed by the host cell in the absence of the compound in such an assay, and/or (iii) the amount of the fusion protein expressed by the host cell in the presence of a negative control in such an assay indicates that a particular compound increases ribosomal frameshifting. In a specific embodiment, the increase in the amount of the fusion protein is a statistically significant increase. In contrast, a compound that does not modulate ribosomal frameshifting will not increase or not statistically significantly increase the amount of the fusion protein expressed by the host cell compared to (i) the amount of the fusion protein expressed by the host cell in the absence of the compound, (ii) the amount of fusion protein expressed by the host cell in the presence of a negative control, and/or (iii) a previously determined reference range for a negative control.

In certain embodiments, a method for the identification or validation of a compound that modulates ribosomal frameshifting does not use a nucleic acid construct described in Zhang, et al., 2001, *Gene Therapy*, 8:1532-1538 (e.g., the nucleic acid construct in FIG. 1 of Zhang, et al., 2001, *Gene Therapy* 8: 1532-1538).

In another aspect, the present invention provides a method for the identification or validation of a compound that modulates the efficiency of programmed ribosomal frameshifting comprising: (a) contacting a compound with a host cell containing a nucleic acid construct described herein; and (b) detecting the activity of a fusion protein expressed from the nucleic acid construct. A compound that modulates the efficiency of programmed ribosomal frameshifting will result in an increase in the activity of the fusion protein expressed by the host cell compared with (i) the activity of the fusion protein expressed by the host cell in the absence of the compound, (ii) the activity of the fusion protein expressed by the host cell in the presence of a negative control, and/or (iii) against a previously determined reference range for a negative control. In a specific embodiment, the increase in the activity of the fusion protein is a statistically significant increase. In contrast, a compound that does not modulate the efficiency of programmed ribosomal frameshifting will not increase or not statistically significantly increase the level of activity of the fusion protein expressed by the host cell compared to (i) the level of activity of the fusion protein expressed by the host cell in the absence of the compound, (ii) the level of activity of fusion protein expressed by the host cell in the presence of a negative control, and/or (iii) a previously determined reference range for a negative control.

In some embodiments, in addition to, or as an alternative to, detecting the activity of a fusion protein expressed from the nucleic acid construct, the amount of the fusion protein can be detected. In accordance with such embodiments, an increase in the amount of the fusion protein expressed by the host cell in the presence of the compound when compared to (i) a previously determined reference range for a negative control, (ii) the amount of the fusion protein expressed by the host cell in the absence of the compound in such an assay, and/or (iii) the amount of the fusion protein expressed by the host cell in the presence of a negative control in such an assay indicates that a particular compound modulates the efficiency of programmed ribosomal frameshifting. In a specific embodiment, the increase in the amount of the fusion protein is a statistically significant increase. In contrast, a compound that does not modulate the efficiency of programmed ribosomal frameshifting will not increase or not statistically significantly increase the amount of the fusion protein expressed by the host cell compared to (i) the amount of the fusion protein expressed by the host cell in the absence of the compound, (ii) the amount of fusion protein expressed by the host cell in the presence of a negative control, and/or (iii) a previously determined reference range for a negative control.

In one embodiment, a method for identifying or validating a compound that modulates the efficiency of programmed ribosomal frameshifting comprises: (a) expressing in a host cell a nucleic acid construct described herein; (b) contacting said host cell with a compound; and (c) detecting the activity or amount of a fusion protein encoded by the nucleic acid construct, wherein a compound that modulates the efficiency of programmed ribosomal frameshifting is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In a specific embodiment, a method for identifying or validating a compound that modulates ribosomal frameshifting comprises: (a) contacting a compound with a host cell expressing a nucleic acid construct described in Zhang, et al., 2001, *Gene Therapy*, 8:1532-1538 (e.g., the nucleic acid construct in FIG. 1 of Zhang, et al., 2001, *Gene Therapy* 8: 1532-1538); and (b) detecting the activity or amount of a fusion protein encoded by the nucleic acid construct, wherein a compound that modulates ribosomal frameshifting is identified or validated if the activity or amount of the fusion protein detected in the presence of the compound is increased relative to the activity or amount of the fusion protein detected in the presence of a negative control (e.g., 0.005%-1% DMSO). In a specific embodiment, an increase in the activity or amount of the fusion protein is a statistically significant increase.

In another specific embodiment, a method for identifying or validating a compound that modulates the efficiency of programmed ribosomal frameshifting comprises: (a) contacting a compound with a host cell expressing a nucleic acid construct described in Zhang, et al., 2001, *Gene Therapy*, 8:1532-1538 (e.g., the nucleic acid construct in FIG. 1 of Zhang, et al, 2001, *Gene Therapy* 8: 1532-1538); and (b) detecting the activity or amount of a fusion protein encoded by the nucleic acid construct, wherein a compound that modulates the efficiency of programmed ribosomal frameshifting is identified or validated if the activity or amount of the fusion protein detected in the presence of the compound is increased relative to the activity or amount of the fusion protein detected in the presence of a negative control (e.g., 0.005%-1% DMSO). In a specific embodiment, an increase in the activity or amount of the fusion protein is a statistically significant increase.

In certain embodiments, a method for identifying or validating a compound that modulates the efficiency of programmed ribosomal frameshifting does not comprise: (a) contacting a compound with a host cell expressing a nucleic acid construct described in Zhang, et al., 2001, *Gene Therapy*, 8:1532-1538 (e.g., the nucleic acid construct in FIG. 1 of Zhang, et al., 2001, *Gene Therapy* 8: 1532-1538); and (b) detecting the activity or amount of a fusion protein by the nucleic acid construct, wherein a compound that modulates the efficiency of programmed ribosomal frameshifting is identified or validated if the activity or amount of the fusion protein detected in the presence of the compound is increased relative to the activity or amount of the fusion protein detected in the presence of a negative control (e.g., 0.005%-1% DMSO).

In another aspect, the invention provides a method for identifying or validating a compound that modulates the efficiency of programmed ribosomal frameshifting comprising: (a) contacting a compound with a host cell engineered to contain a pre-mRNA or mRNA transcript transcribed from a nucleic acid construct described herein; and (b) detecting the activity or amount of a fusion protein translated from the pre-mRNA or mRNA transcript, wherein a compound that modulates the efficiency of programmed ribosomal frameshifting is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In one embodiment, the invention provides a method for identifying or validating a compound that modulates the efficiency of programmed ribosomal frameshifting comprising: (a) transfecting into a cell a RNA transcript (e.g., pre-mRNA or mRNA transcript) transcribed from a nucleic acid construct described herein; (b) contacting said host cell with a compound; and (c) detecting the activity or amount of a fusion protein translated from the RNA transcript, wherein a compound that modulates the efficiency of programmed ribosomal frameshifting is identified or validated if the activity or amount of the fusion protein expressed by the host cell in the presence of a compound is increased relative to a previously determined reference range for a negative control, or relative to the activity or amount of the fusion protein expressed by the host cell in the absence of said compound or the presence of a negative control (e.g., PBS or DMSO). In a specific embodiment, an increase in the activity or amount of the fusion protein is a statistically significant increase.

In a specific embodiment, a method for identifying or validating a compound that modulates the efficiency of programmed ribosomal frameshifting comprises: (a) contacting a compound with a host cell engineered to contain a RNA transcript (e.g., pre-mRNA or mRNA transcript) transcribed from a nucleic acid construct described in Zhang, et al., 2001, *Gene Therapy*, 8:1532-1538 (e.g., the nucleic acid construct in FIG. 1 of Zhang, et al., 2001, *Gene Therapy* 8: 1532-1538); and (b) detecting the activity or amount of a fusion protein translated from the RNA transcript, wherein a compound that modulates the efficiency of programmed ribosomal frameshifting is identified or validated if the activity or amount of the fusion protein detected in the presence of the compound is increased relative to the activity or amount of the fusion protein detected in the presence of a negative control (e.g., 0.005%-1% DMSO). In a specific embodiment, an increase in the activity or amount of the fusion protein is a statistically significant increase.

In a specific embodiment, a method for identifying or validating a compound that modulates the efficiency of programmed ribosomal frameshifting does not comprise: (a) contacting a compound with a host cell engineered to contain a RNA transcript (e.g., pre-mRNA or mRNA transcript) transcribed from a nucleic acid construct described in Zhang, et al., 2001, *Gene Therapy*, 8:1532-1538 (e.g., the nucleic acid construct in FIG. 1 of Zhang, et al., 2001, *Gene Therapy* 8: 1532-1538); and (b) detecting the activity or amount of a fusion protein translated from the RNA transcript, wherein a compound that modulates the efficiency of programmed ribosomal frameshifting is identified or validated if the activity or amount of the fusion protein detected in the presence of the compound is increased relative to the activity or amount of the fusion protein detected in the presence of a negative control (e.g., 0.005%-1% DMSO).

The step of contacting a compound with a host cell containing the nucleic acid construct or RNA transcript may be conducted under conditions approximating or mimicking physiologic conditions. In a specific embodiment, a compound is added to the cells in the presence of an appropriate growth medium for said cells. In another embodiment, a compound is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but are not limited to, KCl, NaCl, and/or $MgCl_2$. The optimal concentration of each salt used in the aqueous solution is dependent on the host cells and compounds used and can be determined using routine experimentation.

A compound is contacted with a host cell containing the nucleic acid construct or RNA transcript for a specific period of time. For example, the compound may be contacted with the host cell containing the nucleic acid construct or RNA transcript for a time period of about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In a specific embodiment, contact is over a time period of about 12 hours to 15 hours, i.e., overnight.

In specific embodiments, a negative control (e.g., DMSO at 0.005-1.0%, or PBS, or another agent that is known to have no effect on the expression of the fusion protein) and a positive control (e.g., an agent that modulates the efficiency of programmed ribosomal frameshifting) are included in the cell-based assays described herein.

The amount or activity of a fusion protein described herein may be detected by any technique well-known to one of skill in the art. For example, techniques well-known to one of skill in the art for detecting reporter proteins can be used to detect either or both the amount or activity of fusion proteins. Methods for detecting the amount or activity of a reporter protein will vary with the reporter gene used. Assays for the various reporter genes are well-known to one of skill in the art.

Cell-Free Assays

In one aspect, the present invention provides a method for the identification or validation of a compound that modulates ribosomal frameshifting comprising: (a) contacting a compound with a cell-free extract and a RNA transcript (e.g., mRNA or pre-mRNA) which is transcribed from a nucleic acid construct described herein; and (b) detecting the amount or activity of the fusion protein translated from the RNA. A compound that increases/causes ribosomal frameshifting will result in an increase in the amount or activity of the fusion protein translated from the RNA compared with (i) the amount or activity of the fusion protein translated from the RNA in the absence of the compound, (ii) the amount or activity of the fusion protein translated from the RNA in the presence of a negative control, and/or (iii) against a previously determined reference range for a negative control. In a specific embodiment, the increase in the amount or activity of the fusion protein is a statistically significant increase. In contrast, a compound that does not modulate or decreases ribosomal frameshifting will not increase or not statistically significantly increase the amount or activity of the fusion protein translated from the RNA compared to (i) the amount or activity of the fusion protein translated from the RNA in the absence of the compound, (ii) the amount or activity of the fusion protein translated from the RNA in the presence of a negative control, and/or (iii) against a previously determined reference range for a negative control.

In one embodiment, the present invention provides a method for identifying or validating a compound that modulates ribosomal frameshifting comprising: (a) contacting a compound with a cell-free extract and a RNA transcript (e.g., mRNA or pre-mRNA) which is transcribed from a nucleic acid construct described herein; and (b) detecting the amount or activity of the fusion protein translated from the RNA, wherein a compound that increases ribosomal frameshifting is identified or validated if the amount or activity of the fusion protein detected in the presence of the compound is increased relative to the amount or activity of the fusion protein detected in the absence of the compound or presence of a negative control (e.g., DMSO, PBS and the like), or relative to a previously determined reference range that is the amount or activity of the fusion protein obtained for a negative control. In a specific embodiment, the increase in the activity or amount of the fusion protein is a statistically significant change.

In another embodiment, a method for identifying or validating a compound that modulates ribosomal frameshifting comprises: (a) contacting a compound with a cell-free extract and a RNA transcript (e.g., a pre-mRNA or mRNA transcript) which is transcribed from a nucleic acid construct described in Zhang, et al., 2001, *Gene Therapy*, 8:1532-1538 (e.g., the nucleic acid construct in FIG. 1 of Zhang, et al., 2001, *Gene Therapy*, 8:1532-1538); and (b) detecting the activity or amount of a fusion protein translated from the RNA transcript, wherein a compound that modulates ribosomal frameshifting is identified or validated if the activity or amount of the fusion protein detected in the presence of a compound is increased relative to activity or amount of the fusion protein detected in the presence of a negative control (e.g., 0.005%-1% DMSO). In a specific embodiment, the increase in the activity or amount of the fusion protein is a statistically significant increase.

In another aspect, the present invention provides a method for identifying or validating a compound that modulates the efficiency of programmed ribosomal frameshifting comprising: (a) contacting a compound with a cell-free extract and a RNA transcript (e.g., mRNA or pre-mRNA) which is transcribed from a nucleic acid construct described herein; and (b) detecting the amount or activity of the fusion protein translated from the RNA, wherein a compound that modulates the efficiency of programmed ribosomal frameshifting is identified or validated if the amount or activity of the fusion protein detected in the presence of the compound is increased relative to the amount or activity of the fusion protein detected in the absence of the compound or presence of a negative control (e.g., DMSO, PBS and the like), or relative to a previously determined reference range that is the amount or activity of the fusion protein obtained for a negative control. In a specific embodiment, the increase in the activity or amount of the fusion protein is a statistically significant change.

Typically, the RNA transcript (e.g., mRNA or pre-mRNA) used in the cell-free assay described herein is one that has been produced using, e.g., in vitro run-off transcription. For example, a RNA can be made in run-off transcription of a linearized form of a nucleic acid construct described herein. Bacteriophage promoters from a T3, SP6 or T7 bacteriophage or any other suitable promoter may be used together with the respective RNA polymerase derived from the corresponding bacteriophage.

In another embodiment, a method for identifying or validating a compound that modulates the efficiency of programmed ribosomal frameshifting comprises: (a) contacting a compound with a cell-free extract and a RNA transcript (e.g., a pre-mRNA or mRNA transcript) which is transcribed from a nucleic acid construct described in Zhang, et al., 2001, *Gene Therapy*, 8:1532-1538 (e.g., the nucleic acid construct in FIG. 1 of Zhang, et al., 2001, *Gene Therapy*, 8:1532-1538); and (b) detecting the activity or amount of a fusion protein translated from the RNA transcript, wherein a compound that modulates the efficiency of programmed ribosomal frameshifting is identified or validated if the activity or amount of the fusion protein detected in the presence of a compound is increased relative to activity or amount of the fusion protein detected in the presence of a negative control (e.g., 0.005%-1% DMSO). In a specific embodiment, the increase in the activity or amount of the fusion protein is a statistically significant increase.

In certain embodiments, a method for the identification or validation of a compound that modulates ribosomal frameshifting does not use a cell-free extract and a RNA transcript (e.g., a pre-mRNA or mRNA transcript) which is transcribed from a nucleic acid construct described in Zhang, et al., 2001, *Gene Therapy*, 8:1532-1538 (e.g., the nucleic acid construct in FIG. 1 of Zhang, et al., 2001, *Gene Therapy*, 8:1532-1538).

In some embodiments, a method for identifying or validating a compound that modulates the efficiency of programmed ribosomal frameshifting does not comprise: (a) contacting a compound with a cell-free extract and a RNA transcript (e.g., a pre-mRNA or mRNA transcript) which is transcribed from a nucleic acid construct described in Zhang, et al., 2001, *Gene Therapy*, 8:1532-1538 (e.g., the nucleic acid construct in FIG. 1 of Zhang, et al., 2001, *Gene Therapy*, 8:1532-1538); and (b) detecting the activity or amount of a fusion protein translated from the RNA transcript, wherein a compound that modulates the efficiency of programmed ribosomal frameshifting is identified or validated if the activity or amount of the fusion protein detected in the presence of a compound is increased relative to activity or amount of the fusion protein detected in the presence of a negative control (e.g., 0.005%-1% DMSO).

In another aspect, the present invention provides a method for identifying or validating a compound that modulates the efficiency of programmed ribosomal frameshifting comprising: (a) contacting a compound with a cell-free extract and a nucleic acid construct described herein; and (b) detecting the amount or activity of the fusion protein expressed from the nucleic acid construct, wherein a compound that modulates the efficiency of programmed ribosomal frameshifting is identified or validated if the amount or activity of the fusion protein detected in the presence of the compound is increased relative to the amount or activity of the fusion protein detected in the absence of the compound or presence of a negative control (e.g., DMSO, PBS and the like), or relative to a previously determined reference range that is the amount or activity of the fusion protein obtained for a negative control. In accordance with this aspect, the cell-free extract used comprises components necessary for in vitro transcription, splicing, and translation. In a specific embodiment, the increase in the activity or amount of the fusion protein is a statistically significant increase.

In one embodiment, a method for identifying or validating a compound that modulates the efficiency of programmed ribosomal frameshifting comprises: (a) contacting a compound with a cell-free extract and a nucleic acid construct described in Zhang, et al., 2001, *Gene Therapy*, 8:1532-1538 (e.g., the nucleic acid construct in FIG. 1 of Zhang, et al., 2001, *Gene Therapy*, 8:1532-1538); and (b) detecting the activity or amount of a fusion protein expressed from the nucleic acid construct, wherein a compound that modulates the efficiency of programmed ribosomal frameshifting is identified or validated if the activity or amount of the fusion protein detected in the presence of a compound is increased relative to activity or amount of the fusion protein detected in the presence of a negative control (e.g., 0.005%4% DMSO). In accordance with this embodiment, the cell-free extract used comprises components necessary for in vitro transcription, splicing, and translation. In a specific embodiment, the increase in the activity or amount of the fusion protein is a statistically significant increase.

In some embodiments, a method for identifying or validating a compound that modulates the efficiency of programmed ribosomal frameshifting does not comprise: (a) contacting a compound with a cell-free extract and a nucleic acid construct described in Zhang, et al., 2001, *Gene Therapy*, 8:1532-1538 (e.g., the nucleic acid construct in FIG. 1 of Zhang, et al, 2001, *Gene Therapy*, 8:1532-1538); and (b) detecting the activity or amount of a fusion protein expressed from the nucleic acid construct, wherein a compound that modulates the efficiency of programmed ribosomal frameshifting is identified or validated if the activity or amount of the fusion protein detected in the presence of a compound is increased relative to activity or amount of the fusion protein detected in the presence of a negative control (e.g., 0.005%-1% DMSO).

The step of contacting a compound with a cell-free extract and a RNA transcript or a nucleic acid construct as described herein may be conducted under conditions approximating or mimicking physiologic conditions. In a specific embodiment, a compound is added to the cell-free extract and nucleic acid construct or RNA transcript in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cell-free extract and compounds used and can be determined using routine experimentation. A compound may be contacted with a cell-free extract and a RNA transcript or a nucleic acid construct for a specific period of time. For example, a compound may be contacted with a cell-free extract and a RNA transcript or a nucleic acid construct for a time period of about 2 minutes, 5 minutes, 10 minutes, 15 minutes, 20 minutes, 30 minutes, 45 minutes, 1 hour, 2 hours, 3 hours, 4 hours, 8 hours, 10 hours, 12 hours, 14 hours, 16 hours, 18 hours or 24 hours. In some embodiments, the compound is contacted with a cell-free containing a RNA transcript or a nucleic acid construct for a time period in a range of from about 1 minute to about 2 hours, from about 1 minute to about 1 hour, from about 1 minute to about 45 minutes, from about 1 minute to about 30 minutes, or from about 1 minute to about 15 minutes In specific embodiments, a negative control (e.g., DMSO at 0.005-1.0%, or PBS, or another agent that is known to have no effect on the expression of the fusion protein) and a positive control (e.g., an agent that modulates the efficiency of programmed ribosomal frameshifting) are included in the cell-free assays described herein.

Host Cells, Cell-Free Extracts, and Reporter Genes

Techniques for the production or use of the nucleic acid constructs, the production or use of RNA, and production of host cells and cell-free extracts will employ, unless otherwise indicated, routine conventional techniques of molecular biology, microbiology, and recombinant DNA manipulation and production.

In some embodiments, the nucleic acid constructs utilized in the assays above may comprise one or more regulatory elements. Any transcriptional regulatory element(s) known to those skilled in the art are intended to be included within the scope of the present invention for use in controlling transcription of a nucleic acid construct. Non-limiting examples of the types of transcriptional regulatory element(s) include a constitutive promoter, a tissue-specific promoter or an inducible promoter. In a specific embodiment, the transcription of a nucleic acid construct is controlled, at least in part, by one or more mammalian (in some embodiments, human) transcriptional regulatory element(s). In a specific embodiment, the transcription of a nucleic acid construct is controlled, at least in part, by a strong promoter, such as CMV. The transcriptional regulatory elements may be operably linked to a nucleic acid construct.

The nucleic acid constructs described herein may be part of a vector that provides post-transcriptional regulatory elements. The vector chosen will depend upon a variety of factors, including, without limitation, the strength of the transcriptional regulatory elements and the host cell to be used to express a nucleic acid construct.

In a specific embodiment, the nucleic acid construct is a part of CMV vector, such as pcDNA™3.1/Hygro (Invitrogen Corp., Carlsbad, Calif.). In other embodiments, the nucleic acid construct is part of a T7 vector, a lac vector, a pCEP4 vector or a 5.0/FRT vector.

Any reporter gene well-known to one of skill in the art may be used in the nucleic acid constructs described herein to identify or validate whether a compound causes ribosomal frameshifting. Reporter genes refer to a nucleotide sequence encoding or coding for a protein that is readily detectable either by its presence or activity. In certain embodiments, the nucleotide sequence of the reporter gene includes exons and introns. In other embodiments, the nucleotide sequence of the reporter gene excludes introns. In specific embodiments, the reporter gene coding sequence is used. Reporter genes may be obtained and the nucleotide sequence of the reporter gene determined by any method well-known to one of skill in the art.

Examples of reporter genes include, but are not limited to, nucleotide sequences encoding or coding for luciferase (e.g., firefly luciferase, renilla luciferase, and click beetle luciferase), fluorescent protein (e.g., green fluorescent protein ("GFP"), yellow fluorescent protein, red fluorescent protein, cyan fluorescent protein, and blue fluorescent protein), beta-galactosidase ("β-gal"), beta-glucoronidase, beta-lactamase, chloramphenicol acetyltransferase ("CAT"), and alkaline phosphatase ("AP").

In a specific embodiment, a gene product of a reporter gene utilized in the nucleic acid constructs is easily detected and the activity of the gene product detected is not normally found in the cell or organism of interest. In a specific embodiment, a reporter gene utilized in the nucleic acid constructs is not, per se, SMN1 or SMN2.

Host cells containing a nucleic acid construct or RNA transcript (e.g., a pre-mRNA or RNA transcript) may be produced utilizing any technique known to one of skill in the art. For example, cells may be transformed or transfected with a nucleic acid construct described herein or a RNA transcript transcribed from a nucleic acid construct described herein. In one embodiment, the host cell is transiently transfected with the nucleic acid construct. In an alternative embodiment, the host cell is stably transfected with a nucleic acid construct. In certain embodiments, more than one nucleic acid construct may be transfected into a host cell. In one specific embodiment, the host cell is a mammalian cell. In another specific embodiment, the host cell is a human cell. In another embodiment, the host cells are primary cells isolated from a tissue or other biological sample of interest. Host cells that can be used in the methods of the present invention include, but are not limited to, hybridomas, pre-B cells, HEK293 cells, HEK293T cells, HEK293H cells, HeLa cells, HepG2 cells, K562 cells, 3T3 cells, MCF7 cells, SkBr3 cells, COS cells, BT474 cells, the human type I SMA fibroblast cell line GMOGM03813 or neuroblastoma cells lines such as MC-IXC, SK-N-MC, SK-N-MC, SK-N-DZ, SH-SY5Y, and BE(2)-C. In one embodiment, the host cells are immortalized cell lines derived from a source, e.g., a tissue. In one embodiment, the host cells are stem cells.

Transformation may be by any known method for introducing polynucleotides into a host cell. The transformation procedure used depends upon the host to be transformed. Such methods are well-known to one of skill in the art.

Stable cell lines may be generated by introducing a nucleic acid construct further comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

The invention also provides for the translation of a RNA transcript from a nucleic acid constructs in a cell-free system. In a specific embodiment, a cell-free extract provides the components necessary for translation of a RNA transcript in vitro. Any technique well-known to one of skill in the art may be used to generate cell-free extracts for translation in vitro. For example, the cell-free extracts for in vitro translation reactions can be generated by centrifuging cells and clarifying the supernatant.

In some embodiments, a cell-free extract provides the components necessary for in vitro transcription of nucleic acid constructs and translation. In a specific embodiment, the cell-free extract utilized is the in vitro transcription and translation (TNT)-coupled reticulocyte lysate available from Promega. In certain embodiments, a cell-free extract provides the components necessary for in vitro transcription of nucleic acid constructs, splicing, and translation.

The cell-free extract may be isolated from cells of any species origin. For example, the cell-free extract may be isolated from human cells (e.g., HeLa cells, RD cells, A204 cells), HEK293 cells, Vero cells, yeast, mouse cells (e.g., cultured mouse cells), rat cells (e.g., cultured rat cells), Chinese hamster ovary (CHO) cells, *Xenopus* oocytes, rabbit reticulocytes, primary cells, cancer cells (e.g., undifferentiated cancer cells), cell lines, wheat germ, rye embryo, or bacterial cell extract. In a specific embodiment, the cells from which the cell-free extract is obtained do not endogenously express SMN or SMNΔEx7. In another embodiment, the cell-free extract is an extract isolated from human cells. In a further embodiment, the human cells that can be used in the methods described herein, include, but are not limited to HeLa cells, HEK293 cells, HEK293T cells, HEK293H cells, HeLa cells, HepG2 cells, K562 cells, 3T3 cells, MCF7 cells, SkBr3 cells, BT474 cells, MC-IXC cells, SK-N-MC cells, SK-N-MC cells, SK-N-DZ cells, SH-SY5Y cells, or BE(2)C.

Assays For Assessing the Effect of Compounds on the Efficiency of Viral Programmed Ribosomal Frameshifting Compounds that modulate ribosomal frameshifting may be used to alter a protein translated from a particular gene, e.g., SMN2. The protein (SMNΔEx7) found in nature that is encoded by the SMN2 gene lacks amino acid residues encoded by exon 7 of SMN2 and includes amino acids encoded by exon 8, resulting in rapid degradation of the SMNΔEx7 protein. Compounds that modulate ribosomal frameshifting may be used to cause frameshifts in SMN2 resulting in the production of stabilized SMNΔEx7 proteins that have an increased abundance or half-life relative to naturally-occurring SMNΔEx7 protein. Assays for use in the generation of stabilized SMNΔEx7 proteins are described in co-pending U.S. provisional application No. 61/156,429, which is incorporated by reference herein in its entirety.

Compounds identified or validated herein as modulating the efficiency of programmed ribosomal frameshifting may modulate any form of programmed ribosomal frameshifting.

In certain embodiments, compounds identified or validated as capable of modulating the efficiency of programmed ribosomal frameshifting in the assays described above can be assessed for their ability to modulate the efficiency of viral programmed ribosomal frameshifting using any technique known to one of skill in the art.

In one embodiment, the ability of a compound to modulate the efficiency of viral programmed ribosomal frameshifting is assessed utilizing an assay which measures the ratio of viral proteins encoded by viral genes expressed from overlapping reading frames in which programmed ribosomal frameshifting regulates the expression of the genes.

Constructs comprising the HIV-1 frameshift signal for use in frameshifting assays are described in the art (see Biswas, et al., 2004, *J. Virol.* 78:2082-2087; Dulude, et al., 2006, *Virology,* 345:127-136, both of which are incorporated by reference in their entireties). Accordingly, compounds identified as modulating viral ribosomal frameshifting using the assays described above can be validated for their ability to modulate the efficiency of programmed ribosomal frameshifting using such constructs.

For example, the ability of a compound to modulate the efficiency of viral programmed ribosomal frameshifting can be validated in a dual luciferase assay comprising: (a) contacting a compound with a host cell expressing a nucleic acid construct comprising in 5' to 3' order: (i) a promoter sequence; (ii) the *Renilla* luciferase (rluc) gene; (iii) the HIV-1 frameshift signal sequence; (iv) the firefly luciferase gene (fluc); and (v) a polyadenylation sequence; and (b) detecting the activity of *Renilla* luciferase versus that of firefly luciferase, wherein a compound that modulates the efficiency of programmed ribosomal frameshifting is validated if (i) the activity of *Renilla* luciferase in the presence of the compound is not changed relative to the activity of *Renilla* luciferase detected in the absence of the compound; and (ii) the activity of firefly luciferase detected in the presence of the compound is changed relative to the activity of firefly luciferase detected in the absence of the compound. In other words, the ratio of *Renilla* luciferase to firefly luciferase is changed in the presence of the compound relative to the absence of the compound.

In certain embodiments, the ability of a compound to modulate the efficiency of viral programmed ribosomal frameshifting is assessed utilizing an in vitro or in vivo viral replication assay in which the ratio of viral proteins is monitored as an indication of the degree to which the efficiency of viral programmed ribosomal frameshifting is modulated. In a specific embodiment, a compound identified herein changes the ratio of viral proteins in an in vitro or in vivo assay known to one of skill in the art.

In specific embodiments, the ability of a compound to modulate the efficiency of viral programmed ribosomal frameshifting is assessed by measuring the affect of the compound on the ratio of Gag to Gag-Pol polyproteins. Any technique known to one skilled in the art can be used to measure a change in the ratio of Gag to Gag-Pol polyproteins. In a specific embodiment, a change in the ratio Gag to Gag-Pol polyproteins is assessed by the assay described in Biswas, et al., 2004, *J. Virol.* 78:2082-2087, which is incorporated herein by reference in its entirety. Briefly, the assay comprises: (a) contacting a compound with an in vitro transcription and translation (TNT)-coupled reticulocyte lysate (Promega) containing a plasmid (pHIVgp) that contains HIV-1 coding regions, including the Gag-Pol coding sequences with wild-type HIV-1 ribosomal frameshift signals, in the presence of [$^{35}$S]-methionine; and (b) determining the ratio of the [$^{35}$S]-methionine-labeled p55$^{gag}$ to [$^{35}$S]-methionine-labeled p160$^{gag\text{-}pol}$ polyproteins expressed from the plasmid exposed to said compound, wherein a compound that affects the ratio of Gag to Gag-Pol polyproteins is identified or validated if the ratio of Gag to Gag-Pol expressed from the plasmid exposed to said compound is changed relative to the ratio of Gag to Gag-Pol expressed from the plasmid in the absence of said compound or in the presence of a negative control. The amount of Gag to Gag-Pol polyproteins can be determined using SDS-polyacrylamide gel separation and quantitated using densitometry.

In certain embodiments, the ratio of Gag to Gag-Pol expressed from the plasmid exposed to a compound is altered by at least 20% (and in some embodiments, at least a 25%, at least a 30%, at least a 40%, at least a 50%, at least a 75%, at least a 80%, at least a 90% or at least a 95%) relative to the ratio of Gag to Gag-Pol expressed from the plasmid not exposed to the compound. In other embodiments, the ratio of Gag to Gag-Pol expressed from the plasmid exposed to a compound is altered by 20% to 50%, 20% to 75%, 20% to 95%, 25% to 50%, 25% to 75%, 25% to 95%, 50% to 75%, 50% to 95% or 75% to 95% relative to the ratio of Gag to Gag-Pol expressed from the plasmid not exposed to the compound.

In certain embodiments, a compound that modulates the efficiency of programmed ribosomal frameshifting causes at least a 20% (and in some embodiments at least at 25%, at least a 30%, at least a 40%, at least a 75% or at least a 90%) alteration in programmed ribosomal frameshifting activity, as measured using an assay described herein or known to one of skill in the art.

In a specific embodiment, a compound that modulates the efficiency of programmed ribosomal frameshifting causes a reduction in programmed ribosomal frameshift activity, as measured using an assay described above. In certain embodiments, the assay is the dual luciferase construct assay as described in Biswas, et al., 2004, *J. Virol.* 78:2082-2087, wherein 100% is the baseline activity measured in the absence of compounds. In an aspect of these embodiments, the reduction in programmed ribosomal frameshifting is at least a 20%, at least a 25%, at least a 30%, at least a 40%, at least a 50%, at least a 75%, at least a 80%, at least a 90% or at least a 95% reduction in programmed ribosomal frameshifting activity.

In a specific embodiment, a compound that modulates the efficiency of programmed ribosomal frameshifting activity results in greatly disabled virus production as measured by a viral infectivity assay. In another specific embodiment, a compound that modulates the efficiency of programmed ribosomal frameshifting activity results in the production of an attenuated virus or viral particle. In another embodiment, a compound that modulates the efficiency of programmed ribosomal frameshifting activity results in completely abolished virus production as measured by a viral infectivity assay.

Anti-Viral Activity of Compounds that Modulate Programmed Ribosomal Frameshifting
Anti-Viral Assays The antiviral activity of a compound that modulates the efficiency of programmed ribosomal frameshifting can be detected using any technique known to one of skill in the art or described herein.

Viral Infectivity Assay

Any viral infectivity known to one skilled in the art can be utilized to determine the ability of a compound that modulates programmed ribosomal frameshifting to inhibit viral replication and/or infectivity. In one embodiment, an HIV-1 single cycle infectivity assay is used to determine the ability of a compound that modulates the efficiency of programmed ribosomal frameshifting to inhibit viral replication and/or infectivity. In a specific embodiment, the HIV-1 infectivity assay described in Biswas, et al., 2004, *J. Virol.* 78:2082-2087 or Dulude, et al., 2006, *Virology*, 345:127-136 (each of which is incorporated by reference) is utilized to determine the ability of a compound that modulates the efficiency of programmed ribosomal frameshifting to inhibit viral infectivity and/or replication. Briefly, this assay comprises: (a) contacting a compound with a first cell(s) infected with a viral particle produced by (i) transfecting a second cell with 1) a Gag-Pol vector which provides the coding sequences for all of the HIV-1 accessory proteins and the Gag and Gag-Pol polyproteins, with the wild-type frameshift signal (pHIVg-pwt), 2) a plasmid that encodes a viral envelope protein, such as vesicular stomatitis virus G envelope protein (VSV-G), which allows the vector virus to be pseudotyped, and 3) a transducing vector that contains cis-acting signals for vector propagation, including the LTRs and the packaging signal, as well as a marker gene (such as a green fluorescent protein, gfp) and an antibiotic resistance gene (e.g., puromycin resistance gene, puro) for the detection and analysis of infectivity, and (ii) harvesting the resulting viral particles 72 hours post-transfection; and (b) using the antibiotic (e.g., puromycin) to select for infectious units of the HIV-1 vector virus and scoring the number of infectious units by counting marker-positive (e.g., GFP-positive), antibiotic-resistant cells by a technique known to one of skill in the art, such as fluorescence microscopy, wherein a compound that interferes with viral replication and/or infectivity is identified or validated if the titer of the virus produced in the presence of the compound is changed relative to the titer of the virus produced in the absence of the compound or in the presence of a negative control (e.g., DMSO or PBS).

Viral Cytopathic Effect (CPE) Assay

CPE is the morphological changes that cultured cells undergo upon being infected by most viruses. These morphological changes can be observed easily in unfixed, unstained cells by microscopy. Forms of CPE, which can vary depending on the virus, include, but are not limited to, rounding of the cells, appearance of inclusion bodies in the nucleus and/or cytoplasm of infected cells, and formation of syncytia, or polykaryocytes (large cytoplasmic masses that contain many nuclei).

The CPE assay can provide a measure of the antiviral effect of a compound that modulates the efficiency of programmed ribosomal frameshifting. In a non-limiting example of such an assay, compounds that modulate the efficiency of programmed ribosomal frameshifting are serially diluted (e.g. 1000, 500, 100, 50, 10, 1 µg/ml) and added to 3 wells containing a cell monolayer (preferably mammalian cells at 80-100% confluent) of a 96-well plate. Within 5 minutes, viruses are added and the plate sealed, incubated at 37° C. for the standard time period required to induce near-maximal viral CPE (e.g., approximately 48 to 120 hours, depending on the virus and multiplicity of infection). CPE is read microscopically after a known positive control drug is evaluated in parallel with the compounds being assayed. The data are expressed as 50% effective concentrations or approximated virus-inhibitory concentration, 50% endpoint ($EC_{50}$) and cell-inhibitory concentration, 50% endpoint ($IC_{50}$). General selectivity index ("SI") is calculated as the $IC_{50}$ divided by the $EC_{50}$. These values can be calculated using any method known in the art, e.g., the computer software program Mac-Synergy II by M. N. Prichard, K. R. Asaltine, and C. Shipman, Jr., University of Michigan, Ann Arbor, Mich.

In one embodiment, a compound that modulates the efficiency of viral programmed ribosomal frameshifting has an SI of greater than 3, or 4, or 5, or 6, or 7, or 8, or 9, or 10, or 11, or 12, or 13, or 14, or 15, or 20, or 21, or 22, or 23, or 24, or 25, or 30, or 35, or 40, or 45, or 50, or 60, or 70, or 80, or 90, or 100, or 200, or 300, or 400, or 500, 1,000, or 10,000. In some embodiments, a compound that modulates the efficiency of viral programmed ribosomal frameshifting has an SI of greater than 10. In a specific embodiment, compounds with an SI of greater than 10 are further assessed in other in vitro and in vivo assays described herein or others known in the art to characterize safety and efficacy.

Neutral Red (NR) Dye Uptake Assay

The NR Dye Uptake assay can be used to validate the CPE assay. In a non-limiting example of such an assay, the same 96-well microplates used for the CPE assay can be used. Neutral red is added to the medium, and cells not damaged by virus take up a greater amount of dye. The percentage of uptake indicating viable cells is read on a microplate autoreader at dual wavelengths of 405 and 540 nm, with the difference taken to eliminate background. (See McManus, et al., *Appl. Environment. Microbiol.* 31:35-38, 1976). An $EC_{50}$ is determined for samples with infected cells and contacted with a compound that modulates the efficiency of programmed ribosomal frameshifting, and an $IC_{50}$ is determined for samples with uninfected cells contacted with a compound that modulates the efficiency of programmed ribosomal frameshifting.

Virus Yield Assay

Lysed cells and supernatants from infected cultures such as those in the CPE assay can be used to assay for virus yield (production of viral particles after the primary infection). In a non-limiting example, these supernatants are serial diluted and added onto monolayers of susceptible cells (e.g., Vero cells). Development of CPE in these cells is an indication of the presence of infectious viruses in the supernatant. The 90% effective concentration ($EC_{90}$), the test compound concentration that inhibits virus yield by 1 log 10, is determined from these data using known calculation methods in the art. In one embodiment, the $EC_{90}$ of a compound that modulates the efficiency of viral programmed ribosomal frameshifting is at least 1.5 fold, 2 fold, 3 fold, 4 fold, 5 fold, 6 fold, 7 fold, 8 fold, 9 fold, 10 fold, 20 fold, 30 fold, 40 fold, or 50 fold less than the $EC_{90}$ of the negative control sample.

Plaque Reduction Assay

In a non-limiting example of a plaque reduction assay, a virus is diluted into various concentrations and added to each well containing a monolayer of the target mammalian cells in triplicate. The plates are then incubated for a period of time to achieve effective infection of the control sample (e.g., 1 hour with shaking every fifteen minutes). After the incubation period, an equal amount of 1% agarose is added to an equal volume of each compound dilution prepared in 2× concentration. In certain embodiments, compounds that modulate the efficiency of programmed ribosomal frameshifting at test concentrations between about 0.03 μg/ml to about 100 μg/ml can be tested with a final agarose overlay concentration of 0.5%. The compound-agarose mixture is applied to each well in 2 ml volume and the plates are incubated for three days, after which the cells are stained with a 1.5% solution of neutral red. At the end of the 4-6 hour incubation period, the neutral red solution is aspirated, and plaques counted using a stereomicroscope. Alternatively, a final agarose concentration of 0.4% can be used. In other embodiments, the plates are incubated for more than three days with additional overlays being applied on day four and on day 8 when appropriate. In another embodiment, the overlay medium is liquid rather than semi-solid.

Virus Titer Assay

In virus titer assays, a monolayer of a target mammalian cell line is infected with different amounts (e.g., multiplicity of 3 plaque forming units (pfu) or 5 pfu) of virus and subsequently cultured in the presence or absence of various dilutions of compounds that modulate the efficiency of programmed ribosomal frameshifting (e.g., 0.1 μg/mL, 1 μg/mL, 5 μg/mL, or 10 μg/mL) to be tested. Infected cultures are harvested 48 hours or 72 hours post infection and titered by standard plaque assays known in the art on the appropriate target cell line (e.g., Vero cells, MRC5 cells). In certain embodiments, culturing the infected cells in the presence of the compounds reduces the yield of infectious virus by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to culturing the infected cells in the absence of compounds. In a specific embodiment, culturing the infected cells in the presence of compounds that modulate the efficiency of programmed ribosomal frameshifting reduces the PFU/mL by at least 10 fold relative to culturing the infected cells in the absence of compounds that modulate the efficiency of programmed ribosomal frameshifting.

In certain embodiments, culturing the infected cells in the presence of compounds that modulate the efficiency of programmed ribosomal frameshifting reduces the yield of infectious virus by at least 0.5 log 10, 1 log 10, 1.5 log 10, 2 log 10, 2.5 log 10, 3 log 10, 3.5 log 10, 4 log 10, 4.5 log 10, 5 log 10, 5.5 log 10, 6 log 10, 6.5 log 10, 7 log 10, 7.5 log 10, 8 log 10, 8.5 log 10, or 9 log 10 relative to culturing the infected cells in the absence of compounds. In a specific embodiment, culturing the infected cells in the presence of compounds that modulate the efficiency of programmed ribosomal frameshifting reduces the yield of infectious virus by at least 1 log 10 or 2 log 10 relative to culturing the infected cells in the absence of compounds. In another specific embodiment, culturing the infected cells in the presence of compounds that modulate the efficiency of programmed ribosomal frameshifting reduces the yield of infectious virus by at least 2 log 10 relative to culturing the infected cells in the absence of compounds.

Flow Cytometry Assay

Flow cytometry can be utilized to detect expression of virus antigens in infected target cells cultured in the presence or absence of compounds that modulate the efficiency of programmed ribosomal frameshifting (See, e.g., McSharry et al., *Clinical Microbiology Rev.*, 1994, 7:576-604). In other embodiments, intracellular viral antigens or viral nucleic acid can be detected by flow cytometry with techniques known in the art.

Cell Lines for Antiviral Assays

In a specific embodiment, cells used in the antiviral assays described herein are susceptible to infection with a virus. In some embodiments, cell lines for use in antiviral assays are genetically engineered to render them more suitable hosts for viral infection or viral replication and more convenient substrates for rapidly detecting virus-infected cells (See, e.g., Olivo, P. D., *Clin. Microbiol. Rev.,* 1996, 9:321-334). In some aspects, these cell lines are available for testing the antiviral activity of a compound that modulates the efficiency of programmed ribosomal frameshifting on blocking any step of viral replication and infectivity, such as, transcription, translation, pregenome encapsidation, reverse transcription, particle assembly and release.

Cytotoxicity Assays

Compounds that modulate the efficiency of programmed ribosomal frameshifting may be tested for cytotoxicity in mammalian, preferably human, cell lines. In certain embodiments, cytotoxicity is assessed in one or more of the following cell lines: U937, a human monocyte cell line; primary peripheral blood mononuclear cells (PBMC); Huh7, a human hepatoblastoma cell line; 293T and 293H, human embryonic kidney cell lines; and THP-1, monocytic cells; a HeLa cell line; fibroblasts or other cell types isolated from SMA patients; SMA patient-derived cell lines, e.g., the GM03813 cell line; and neuroblastoma cells lines, such as MC-IXC, SK-N-MC, SK-N-MC, SK-N-DZ, SH-SY5Y and BE(2)-C. In general, many assays known to one skilled in the art can be used to assess viability of cells or cell lines following exposure to a compound and, thus, determine the cytotoxicity of the compound.

The toxicity and/or efficacy of a compound that modulates the efficiency of programmed ribosomal frameshifting can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified or validated in accordance with the invention that exhibits large therapeutic indices is preferred. While a compound identified or validated in accordance with the invention that exhibits toxic side effects may be used, care should be taken to design a delivery system that targets such agents to the site of affected tissue in order to minimize potential damage to uninfected cells and, thereby, reduces side effects.

The data obtained from the cell culture assays and animal studies can be used in formulating a range of dosage of a compound identified or validated in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography.

Compositions

Any compound described herein may optionally be in the form of a composition comprising the compound and an optional carrier, excipient or diluent. Other embodiments provided herein include pharmaceutical compositions comprising an effective amount of a compound and a pharmaceutically acceptable carrier, excipient, or diluent. The pharmaceutical compositions are suitable for veterinary and/or human administration. The pharmaceutical compositions provided herein can be in any form that allows for the composition to be administered to a subject, and these pharmaceutical compositions may be formulated for the route of administration.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier when the pharmaceutical composition is administered intravenously. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents. Further provided herein are anhydrous pharmaceutical compositions and dosage forms comprising one or more compounds of the present invention. The compositions and single unit dosage forms can take the form of solutions, suspensions, emulsion, tablets, pills, capsules, powders, sustained-release formulations and the like.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Because of their ease of administration, tablets and capsules represent the most advantageous oral dosage unit forms, in which case solid excipients are employed. In general, pharmaceutical compositions and dosage forms are prepared by uniformly and intimately admixing the active ingredients with liquid carriers, finely divided solid carriers, or both, and then shaping the product into the desired presentation if necessary.

Examples of excipients that can be used in oral dosage forms provided herein include, but are not limited to, binders, fillers, disintegrants, and lubricants.

Prophylactic and Therapeutic Methods

In certain embodiments, a compound identified or validated using an assay described herein has utility as an antiviral agent. In one embodiment, a compound identified or validated using an assay described herein may be used to inhibit or reduce viral replication. In another embodiment, a compound identified or validated using an assay described herein may be used to inhibit or reduce a viral infection. In another embodiment, a compound identified or validated using an assay described herein may be used to reduce viral titers in vitro or in vivo. In another embodiment, a compound identified or validated using an assay described herein may be used to do one or more of the following: treat a viral infection, prevent a viral disease, or treat a viral disease.

In one embodiment, the invention provides a method for treating a viral infection in a subject, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for preventing a viral disease in a subject, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for treating a viral disease in a subject, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for reducing or inhibiting a viral infection, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for reducing or inhibiting a viral infection, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for reducing or inhibiting a viral replication, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for inhibiting or reducing viral replication and/or viral infectivity in a subject, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for reducing viral titers in a subject, comprising administering to a subject in need thereof an effective amount of a compound or pharmaceutical composition thereof, wherein the compound modulates the efficiency of programmed ribosomal frameshifting as measured in vitro or in cells by an increase in the amount or activity of a fusion protein encoded by a nucleic acid construct or translated from a RNA transcript (e.g., a mRNA transcript) transcribed from the nucleic acid construct, and wherein the nucleic acid construct comprises, in 5' to 3' order: (i) the nucleic acid residues of exon 6 of SMN; (ii) the nucleic acid residues of intron 6 of SMN; (iii) the nucleic acid residues of exon 7 of SMN, wherein a single guanine is inserted after the 48th nucleotide residue from the 5' end of exon 7 of SMN (i.e., before the 6th nucleotide from the 3' end of exon 7 of SMN); (iv) the nucleic acid residues of intron 7 of SMN; (v) a fragment of the nucleic acid residues of exon 8 of SMN, wherein the fragment is composed of the first 23 nucleotides from the 5' end of exon 8 of SMN; and (vi) a reporter gene lacking a start codon, wherein the reporter gene is fused to the fragment of the nucleic acid residues of exon 8 of SMN such that the reporter gene and the fragment are out of frame with each other in the mRNA transcript transcribed from the nucleic acid construct, and wherein the production of the mRNA transcript generates a stop codon in the region of the mRNA transcript that corresponds to the fragment of the nucleic acid residues of exon 8 of SMN. In certain embodiments, an internal start codon (e.g., an ATG) found in exon 6 is used as the start codon for the nucleic acid construct. In some embodiments, the nucleic acid construct comprises a start codon 5' to the nucleic acid residues of exon 6 of SMN.

In another embodiment, the invention provides a method for inhibiting or reducing viral replication and/or viral infectivity comprising contacting a cell or a population of cells containing a virus or provirus with an effective amount of a compound or a pharmaceutical composition thereof, wherein the effective amount is an amount effective to modulate the efficiency of programmed ribosomal frameshifting as measured by, e.g., a dual luciferase construct assay, such as described herein. In a specific embodiment, the invention provides a method for inhibiting or reducing viral replication and/or viral infectivity, comprising administering to a subject in need thereof an effective amount of a compound or a pharmaceutical composition thereof, wherein the effective amount is an amount sufficient to alter the efficiency of programmed ribosomal frameshifting by at least 20% (and in some embodiments, at least 25%, at least 30%, at least 40%, at least 50%, at least 75%, at least 80%, at least 90% or at least 95%) relative to a negative control as measured by, e.g., a dual luciferase construct assay, such as described herein.

In another embodiment, the invention provides a method for preventing or treating a viral disease in a subject, comprising administering to a subject in need thereof an effective amount of a compound or a pharmaceutical composition thereof, wherein the effective amount is an amount effective to modulate the efficiency of programmed ribosomal frameshifting as measured by, e.g., a dual luciferase construct assay, such as described herein. In a specific embodiment, the invention provides a method for preventing or treating a viral disease in a subject, comprising administering to a subject in need thereof an effective amount of a compound or pharmaceutical composition thereof, wherein the effective amount is an amount sufficient to alter the efficiency of programmed ribosomal frameshifting by at least 20% (and in some embodiments, at least 25%, at least 30%, at least 40%, at least 50%, at least 75%, at least 80%, at least 90%, or at least 95%) relative to a negative control as measured by, e.g., a dual luciferase construct assay, such as described herein.

In another embodiment, the invention provides a method for inhibiting or reducing viral infection, comprising administering to a subject in need thereof an effective amount of a compound or a pharmaceutical composition thereof, wherein the effective amount is an amount effective to modulate the efficiency of programmed ribosomal frameshifting as measured by, e.g., a dual luciferase construct assay. In a specific embodiment, the invention provides a method for inhibiting or reducing viral infection, comprising administering to a subject in need thereof an effective amount of a compound or a pharmaceutical composition thereof, wherein the effective amount is an amount sufficient to alter the efficiency of programmed ribosomal frameshifting by at least 20% (and in some embodiments, at least 25%, at least 30%, at least 40%, at least 50%, at least 75%, at least 80%, at least 90% or at least 95%) relative to a negative control as measured by, e.g., a dual luciferase construct assay, such as described herein.

A compound or a composition thereof may be used in combination with another agent to treat a viral infection, or prevent or treat a viral disease. In a specific embodiment, two or more compounds may be used to treat a viral infection, or prevent or treat a viral disease. In specific embodiments, a compound or a composition thereof is the only active ingredient administered to treat a viral infection, or prevent or treat a viral disease.

The effective amount of a compound to be used depends on a number of factors, including but not limited to the type of viral infection, type of viral disease, health and age of the patient, and toxicity or side effects. The present invention encompasses methods for treating viral infections, or preventing or treating viral diseases for which no therapy is available. The present invention also encompasses methods for treating viral infections, or preventing or treating viral diseases as an alternative to conventional therapies.

The present invention also provides methods of treating viral infections, or preventing or treating viral diseases in a subject in need thereof, said methods comprising administering to the subject one or more of compounds in combination with one or more additional therapies (e.g., agents). In one embodiment, one or more compounds are administered to the subject in combination with a supportive therapy, a pain relief therapy, or other therapy that does not have an effect per se on the viral infection.

Two or more compounds may be administered to a subject to treat a viral infection, or preventing or treating viral diseases in any order. In addition, one or more compounds and one or more other agents may be administered in any order to a subject to treat a viral infection, or prevent or treat a viral disease.

A combination product of one or more compounds and one or more additional agents can be administered sequentially or concurrently. In a specific embodiment, a combination product of the present invention may improve the prophylactic and/or therapeutic effect of the compound and the agent by functioning together to have an additive or synergistic effect. In another embodiment, a combination product may reduce the side effects associated with each compound and agent when taken alone.

The one or more compounds and one or more other agents of a combination product can be administered to a subject in the same pharmaceutical composition. Alternatively, the one or more compounds and one or more other agents of a combination product can be administered concurrently to a subject in separate pharmaceutical compositions. The one or more compounds and one or more other agents of a combination product may be administered to a subject by the same or different routes of administration.

In certain embodiments, the present invention encompasses the use of an attenuated virus or viral particle, which may be produced, at least in part, utilizing a compound that modulates viral programmed ribosomal frameshifting, for the prevention of a viral disease. In some embodiments, a compound that modulates programmed ribosomal frameshifting is contacted with a cell or a population of cells containing a virus, provirus or nucleic acids encoding or coding for certain components of a virus as part of the process for production of an attenuated virus or viral particle. In specific embodiments, an attenuated virus or viral particle may be produced by a method comprising contacting a compound that modulates programmed ribosomal frameshifting with a cell or population of cells containing a virus or provirus, and harvesting the resulting attenuated virus or viral particle. An attenuated virus or viral particle produced utilizing a compound that modulates programmed ribosomal frameshifting can be utilized as a vaccine. In particular, the attenuated virus or viral particle can be administered to a subject in an effective amount to prevent the development of a viral disease.

Patient Population

In some embodiments, a compound or pharmaceutical composition thereof is administered to a subject suffering from a viral infection. In other embodiments, a compound or pharmaceutical composition thereof is administered to a subject predisposed or susceptible to a viral infection. In other embodiments, a compound or pharmaceutical composition thereof is administered to a subject to treat a viral disease. In other embodiments, a compound or pharmaceutical composition thereof is administered to a subject to prevent the development of a viral disease.

In a specific embodiment, the subject suffering from a viral infection or a disease associated therewith is infected with a virus listed in Table 1 or a provirus. In another embodiment, the subject suffering from a viral infection or a disease associated therewith is infected with human immunodeficiency virus type 1 (HIV-1), human immunodeficiency virus type 2 (HIV-2), feline immunodeficiency virus (FIV), rous sarcoma virus (RSV), mouse mammary tumor virus (MMTV), simian retrovirus type 1 (SRV-1), human T cell leukemia virus type I (HTLV-I), human T cell Leukemia virus type II (HTLV-II), infectious bronchitis virus (IBV), human coronavirus (HCoV), hepatitis A virus (HAV), hepatitis B virus (HBV), hepatitis C virus (HCV), human papilloma virus (HPV), transmissible gastroenteritis virus (TGEV), berne virus (BEV), equine arteritis virus (EAV), human astrovirus serotype-1 (HAst-1), *Giardia lamblia* virus (GLV), *Saccharomyces cerevisiae* dsRNA virus L-A (ScV/L-A), *S. cerevisiae* dsRNA virus L1 (ScV/L1), bacteriophage T7, bacteriophage lambda, barley yellow dwarf virus (BYDV), beet western yellows virus (BWYV), potato leaf roll virus (PLRV), severe acute respiratory syndrome coronavirus (SARS-CoV), herpes simplex virus (HSV), and red clover necrotic mosaic virus (RCNMV).

In another specific embodiment, the subject suffering from a viral infection or a disease associated therewith is infected with any of feline immunodeficiency virus (FIV), rous sarcoma virus (RSV), mouse mammary tumor virus (MMTV), simian retrovirus type 1 (SRV-1), human T cell leukemia virus type I (HTLV-I), HTLV-II, infectious bronchitis virus (IBV), human coronavirus (HCV), transmissible gastroenteritis virus (TGEV), berne virus (BEV), equine arteritis virus (EAV), human astrovirus serotype-1 (HAst-1), *Giardia lamblia* virus (GLV), *Saccharomyces cerevisiae* dsRNA virus L-A (ScV/L-A), *S. cerevisiae* dsRNA virus L1 (ScV/L1), bacteriophage T7, bacteriophage lambda, barley yellow dwarf virus (BYDV), beet western yellows virus (BWYV), potato leaf roll virus (PLRV), severe acute respiratory syndrome coronavirus (SARS-CoV), herpes simplex virus (HSV), and red clover necrotic mosaic virus (RCNMV).

In certain embodiments, the subject suffering from a viral infection or a disease associated therewith is not infected with a human immunodeficiency virus, hepatitis virus, or human papillomavirus.

In certain embodiments, a compound or pharmaceutical composition thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound or pharmaceutical composition thereof is administered to a human infant. In other embodiments, a compound or pharmaceutical composition thereof is administered to a human toddler. In other embodiments, a compound or pharmaceutical composition thereof is administered to a human child. In other embodiments, a compound or pharmaceutical composition thereof is administered to a human adult. In yet other embodiments, a compound or pharmaceutical composition thereof is administered to an elderly human.

In certain embodiments, a compound or pharmaceutical composition thereof is administered a subject in an immunocompromised state or immunosuppressed state or at risk for becoming immunocompromised or immunosuppressed. In certain embodiments, a compound or pharmaceutical composition thereof is administered to a subject receiving or recovering from immunosuppressive therapy.

In some embodiments, a compound or pharmaceutical composition thereof is administered to a patient who is susceptible to adverse reactions to conventional anti-viral therapies. In some embodiments, a compound or pharmaceutical composition thereof is administered to a patient who has proven refractory to anti-viral therapies other than compounds, but are no longer on these therapies. Among these patients are refractory patients, and patients who are too young for conventional therapies.

In some embodiments, the subject being administered a compound or pharmaceutical composition thereof has not received therapy prior to the administration of the compound or pharmaceutical composition thereof.

Mode of Administration

When administered to a patient, a compound is preferably administered as a component of a composition that optionally comprises a pharmaceutically acceptable carrier, excipient or diluent. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In some instances, administration will result in the release of a compound into the bloodstream. In a specific embodiment, a compound is administered orally.

Dosage and Frequency of Administration

The amount of a compound that will be effective in the treatment of a viral infection, or prevention or treatment of a viral disease can be determined by standard clinical techniques. In vitro or in vivo assays may optionally be employed to help identify optimal dosage ranges. The precise dose to be employed will also depend, e.g., on the route of administration, the type of viral infection, type of viral disease, and the seriousness of the viral infection, and should be decided according to the judgment of the practitioner and each patient's or subject's circumstances.

Exemplary doses of a compound include milligram (mg) or microgram (μg) amounts per kilogram (Kg) of subject or sample weight per day (e.g., from about 1 μg per Kg to about 500 mg per Kg per day, from about 5 μg per Kg to about 100 mg per Kg per day, or from about 10 μg per Kg to about 100 mg per Kg per day. In specific embodiments, a daily dose is at least 0.1 mg, 0.5 mg, 1.0 mg, 2.0 mg, 5.0 mg, 10 mg, 25 mg, 50 mg, 75 mg, 100 mg, 150 mg, 250 mg, 500 mg, 750 mg, or at least 1 g. In another embodiment, the dosage is a unit dose of about 0.1 mg, 1 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 0.1 mg to about 1000 mg, 1 mg to about 1000 mg, 5 mg to about 1000 mg, about 10 mg to about 500 mg, about 150 mg to about 500 mg, about 150 mg to about 1000 mg, 250 mg to about 1000 mg, about 300 mg to about 1000 mg, or about 500 mg to about 1000 mg. In one embodiment, a subject is administered one or more doses of an effective amount of a compound or a pharmaceutical composition thereof, wherein the effective amount is not the same for each dose.

Combination Products

Additional agents that can be used in a combination product with compounds of the present invention for the treatment of viral infections, or prevention or treatment of viral diseases include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used, will be used or is currently being used for the treatment of viral infections, or prevention or treatment of viral diseases can be used in combination with compounds in accordance with the invention described herein.

Cell Culture Uses

The present invention provides for the use of compounds as ingredients in cell culture-related products in which it is desirable to have antiviral activity. In one embodiment, one or more compounds is added to cell culture media. In certain embodiments, compounds that prove too toxic or are not used in subjects are added to cell culture-related products, such as media.

EXAMPLES

Cryptic Splice Site

This example demonstrates that a cryptic splice site is created when a guanine residue is inserted after nucleotide 48 of exon 7 of SMN in a minigene construct comprising in 5' to 3' order: (i) the nucleic acid residues of exon 6 of SMN, the nucleic acid residues of intron 6 of SMN, the nucleic acid residues of exon 7 of SMN, the nucleic acid residues of intron 7 of SMN, the first 23 nucleic acid residues of exon 8 of SMN; and (ii) a reporter gene coding sequence fused in frame to the nucleic acid residues of exon 8 of SMN, wherein the reporter gene does not have a start codon. As a result of the cryptic splice site, a deletion of the last seven nucleotides of exon 7 occurs and a frameshift in the open reading frame of the reporter gene is created.

Materials and Methods

Preparation of the Minigene Constructs

DNA corresponding to a region of the SMN2 gene starting from the 5' end of exon 6 (ATAATTCCCCC) (SEQ ID NO: 1) and ending at nucleic acid residue 23 of exon 8 (CAGCAC) (SEQ ID NO: 2) was amplified by PCR using the following primers:

```
Forward primer:
                                    (SEQ ID NO: 3)
5'-CGCGGATCCATAATTCCCCCACCACCTC-3'

Reverse primer:
                                    (SEQ ID NO: 4)
5'-CGCGGATCCGTGCTGCTCTATGCCAGCA-3'
```

The 5' end of each primer was designed to add a BamHI site at both the 5' end of exon 6 (GGATCC) (SEQ ID NO:5) and the 3' end, after the 23$^{rd}$ nucleotide, of exon 8. Using the BamHI restriction sites, the PCR fragment was cloned into a derivative of the original pcDNA 3.1/Hygro vector which was modified as disclosed in United States Patent Publication US2005/0048549.

New UTRs were added to the modified vector using the HindIII site and the BamHI site comprising a 5'deg UTR: 5'-TAGCTTCTTACCCGTACTCCACCGTTG-GCAGCACGATCGCACGTCCCACGT GAACCATTGG-TAAACCCTG-3' (SEQ ID NO: 6) was cloned into the modified pcDNA3.1/Hygro vector together with a start codon upstream of the BamHI site; and a 3'deg UTR: 5'-ATCGAAAGTACAGGACTAGCCTTC-CTAGCAACCGCGGGCTGGGAGTCTGAGA CAT-CACTCAAGATATATGCTCGGTAACGTAT-GCTCTAGCCATCTAACTATTCCCT ATGTCTTATAGGG-3' (SEQ ID NO: 7) was cloned into the modified pcDNA3.1/Hygro vector with a stop codon using the NotI site and the XhoI site. In addition, a luciferase gene lacking its start codon was cloned into the vector using the BamHI and NotI sites.

The resulting minigene comprises, in 5' to 3' order: the 5'-deg UTR, the start codon, six additional nucleotides forming a BamHI site, the nucleic acid residues of exon 6, the nucleic acid residues of intron 6 of SMN2, the nucleic acid residues of exon 7 of SMN2, the nucleic acid residues of intron 7 of SMN2, and the first 23 nucleic acid residues of exon 8 of SMN2, an additional six nucleotides forming a BamHI site and the luciferase gene lacking the start codon.

A single guanine residue was inserted after nucleotide 48 of exon 7 of SMN2 by site-directed mutagenesis. The minigene construct produced is referred to as SMN2-G.

To generate the SMN1 version of the minigene, the sixth nucleotide of exon 7 (a thymine residue) was changed to cytosine by site directed mutagenesis. The resulting SMN1 minigene construct is referred to as SMN1-G.

Results

SMN1 and SMN2 transcripts derived from minigenes containing exon 6 through 8 and the intervening introns recapitulate the splicing of their endogenous pre-mRNAs (Lorson, et al., 1999, *Proc. Natl. Acad. Sci. USA.* 96(11):6307-6311). An SMN2-alternative splicing reporter construct which contains exons 6 to 8 and the intervening introns followed by a luciferase reporter gene was generated. Salient features of this construct are the lack of the start codon in the luciferase gene, inactivation of the termination codon (in the open reading frame that encodes the SMN protein) of exon 7 by insertion of a guanine residue after nucleic acid 48 of exon 7 and addition of a start codon (ATG) immediately upstream of exon 6.

The luciferase reporter was designed to be out of frame if exon 7 of SMN2 is removed during splicing of the pre-mRNA. In addition, the 23 nucleic acids of exon 8 are read in a different frame in the absence of exon 7, resulting in a stop codon in exon 8 in the mature mRNA transcript. Thus, the protein translated from an RNA transcript lacking exon 7 will be a truncated SMN protein lacking the luciferase portion encoded by the minigene construct. In the presence of compounds that increase the inclusion of exon 7 of SMN2 into mRNA transcribed from the SMN2 gene, more transcripts containing exon 7 were expected to be produced. In view of the teaching in Zhang, et al., 2001, *Gene Therapy,* 8:1532-1538, the presence of the additional guanine residue after nucleic acid residue 48 of exon 7 of SMN2 was expected to cause the SMN2 sequences to be in frame with the luciferase coding region in the spliced mRNA transcript containing exon 7. Thus, the resulting protein expressed from this mRNA transcript was expected to be a truncated SMN-luciferase fusion protein.

The DNA sequence of the minigene from the SMN2-G construct is provided in FIG. 2.

An SMN1 version of the SMN2 minigene construct was also generated in which the sixth nucleotide (T) of exon 7 was mutated to C to maximize the likelihood of inclusion of exon 7 into the transcript. Similar to the SMN2 minigene construct, the SMN1 minigene construct had a single guanine (SMN1-G) residue inserted after nucleic residue 48 of exon 7. The SMN1-G construct was expected to produce a truncated SMN-luciferase fusion protein because the SMN1 transcript derived from the minigene was expected to contain exon 7 and the SMN1 sequence was expected to be in frame with the luciferase coding region due to the guanine residue insert after nucleotide 48 of exon 7 of SMN1.

An increase in luciferase expression from the SMN1-G minigene construct when compared to the SMN2-G minigene construct was expected. However, the SMN1-G minigene construct did not exhibit an increase in luciferase expression when it was compared to the SMN2-G minigene construct.

In order to determine why constructs with a guanine insert yielded results different from those expected, total RNA was isolated from cells transiently transfected with the SMN1 or SMN2 versions of the minigenes. Total RNA was reverse transcribed to produce the cDNA. The cDNA was then amplified by PCR with primers specific for the minigene/reporter gene transcript. The first primer annealed to the luciferase gene and the second primer to exon 6. The PCR products were resolved on a 2% agarose gel.

RNA isolated from HEK293H cells transfected with the SMN2-G minigene construct predominately showed a band corresponding to the size of a transcript that lacks exon 7. Expression of the SMN1-G minigene construct in transiently transfected HEK293H cells resulted in the appearance of an additional band corresponding to the transcript containing exon 7. The band corresponding to the transcript containing exon 7 produced from the SMN1-G minigene construct was isolated and cloned into a pCR-blunt vector (Invitrogen). 20 clones containing the SMN1-G minigene fragment were sequenced. All of the clones lacked seven nucleotides from the inserted guanine residue to the last nucleotide of exon 7 (GTAAGGA) (SEQ ID NO: 8), demonstrating that the inclusion of exon 7 for the SMN1-G version of the minigene occurred through utilization of a cryptic splice site generated by the G insertion. Indeed, the G insertion resulted in generation of a sequence element (GTAAGG) (SEQ ID NO: 9) reminiscent of the 5' end of intron 7 (GTAAGT) (SEQ ID NO: 10). Therefore, the spliceosome preferentially used the 5' splice site between the nucleotide residue 48 of exon 7 and the G insertion (position 49). Utilization of the cryptic splice site resulted in a frameshift of the open reading frame that starts at the ATG immediately upstream of exon 6 of SMN as well as a stop codon before the luciferase portion of the minigene. Therefore, luciferase expression was substantially reduced from the SMN1-G minigene construct when a part of exon 7 was included. Analogously, the G insertion in the SMN2-G minigene construct creates a cryptic splice site in exon 7 of SMN2. The resulting inclusion of a fragment of exon 7 of SMN2 that lacks seven nucleotides at the 3' end significantly reduces luciferase expression from the SMN2-G minigene construct.

Compound that Modulates Programmed Ribosomal Frameshifting

This example demonstrates that Compound 1 modulates the efficiency of viral programmed ribosomal frameshifting.

Materials and Methods

The ability of Compound 1 to modulate the efficiency of viral programmed ribosomal frameshifting was measured using a dual luciferase assay (as described in Biswas, et al., 2004, *J. Virol.* 78(4):2082-2087).

Results

The inhibition in luciferase activity in the presence of Compound 1 relative to luciferase activity in the presence of a negative control (0.5% DMSO) averaged approximately 5-fold at a compound test concentration in a range of from approximately 5 μM to approximately 130 μM (FIG. 1).

The present invention is not to be limited in scope by the specific embodiments described herein. Indeed, various modifications of the invention and their equivalents, in addition to those described herein will become apparent to those skilled in the art from the foregoing description and accompanying figures. Such modifications are intended to fall within the scope of the appended claims.

Various patents, patent applications, and publications are cited herein, the disclosures of which are incorporated by reference in their entirety and for all purposes.

What is claimed:

1. A method for screening compounds for a compound that modulates the efficiency of viral programmed ribosomal frameshifting comprising:
   (a) contacting a compound with a host cell containing an mRNA transcript encoded by a nucleic acid construct, wherein said nucleic acid construct comprises, in 5' to 3' order: (i) a start codon; (ii) the nucleic acid residues of exon 7 of SMN, wherein a single guanine residue is inserted after the 48$^{th}$ nucleotide residue from the 5' end of exon 7 of SMN; (iii) the nucleic acid residues of intron 7 of SMN or a fragment thereof, wherein the fragment of the nucleic acid residues of intron 7 comprises any number of nucleotides of intron 7 of SMN required for a functional, minimum intron; (iv) a fragment of the nucleic acid residues of exon 8 of SMN; and (v) a reporter gene coding sequence lacking a start codon, wherein: (A) the reporter gene coding sequence is fused to the fragment of the nucleic acid residues of exon 8 of SMN such that the first codon of the reporter gene coding sequence and the start codon are out of frame with each other in the mRNA transcript transcribed from the nucleic acid construct; and (B) the production of the mRNA transcript generates a stop codon upstream from the reporter gene coding sequence in the region of the mRNA transcript that corresponds to the fragment of the nucleic acid residues of exon 8 of SMN; and (C) the start codon and the stop codon upstream from the reporter gene coding sequence in the mRNA transcript are in the same contiguous open reading frame; and
   (b) detecting the activity or amount of a fusion protein translated from the mRNA transcript, wherein an increase of 1.5-fold or more in the activity or amount of the fusion protein translated from the mRNA transcript in the presence of a compound when compared to (i) a previously determined reference range for a negative control, (ii) the activity or amount of the fusion protein translated from the mRNA transcript in the absence of the compound, or (iii) the activity or amount of the fusion protein translated from the mRNA transcript in the presence of a negative control indicates that the compound modulates the efficiency of programmed ribosomal frameshifting; and
   (c) contacting a compound that increases the activity or amount of the fusion protein translated from the mRNA transcript with a cell containing a virus that employs programmed ribosomal frameshifting and assaying the ability of the compound to decrease viral replication, wherein a decrease in viral replication of at least 1.5 log 10 in the presence of the compound indicates that a compound that modulates the efficiency of viral programmed ribosomal frameshifting is identified.

2. The method of claim 1, wherein the compound is selected from compounds of Formula (I) or Formula (II), wherein Formula (I) and Formula (II) have the following structures:

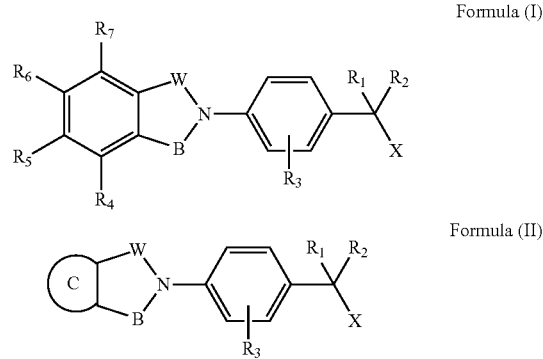

Formula (I)

Formula (II)

wherein,

W is selected from the group consisting of C(O), C(S), and $CH_2$;

B is $CH_2$ or $CH(C_nH_{2n+1})$, wherein n is an integer from 1 to 8;

Ring C is selected from the group consisting of a fused thienyl ring, a fused pyridinyl ring, and a fused cyclohexyl ring, any of which can be saturated or contain, one or two non-conjugated double bonds;

$R_1$ and $R_2$ are independently selected from the group consisting of H and $C_1$-$C_3$ alkyl, or $R_1$ and $R_2$ may be taken together with the carbon atom to which they are attached to form a $C_3$-$C_6$ cycloalkyl ring or a carbonyl group;

$R_3$ is selected from the group consisting of H, halogen, $C_1$-$C_4$ alkyl, $C_1$-$C_4$ alkoxy, $C_1$-$C_4$ haloalkyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy substituents;

$R_4$, $R_5$, $R_6$ and $R_7$ are independently selected from the group consisting of H, hydroxyl, halogen, CN, $NO_2$, sulfonamide, $C_1$-$C_8$ alkyl, $C_3$-$C_6$ cycloalkyl, cycloalkyloxy, $C_1$-$C_6$ alkoxy, $C_1$-$C_6$ haloalkoxy, $C_1$-$C_4$ haloalkyl, $C_2$-$C_8$ alkenyl, amino, $C_1$-$C_4$ alkylamino, $C_1$-$C_4$ dialkylamino, $C_3$-$C_6$ cycloalkylamino, morpholinyl, heteroaryl, arylamino, arylalkylamino, phenyl, C(O)R', NR'(COR"), NR'$SO_2$R" and NR'(CONR"R'"), wherein R', R" and R'" are independently H, $C_1$-$C_6$ alkyl, phenyl, or substituted phenyl, and wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl, and the phenyl is optionally substituted with one or more substituents selected from the group consisting of halogen, $NO_2$, CN, $C_1$-$C_4$ alkyl, $C_1$-$C_4$ haloalkyl, and $C_1$-$C_4$ alkoxy, or $R_4$ and $R_5$, $R_5$ and $R_6$, or $R_6$ and $R_7$, taken together with the carbon to which they are attached, form a ring;

X is selected from the group consisting of H; CN; C(O)$OR_8$, wherein $R_8$ is H or $C_1$-$C_8$ alkyl, and $C_1$-$C_8$ alkyl optionally is substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, phenyl, and morpholinyl; $C(O)NR_9R_{10}$ or $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a heterocyclyl ring; $CH_2OR_{ii}$, wherein $R_{11}$ is H, $C_1$-$C_8$ alkyl, or $C_3$-$C_6$ cycloalkyl, wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2Z$, wherein Z is halogen; $C(O)NHOH$; $C(O)NHCN$; $C(O)N(R_1)SO_2R_{13}$, wherein $R_{13}$ is $C_1$-$C_4$ alkyl, phenyl, or substituted phenyl; $C_1$-$C_8$ alkyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino.

3. The method of claim 1, wherein the compound is selected from compounds of Formula (Ia) or Formula (IIa), wherein Formula (Ia) and Formula (IIa) have the following structures:

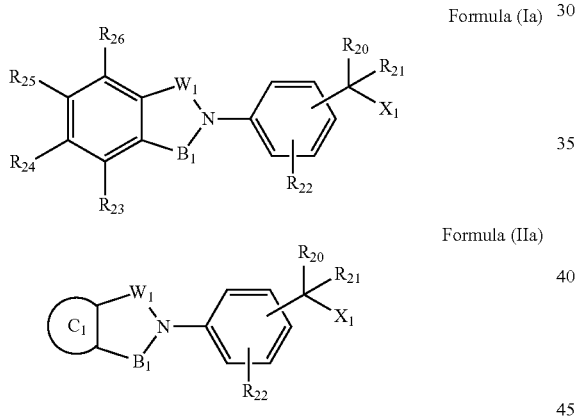

Formula (Ia)

Formula (IIa)

wherein, $W_1$ is selected from the group consisting of C(O), C(S), and $CH_2$;

$B_1$ is $CH_2$ or $CH(C_mH_{2m+1})$, wherein m is an integer from 1 to 8;

Ring $C_1$ is selected from the group consisting of a thienyl ring, a pyridinyl ring, a cyclohexyl ring, a benzo[d][1,3]dioxolyl ring and a 2,3-dihydrobenzo[b][1,4]dioxinyl ring, wherein benzo[d][1,3]dioxolyl and 2,3-dihydrobenzo[b][1,4]dioxinyl, each having a benzo ring portion, are fused via said benzo portion, and wherein any of the foregoing rings may optionally be fully or partially saturated;

$R_{20}$ and $R_{21}$ are independently selected from the group consisting of H and $C_1$-$C_3$ alkyl, or $R_{20}$ and $R_{21}$ may be taken together with the carbon atom to which they are attached to form a $C_3$-$C_6$ cycloalkyl ring or a carbonyl group;

$R_{22}$ is selected from the group consisting of H, halogen, $C_1$-$C_4$ alkyl, $C_1$-$C_4$ alkoxy, $C_1$-$C_4$ haloalkyl, cyano, nitro, heteroaryl, and phenyl optionally substituted with any combination of one to five halogen, nitro, cyano, $C_1$-$C_4$ alkyl, $C_1$-$C_4$ haloalkyl or $C_1$-$C_4$ alkoxy substituents;

$R_{23}$, $R_{24}$, $R_{25}$ and $R_{26}$ are independently selected from the group consisting of H, hydroxyl, halogen, cyano, nitro, sulfonamide, $C_1$-$C_8$ alkyl, $C_1$-$C_6$ alkoxy, $C_1$-$C_6$ alkoxyalkyl, $C_1$-$C_6$ alkoxyalkyl, $C_1$-$C_6$ haloalkoxy, $C_1$-$C_4$ haloalkyl, $C_2$-$C_6$ alkenyl, $C_2$-$C_4$ haloalkenyl, formyl, $C_1$-$C_6$ alkylcarbonyl, amino, $C_1$-$C_4$ alkylamino, $C_1$-$C_4$ dialkylamino, $C_1$-$C_4$ aminoalkyl, $C_1$-$C_4$ alkylaminoalkyl, $C_1$-$C_4$ dialkylaminoalkyl, phenyl, $C_3$-$C_6$ cycloalkyl, $C_3$-$C_6$ cycloalkylalkyl, $C_3$-$C_6$ cycloalkylalkoxy, cycloalkyloxy, heterocyclyl, heterocyclylalkyl, heteroaryl, and phenylcarbonyl, wherein amino is optionally disubstituted with one substituent selected from hydrogen, $C_1$-$C_6$ alkyl or phenyl and the other is selected from formyl, phenyl, $C_3$-$C_6$ cycloalkyl, $C_1$-$C_6$ alkylcarbonyl, aminocarbonyl, $C_1$-$C_6$ alkylaminocarbonyl, $C_1$-$C_6$ dialkylaminocarbonyl, phenylcarbonyl, phenylaminocarbonyl, N-phenyl-N—$C_1$-$C_6$ alkyl-aminocarbonyl, $C_1$-$C_6$ alkylsulfonyl, aminosulfonyl, $C_1$-$C_6$ alkylaminosulfonyl, $C_1$-$C_6$ dialkylaminosulfonyl or phenylsulfonyl, wherein each instance of $C_1$-$C_6$ alkylcarbonyl is optionally substituted on the alkyl portion with one or more substituents selected from the group consisting of halogen, $C_1$-$C_4$ alkoxy, $C_1$-$C_6$ alkylamino, $C_1$-$C_6$ dialkylamino, cycloalkylamino and heterocyclyl, wherein each instance of phenyl is optionally substituted with one or more substituents selected from the group consisting of halogen, nitro, cyano, $C_1$-$C_4$ alkyl, $C_1$-$C_4$ haloalkyl and $C_1$-$C_4$ alkoxy, and alternatively, $R_{23}$ and $R_{24}$, $R_{24}$ and $R_{25}$ or $R_{25}$ and $R_{26}$ may be taken together with the carbons to which they are attached to form a $C_3$-$C_6$ cycloalkyl ring;

$X_1$ is absent or is selected from the group consisting of H, cyano, $C_1$-$C_8$ alkyl, $C_1$-$C_4$ alkoxy, amino, $C_1$-$C_4$ alkylamino, $C_1$-$C_4$ dialkylamino, carboxy, $C_1$-$C_8$ alkoxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, aminosulfonylaminocarbonyl, $C_1$-$C_8$ alkylaminosulfonylaminocarbonyl, $C_1$-$C_8$ dialkylaminosulfonylaminocarbonyl, $C_1$-$C_8$ alkylsulfonylaminocarbonyl, phenylsulfonylaminocarbonyl and heterocyclylcarbonyl, wherein $C_1$-$C_4$ alkoxy and the $C_1$-$C_8$ alkoxy portion of $C_1$-$C_8$ alkoxycarbonyl is optionally substituted with one or more substituents selected from the group consisting of halogen, $C_1$-$C_4$ alkoxy, $C_1$-$C_4$ haloalkyl, amino, $C_1$-$C_6$ alkylamino, $C_1$-$C_6$ dialkylamino, cycloalkylamino, phenyl and heterocyclyl, wherein $C_1$-$C_8$ alkyl is optionally substituted with one or more substituents selected from the group consisting of halogen, hydroxyl, $C_1$-$C_4$ haloalkyl, $C_2$-$C_8$ alkenyl, $C_1$-$C_6$ alkoxy, $C_1$-$C_4$ alkoxyalkoxy, $C_3$-$C_6$ cycloalkyloxy, amino, $C_1$-$C_6$ alkylamino, $C_1$-$C_6$ dialkylamino, cycloalkylamino, aminocarbonyl, $C_1$-$C_6$ alkylaminocarbonyl, $C_1$-$C_6$ dialkylaminocarbonyl, hydroxylaminocarbonyl, cyanoaminocarbonyl, $C_1$-$C_6$ alkylsulfonylaminocarbonyl, phenylsulfonylaminocarbonyl and heterocyclyl, wherein $C_1$-$C_4$ alkoxy or $C_2$-$C_8$ alkenyl are each further optionally substituted with one or more substituents selected from the group consisting of $C_1$-$C_4$ alkoxy, $C_1$-$C_4$ haloalkyl, amino, $C_1$-$C_6$ alkylamino and $C_1$-$C_6$ dialkylamino.

4. The method of claim 3, wherein: (a) m is an integer selected from 1, 2 or 3; and, wherein Ring $C_1$ is selected from the group consisting of a thienyl ring, a pyridinyl ring, a cyclohexyl ring, a cyclohexenyl ring, a cyclohexa-1,4-dienyl ring, a benzo[d][1,3]dioxolyl ring and a 2,3-dihydrobenzo[b][1,4]dioxinyl ring, wherein benzo[d][1,3]dioxolyl and 2,3-dihydrobenzo[b][1,4]dioxinyl, each having a benzo ring portion, are fused via said benzo portion; (b) $R_{20}$ and $R_{21}$ are each H; alternatively, $R_{20}$ and $R_{21}$ are each $C_1$-$C_3$ alkyl; (c) $R_{22}$ is selected from the group consisting of H, halogen, $C_1$-$C_4$ alkyl, $C_1$-$C_4$ alkoxy, $C_1$-$C_4$ haloalkyl, cyano, thienyl, furanyl, pyridinyl, pyrimidinyl and phenyl, wherein phenyl is optionally substituted with one or two halogen, $C_1$-$C_4$ alkyl or $C_1$-$C_4$ alkoxy substituents; (d) when one, two or three of $R_{23}$, $R_{24}$, $R_{25}$ and $R_{26}$ are each H, then three, two or one of $R_{23}$, $R_{24}$, $R_{25}$ and $R_{26}$, respectively, are each selected from hydroxyl, halogen, cyano, nitro, $C_1$-$C_8$ alkyl, $C_1$-$C_6$ alkoxy, $C_1$-$C_6$ alkoxyalkyl, $C_1$-$C_6$ alkoxyalkyl, $C_1$-$C_6$ difluoroalkoxy, $C_1$-$C_6$ trifluoroalkoxy, $C_1$-$C_4$ trifluoroalkyl, $C_2$-$C_6$ alkenyl, $C_2$-$C_4$ trifluoroalkenyl, amino, $C_1$-$C_4$ alkylamino, $C_1$-$C_4$ dialkylamino, $C_1$-$C_4$ aminoalkyl, $C_1$-$C_4$ alkylaminoalkyl or $C_1$-$C_4$ dialkylaminoalkyl; (e) when three of $R_{23}$, $R_{24}$, $R_{25}$ and $R_{26}$ are each H, then one of $R_{23}$, $R_{24}$, $R_{25}$ and $R_{26}$ is selected from phenyl, cyclopentyl, cyclopropyl, benzyloxy, $C_1$-$C_4$ cyclopentylalkoxy, $C_1$-$C_4$ cyclobutylalkoxy, cyclopentyloxy, pyrrolidinyl, piperidinyl, morpholinyl, $C_1$-$C_4$ morpholinylalkyl, thienyl, pyridinyl, pyrimidinyl, or amino, wherein amino is optionally disubstituted with one substituent selected from hydrogen or $C_1$-$C_6$ alkyl and the other is selected from phenyl, $C_1$-$C_4$ alkylcarbonyl, aminocarbonyl, $C_1$-$C_4$ alkylaminocarbonyl, $C_1$-$C_4$ dialkylaminocarbonyl, phenylcarbonyl, phenylaminocarbonyl, N-phenyl-N—$C_1$-$C_4$ alkyl-aminocarbonyl, $C_1$-$C_6$ alkylsulfonyl or phenylsulfonyl, and wherein each instance of phenyl is optionally substituted with one or two substituents selected from halogen, $C_1$-$C_4$ alkyl or $C_1$-$C_4$ alkoxy; or (f) $X_1$ is absent or is selected from the group consisting of H, cyano, $C_1$-$C_4$ alkyl, $C_1$-$C_4$ alkoxy, $C_1$-$C_4$ haloalkyl, $C_1$-$C_6$ hydroxylalkyl, $C_1$-$C_6$ alkoxyalkyl, $C_1$-$C_4$ morpholinylalkyl, amino, $C_1$-$C_4$ alkylamino, $C_1$-$C_4$ dialkylamino, $C_1$-$C_4$ aminoalkyl, $C_1$-$C_4$ alkylaminoalkyl, $C_1$-$C_4$ dialkylaminoalkyl, carboxy, $C_1$-$C_6$ alkoxycarbonyl, benzyloxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, aminosulfonylaminocarbonyl, $C_1$-$C_8$ alkylaminosulfonylaminocarbonyl, $C_1$-$C_8$ dialkylaminosulfonylaminocarbonyl, $C_1$-$C_8$ alkylsulfonylaminocarbonyl, phenylsulfonylaminocarbonyl, morpholinylcarbonyl and piperidinylcarbonyl.

5. The method of claim 1, wherein the nucleic acid construct comprises the nucleic acid residues of exon 6 of SMN or a fragment thereof downstream (3') to the start codon and upstream (5') of the nucleic acid residues of exon 7 of SMN, wherein the fragment of the nucleic acid residues of exon 6 of SMN comprises any number of nucleotides of exon 6 of SMN so long as in the mRNA transcript the first start codon and the stop codon upstream of the reporter gene coding sequence are maintained in the same contiguous open reading frame.

6. The method of claim 5, wherein the nucleic acid construct comprises the nucleic acid residues of intron 6 of SMN or a fragment thereof downstream (3') of the nucleic acid residues of exon 6 of SMN or a fragment thereof and upstream (5') of the nucleic acid residues of exon 7 of SMN, wherein the fragment of the nucleic acid residues of intron 6 of SMN comprises any number of nucleotides of intron 6 of SMN required for a functional, minimum intron.

7. The method of claim 1, further comprising contacting the host cell with a positive control.

8. The method of claim 7, wherein said positive control is Compound 1:

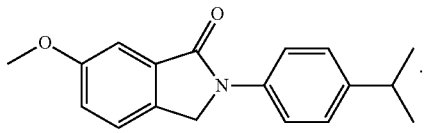 [SMILES: COc1ccc2c(c1)C(=O)N(c1ccc(C(C)C)cc1)C2]

9. A method for screening compounds for a compound that modulates the efficiency of viral programmed ribosomal frameshifting comprising:
   (a) contacting a compound with a composition comprising a cell-free extract and an mRNA transcript transcribed from a nucleic acid construct, wherein said nucleic acid construct comprises, in 5' to 3' order: (i) a start codon; (ii) the nucleic acid residues of exon 7 of SMN, wherein a single guanine residue is inserted after the $48^{th}$ nucleotide residue from the 5' end of exon 7 of SMN; (iii) the nucleic acid residues of intron 7 of SMN or a fragment thereof, wherein the fragment of the nucleic acid residues of intron 7 comprises any number of nucleotides of intron 7 of SMN required for a functional, minimum intron; (iv) a fragment of the nucleic acid residues of exon 8 of SMN; and (v) a reporter gene coding sequence lacking a start codon, wherein: (A) the reporter gene coding sequence is fused to the fragment of the nucleic acid residues of exon 8 of SMN such that the first codon of the reporter gene coding sequence and the start codon are out of frame with each other in the mRNA transcript transcribed from the nucleic acid construct; and (B) the production of the mRNA transcript generates a stop codon upstream from the reporter gene coding sequence in the region of the mRNA transcript that corresponds to the fragment of the nucleic acid residues of exon 8 of SMN; and (C) the start codon and the stop codon upstream from the reporter gene coding sequence in the mRNA transcript are in the same contiguous open reading frame; and
   (b) detecting the activity or amount of a fusion protein translated from the mRNA transcript, wherein an increase of 1.5-fold or more in the activity or amount of the fusion protein translated from the mRNA transcript in the presence of a compound when compared to (i) a previously determined reference range for a negative control, (ii) the activity or amount of the fusion protein translated from the mRNA transcript in the absence of the compound, or (iii) the activity or amount of the fusion protein translated from the mRNA transcript in the presence of a negative control indicates that the compound modulates the efficiency of programmed ribosomal frameshifting; and
   (c) contacting a compound that increases the activity or amount of the fusion protein translated from the mRNA transcript with a cell containing a virus that employs programmed ribosomal frameshifting and assaying the ability of the compound to decrease viral replication, wherein a decrease in viral replication of at least 1.5 log 10 in the presence of the compound indicates that a compound that modulates the efficiency of viral programmed ribosomal frameshifting is identified.

10. The method of claim 9, wherein the compound is selected from compounds of Formula (I) or Formula (II), wherein Formula (I) and Formula (II) have the following structures:

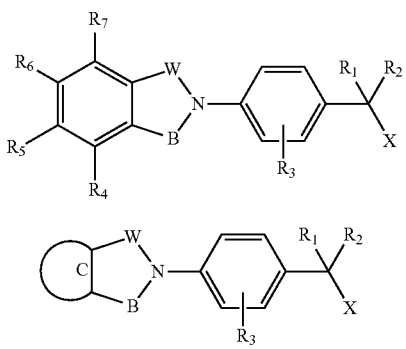

Formula (I)

Formula (II)

wherein,

W is selected from the group consisting of C(O), C(S), and $CH_2$;

B is $CH_2$ or $CH(C_nH_{2n+1})$, wherein n is an integer from 1 to 8;

Ring C is selected from the group consisting of a fused thienyl ring, a fused pyridinyl ring, and a fused cyclohexyl ring, any of which can be saturated or contain, one or two non-conjugated double bonds;

$R_1$ and $R_2$ are independently selected from the group consisting of H and $C_1$-$C_3$ alkyl, or $R_1$ and $R_2$ may be taken together with the carbon atom to which they are attached to form a $C_3$-$C_6$ cycloalkyl ring or a carbonyl group;

$R_3$ is selected from the group consisting of H, halogen, $C_1$-$C_4$ alkyl, $C_1$-$C_4$ alkoxy, $C_1$-$C_4$ haloalkyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy substituents;

$R_4$, $R_5$, $R_6$ and $R_7$ are independently selected from the group consisting of H, hydroxyl, halogen, CN, $NO_2$, sulfonamide, $C_1$-$C_8$ alkyl, $C_3$-$C_6$ cycloalkyl, cycloalkyloxy, $C_1$-$C_6$ alkoxy, $C_1$-$C_6$ haloalkoxy, $C_1$-$C_4$ haloalkyl, $C_2$-$C_8$ alkenyl, amino, $C_1$-$C_4$ alkylamino, $C_1$-$C_4$ dialkylamino, $C_3$-$C_6$ cycloalkylamino, morpholinyl, heteroaryl, arylamino, arylalkylamino, phenyl, C(O)R', NR'(COR"), $NR'SO_2R"$ and NR'(CONR"R'''), wherein R', R" and R''' are independently H, $C_1$-$C_6$ alkyl, phenyl, or substituted phenyl, and wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl, and the phenyl is optionally substituted with one or more substituents selected from the group consisting of halogen, $NO_2$, CN, $C_1$-$C_4$ alkyl, $C_1$-$C_4$ haloalkyl, and $C_1$-$C_4$ alkoxy, or $R_4$ and $R_5$, $R_5$ and $R_6$, or $R_6$ and $R_7$, taken together with the carbon to which they are attached, form a ring;

X is selected from the group consisting of H; CN; C(O)$OR_8$, wherein $R_8$ is H or $C_1$-$C_8$ alkyl, and $C_1$-$C_8$ alkyl optionally is substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, phenyl, and morpholinyl; C(O)$NR_9R_{10}$ or $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a heterocyclyl ring; $CH_2OR_{11}$, wherein $R_{11}$ is H, $C_1$-$C_8$ alkyl, or $C_3$-$C_6$ cycloalkyl, wherein $C_1$-$C_8$ alkyl is optionally substituted with one or more substituents selected from the group consisting of $C_1$-$C_4$ alkoxy, $C_1$-$C_4$ haloalkyl, $C_1$-$C_6$ dialkylamino, $C_1$-$C_6$ alkylamino, cycloalkylamino, and morpholinyl; $CH_2Z$, wherein Z is halogen; C(O)NHOH; C(O)NHCN; C(O)N($R_1$)$SO_2R_{13}$, wherein $R_{13}$ is $C_1$-$C_4$ alkyl, phenyl, or substituted phenyl; $C_1$-$C_8$ alkyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl, optionally substituted with one or more substituents selected from the group consisting of $C_1$-$C_4$ alkoxy, $C_1$-$C_4$ haloalkyl, $C_1$-$C_6$ dialkylamino, and $C_1$-$C_6$ alkylamino.

11. The method of claim 9, wherein the compound is selected from compounds of Formula (Ia) or Formula (IIa), wherein Formula (Ia) and Formula (IIa) have the following structures:

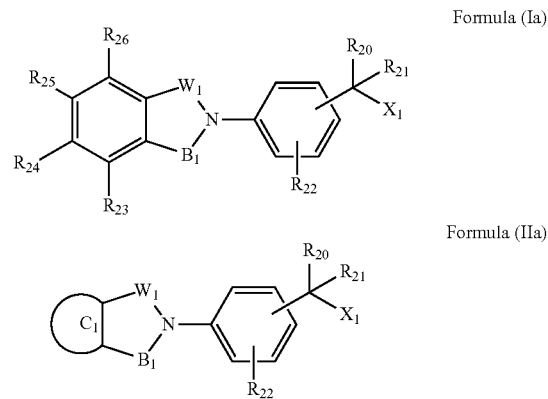

Formula (Ia)

Formula (IIa)

wherein, $W_1$ is selected from the group consisting of C(O), C(S), and $CH_2$;

$B_1$ is $CH_2$ or $CH(C_mH_{2m+1})$, wherein m is an integer from 1 to 8;

Ring $C_1$ is selected from the group consisting of a thienyl ring, a pyridinyl ring, a cyclohexyl ring, a benzo[d][1,3]dioxolyl ring and a 2,3-dihydrobenzo[b][1,4]dioxinyl ring, wherein benzo[d][1,3]dioxolyl and 2,3-dihydrobenzo[b][1,4]dioxinyl, each having a benzo ring portion, are fused via said benzo portion, and wherein any of the foregoing rings may optionally be fully or partially saturated;

$R_{20}$ and $R_{21}$ are independently selected from the group consisting of H and $C_1$-$C_3$ alkyl, or $R_{20}$ and $R_{21}$ may be taken together with the carbon atom to which they are attached to form a $C_3$-$C_6$ cycloalkyl ring or a carbonyl group;

$R_{22}$ is selected from the group consisting of H, halogen, $C_1$-$C_4$ alkyl, $C_1$-$C_4$ alkoxy, $C_1$-$C_4$ haloalkyl, cyano, nitro, heteroaryl, and phenyl optionally substituted with any combination of one to five halogen, nitro, cyano, $C_1$-$C_4$ alkyl, $C_1$-$C_4$ haloalkyl or $C_1$-$C_4$ alkoxy substituents;

$R_{23}$, $R_{24}$, $R_{25}$ and $R_{26}$ are independently selected from the group consisting of H, hydroxyl, halogen, cyano, nitro, sulfonamide, $C_1$-$C_8$ alkyl, $C_1$-$C_6$ alkoxy, $C_1$-$C_6$ alkoxyalkoxy, $C_1$-$C_6$ alkoxyalkyl, $C_1$-$C_6$ haloalkoxy, $C_1$-$C_4$ haloalkyl, $C_2$-$C_6$ alkenyl, $C_2$-$C_4$ haloalkenyl, formyl, $C_1$-$C_6$ alkylcarbonyl, amino, $C_1$-$C_4$ alkylamino, $C_1$-$C_4$ dialkylamino, $C_1$-$C_4$ aminoalkyl, $C_1$-$C_4$ alkylaminoalkyl, $C_1$-$C_4$ dialkylaminoalkyl, phenyl, $C_3$-$C_6$ cycloalkyl, $C_3$-$C_6$ cycloalkylalkyl, $C_3$-$C_6$ cycloalkylalkoxy, cycloalkyloxy, heterocyclyl, heterocyclylalkyl, heteroaryl, and phenylcarbonyl, wherein amino is optionally disubstituted with one substituent selected from hydrogen, $C_1$-$C_6$ alkyl or phenyl and the other is selected from formyl, phenyl, $C_3$-$C_6$ cycloalkyl, $C_1$-$C_6$ alkylcarbonyl, aminocarbonyl, $C_1$-$C_6$ alkylaminocarbonyl, $C_1$-$C_6$ dialkylaminocarbonyl, phenylcarbonyl, phenylaminocarbonyl, N-phenyl-N—$C_1$-$C_6$ alkyl-aminocarbonyl, $C_1$-$C_6$ alkylsulfonyl, aminosulfonyl, $C_1$-$C_6$ alkylaminosulfonyl, $C_1$-$C_6$ dialkylaminosulfonyl or phenylsulfonyl, wherein each instance of $C_1$-$C_6$ alkylcarbonyl is optionally substituted on the alkyl portion with one or more substituents selected from the group consisting of halogen, $C_1$-$C_4$ alkoxy, $C_1$-$C_6$ alkylamino, $C_1$-$C_6$ dialkylamino, cycloalkylamino and heterocyclyl, wherein each instance of phenyl is optionally substituted with one or more substituents selected from the group consisting of halogen, nitro, cyano, $C_1$-$C_4$ alkyl, $C_1$-$C_4$ haloalkyl and $C_1$-$C_4$ alkoxy, and alternatively, $R_{23}$ and $R_{24}$, $R_{24}$ and $R_{25}$ or $R_{25}$ and $R_{26}$ may be taken together with the carbons to which they are attached to form a $C_3$-$C_6$ cycloalkyl ring;

$X_1$ is absent or is selected from the group consisting of H, cyano, $C_1$-$C_8$ alkyl, $C_1$-$C_4$ alkoxy, amino, $C_1$-$C_4$ alkylamino, $C_1$-$C_4$ dialkylamino, carboxy, $C_1$-$C_8$ alkoxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, aminosulfonylaminocarbonyl, $C_1$-$C_8$ alkylaminosulfonylaminocarbonyl, $C_1$-$C_8$ dialkylaminosulfonylaminocarbonyl, $C_1$-$C_8$ alkylsulfonylaminocarbonyl, phenylsulfonylaminocarbonyl and heterocyclylcarbonyl, wherein $C_1$-$C_4$ alkoxy and the $C_1$-$C_8$ alkoxy portion of $C_1$-$C_8$ alkoxycarbonyl is optionally substituted with one or more substituents selected from the group consisting of halogen, $C_1$-$C_4$ alkoxy, $C_1$-$C_4$ haloalkyl, amino, $C_1$-$C_6$ alkylamino, $C_1$-$C_6$ dialkylamino, cycloalkylamino, phenyl and heterocyclyl, wherein $C_1$-$C_8$ alkyl is optionally substituted with one or more substituents selected from the group consisting of halogen, hydroxyl, $C_1$-$C_4$ haloalkyl, $C_2$-$C_8$ alkenyl, $C_1$-$C_6$ alkoxy, $C_1$-$C_4$ alkoxyalkoxy, $C_3$-$C_6$ cycloalkyloxy, amino, $C_1$-$C_6$ alkylamino, $C_1$-$C_6$ dialkylamino, cycloalkylamino, aminocarbonyl, $C_1$-$C_6$ alkylaminocarbonyl, $C_1$-$C_6$ dialkylaminocarbonyl, hydroxylaminocarbonyl, cyanoaminocarbonyl, $C_1$-$C_6$ alkylsulfonylaminocarbonyl, phenylsulfonylaminocarbonyl and heterocyclyl, wherein $C_1$-$C_4$ alkoxy or $C_2$-$C_8$ alkenyl are each further optionally substituted with one or more substituents selected from the group consisting of $C_1$-$C_4$ alkoxy, $C_1$-$C_4$ haloalkyl, amino, $C_1$-$C_6$ alkylamino and $C_1$-$C_6$ dialkylamino.

12. The method of claim 11, wherein: (a) m is an integer selected from 1, 2 or 3; and, wherein Ring $C_1$ is selected from the group consisting of a thienyl ring, a pyridinyl ring, a cyclohexyl ring, a cyclohexenyl ring, a cyclohexa-1,4-dienyl ring, a benzo[d][1,3]dioxolyl ring and a 2,3-dihydrobenzo[b][1,4]dioxinyl ring, wherein benzo[d][1,3]dioxolyl and 2,3-dihydrobenzo[b][1,4]dioxinyl, each having a benzo ring portion, are fused via said benzo portion; (b) $R_{20}$ and $R_{21}$ are each H; alternatively, $R_{20}$ and $R_{21}$ are each $C_1$-$C_3$ alkyl; (c) $R_{22}$ is selected from the group consisting of H, halogen, $C_1$-$C_4$ alkyl, $C_1$-$C_4$ alkoxy, $C_1$-$C_4$ haloalkyl, cyano, thienyl, furanyl, pyridinyl, pyrimidinyl and phenyl, wherein phenyl is optionally substituted with one or two halogen, $C_1$-$C_4$ alkyl or $C_1$-$C_4$ alkoxy substituents; (d) when one, two or three of $R_{23}$, $R_{24}$, $R_{25}$ and $R_{26}$ are each H, then three, two or one of $R_{23}$, $R_{24}$, $R_{25}$ and $R_{26}$, respectively, are each selected from hydroxyl, halogen, cyano, nitro, $C_1$-$C_8$ alkyl, $C_1$-$C_6$ alkoxy, $C_1$-$C_6$ alkoxyalkoxy, $C_1$-$C_6$ alkoxyalkyl, $C_1$-$C_6$ difluoroalkoxy, $C_1$-$C_6$ trifluoroalkoxy, $C_1$-$C_4$ trifluoroalkyl, $C_2$-$C_6$ alkenyl, $C_2$-$C_4$ trifluoroalkenyl, amino, $C_1$-$C_4$ alkylamino, $C_1$-$C_4$ dialkylamino, $C_1$-$C_4$ aminoalkyl, $C_1$-$C_4$ alkylaminoalkyl or $C_1$-$C_4$ dialkylaminoalkyl; (e) when three of $R_{23}$, $R_{24}$, $R_{25}$ and $R_{26}$ are each H, then one of $R_{23}$, $R_{24}$, $R_{25}$ and $R_{26}$ is selected from phenyl, cyclopentyl, cyclopropyl, benzyloxy, $C_1$-$C_4$ cyclopentylalkoxy, $C_1$-$C_4$ cyclobutylalkoxy, cyclopentyloxy, pyrrolidinyl, piperidinyl, morpholinyl, $C_1$-$C_4$ morpholinylalkyl, thienyl, pyridinyl, pyrimidinyl, or amino, wherein amino is optionally disubstituted with one substituent selected from hydrogen or $C_1$-$C_6$ alkyl and the other is selected from phenyl, $C_1$-$C_4$ alkylcarbonyl, aminocarbonyl, $C_1$-$C_4$ alkylaminocarbonyl, $C_1$-$C_4$ dialkylaminocarbonyl, phenylcarbonyl, phenylaminocarbonyl, N-phenyl-N—$C_1$-$C_4$ alkyl-aminocarbonyl, $C_1$-$C_6$ alkylsulfonyl or phenylsulfonyl, and wherein each instance of phenyl is optionally substituted with one or two substituents selected from halogen, $C_1$-$C_4$ alkyl or $C_1$-$C_4$ alkoxy; or (f) $X_1$ is absent or is selected from the group consisting of H, cyano, $C_1$-$C_4$ alkyl, $C_1$-$C_4$ alkoxy, $C_1$-$C_4$ haloalkyl, $C_1$-$C_6$ hydroxylalkyl, $C_1$-$C_6$ alkoxyalkyl, $C_1$-$C_4$ morpholinylalkyl, amino, $C_1$-$C_4$ alkylamino, $C_1$-$C_4$ dialkylamino, $C_1$-$C_4$ aminoalkyl, $C_1$-$C_4$ alkylaminoalkyl, $C_1$-$C_4$ dialkylaminoalkyl, carboxy, $C_1$-$C_6$ alkoxycarbonyl, benzyloxycarbonyl, aminocarbonyl, $C_1$-$C_8$ alkylaminocarbonyl, $C_1$-$C_8$ dialkylaminocarbonyl, hydroxylaminocarbonyl, cyanoaminocarbonyl, phenylaminocarbonyl, aminosulfonylaminocarbonyl, $C_1$-$C_8$ alkylaminosulfonylaminocarbonyl $C_1$-$C_8$ dialkylaminosulfonylaminocarbonyl, $C_1$-$C_8$ alkylsulfonylaminocarbonyl, phenylsulfonylaminocarbonyl, morpholinylcarbonyl and piperidinylcarbonyl.

13. The method of claim 9, wherein the nucleic acid construct comprises the nucleic acid residues of exon 6 of SMN or a fragment thereof downstream (3') to the start codon and upstream (5') of the nucleic acid residues of exon 7 of SMN, wherein the fragment of the nucleic acid residues of exon 6 of SMN comprises any number of nucleotides of exon 6 of SMN so long as in the mRNA transcript the first start codon and the stop codon upstream of the reporter gene coding sequence are maintained in the same contiguous open reading frame.

14. The method of claim 13, wherein the nucleic acid construct comprises the nucleic acid residues of intron 6 of SMN or a fragment thereof downstream (3') of the nucleic acid residues of exon 6 of SMN or a fragment thereof and upstream (5') of the nucleic acid residues of exon 7 of SMN, wherein the fragment of the nucleic acid residues of intron 6 of SMN comprises any number of nucleotides of intron 6 of SMN required for a functional, minimum intron.

15. The method of claim 9, further comprising contacting the cell-free extract with a positive control.

16. The method of claim 15, wherein said positive control is Compound 1:

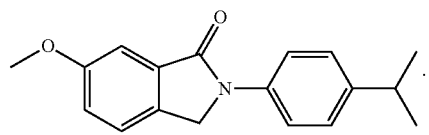 [SMILES: COc1ccc2c(c1)C(=O)N(c1ccc(C(C)C)cc1)C2]

* * * * *

SEQUENCE LISTING

```
<160> NUMBER OF SEQ ID NOS: 11

<210> SEQ ID NO 1
<211> LENGTH: 11
<212> TYPE: DNA
<213> ORGANISM: Artificial Sequence
<220> FEATURE:
<223> OTHER INFORMATION: DNA corresponding to a region of the SMN2 gene
      starting from the 5' end of exon 6

<400> SEQUENCE: 1
ataattcccc c                                                          11

<210> SEQ ID NO 2
<211> LENGTH: 6
<212> TYPE: DNA
<213> ORGANISM: Artificial Sequence
<220> FEATURE:
<223> OTHER INFORMATION: DNA corresponding to a region of the SMN2 gene
``` ending at nucleic acid residue 23 of exon 8

<400> SEQUENCE: 2 cagcac                                                                    6

<210> SEQ ID NO 3
<211> LENGTH: 28
<212> TYPE: DNA
<213> ORGANISM: Artificial Sequence
<220> FEATURE:
<223> OTHER INFORMATION: Forward Primer used to generate DNA
      corresponding to a region of the SMN2 gene

<400> SEQUENCE: 3
cgcggatcca taattccccc accacctc                                           28

<210> SEQ ID NO 4
<211> LENGTH: 28
<212> TYPE: DNA
<213> ORGANISM: Artificial Sequence
<220> FEATURE:
<223> OTHER INFORMATION: Reverse Primer used to generate DNA
      corresponding to a region of the SMN2 gene

<400> SEQUENCE: 4
cgcggatccg tgctgctcta tgccagca                                           28

<210> SEQ ID NO 5
<211> LENGTH: 6
<212> TYPE: DNA
<213> ORGANISM: Artificial Sequence
<220> FEATURE:
<223> OTHER INFORMATION: BamHI site at the 5 prime end of exon 6 of the
      SMN2 gene

<400> SEQUENCE: 5 ggatcc                                                                    6

<210> SEQ ID NO 6
<211> LENGTH: 70
<212> TYPE: DNA
<213> ORGANISM: Artificial Sequence
<220> FEATURE:
<223> OTHER INFORMATION: 5 prime deg UTR added to the modified vector
      using the HindIII site and the BamHI site

<400> SEQUENCE: 6
tagcttctta cccgtactcc accgttggca gcacgatcgc acgtcccacg tgaaccattg        60
gtaaaccctg                                                               70

<210> SEQ ID NO 7
<211> LENGTH: 119
<212> TYPE: DNA
<213> ORGANISM: Artificial Sequence
<220> FEATURE:
<223> OTHER INFORMATION: 3 prime deg UTR added to the modified vector
      using the HindIII site and the BamHI site

<400> SEQUENCE: 7
tcgaaagtac aggactagcc ttcctagcaa ccgcgggctg ggagtctgag acatcactca        60
agatatatgc tcggtaacgt atgctctagc catctaacta ttccctatgt cttataggg       119

<210> SEQ ID NO 8
<211> LENGTH: 7
<212> TYPE: DNA

```
<213> ORGANISM: Artificial Sequence
<220> FEATURE:
<223> OTHER INFORMATION: Seven nucleotides from the inserted guanine
      residue to the last nucleotide of exon 7 missing
      in the clones containing the SMN1-G minigene
      fragment

<400> SEQUENCE: 8 gtaagga                                                              7

<210> SEQ ID NO 9
<211> LENGTH: 6
<212> TYPE: DNA
<213> ORGANISM: Artificial Sequence
<220> FEATURE:
<223> OTHER INFORMATION: Sequence element generated  through the
      G-insertion in the SMN1-G version of the minigene

<400> SEQUENCE: 9 gtaagg                                                               6

<210> SEQ ID NO 10
<211> LENGTH: 6
<212> TYPE: DNA
<213> ORGANISM: Artificial Sequence
<220> FEATURE:
<223> OTHER INFORMATION: 5' end of intron 7 of the SMN1-G version of the
      minigene

<400> SEQUENCE: 10 gtaagt                                                               6

<210> SEQ ID NO 11
<211> LENGTH: 8266
<212> TYPE: DNA
<213> ORGANISM: Artificial Sequence
<220> FEATURE:
<223> OTHER INFORMATION: DNA sequence of the minigene from the SMN-G
      minigene construct

<400> SEQUENCE: 11
tagcttctta cccgtactcc accgttggca gcacgatcgc acgtcccacg tgaaccattg      60
gtaaaccctg atgggatcca taattccccc accacctccc atatgtccag attctcttga    120
tgatgctgat gctttgggaa gtatgttaat tcatggtac atgagtggct atcatactgg     180
ctattatatg gtaagtaatc actcagcatc ttttcctgac aatttttttg tagttatgtg    240
actttgtttt gtaaatttat aaatactac ttgcttctct ctttatatta ctaaaaaata     300
aaaataaaaa aatacaactg tctgaggctt aaattactct tgcattgtcc ctaagtataa    360
ttttagttaa ttttaaaaag cttttcatgct attgttagat tattttgatt atacactttt   420
gaattgaaat tatactttt ctaaataatg ttttaatctc tgatttgaaa ttgattgtag     480
ggaatggaaa agatgggata attttttcata aatgaaaaat gaaattcttt tttttttttt   540
tttttttttg agacggagtc ttgctctgtt gcccaggctg gagtgcaatg gcgtgatctt    600
ggctcacagc aagctctgcc tcctggattc acgccattct cctgcctcag cctcagaggt    660
agctgggact acaggtgcct gccaccacgc ctgtctaatt ttttgtattt tttgtaaag    720 acagggtttc actgtgttag ccaggatggt ctcaatctcc tgaccccgtg atccacccgc   780
ctcggccttc caagagaaat gaatttttt taatgcacaa agatctgggg taatgtgtac    840
cacattgaac cttgggggagt atggcttcaa acttgtcact ttatacgtta gtctcctacg   900
gacatgttct attgtatttt agtcagaaca tttaaaatta ttttattttta ttttattttt   960
```

```
tttttttttt tgagacggag tctcgctctg tcacccaggc tggagtacag tggcgcagtc    1020
tcggctcact gcaagctccg cctcccgggt tcacgccatt ctcctgcctc agcctctccg    1080
agtagctggg actacaggcg cccgccacca cgcccggcta attttttttt atttttagta    1140
gagacggggt ttcaccgtgg tctcgatctc ctgacctcgt gatccacccg cctcggcctc    1200
ccaaagtgct gggattacaa gcgtgagcca ccgcgcccgg cctaaaatta ttttaaaag     1260 taagctcttg tgccctgcta aaattatgat gtgatattgt aggcacttgt attttagta    1320 aattaatata aagaaacaa ctgacttaaa ggtgtatgtt tttaaatgta tcatctgtgt    1380 gtgccccat taatattctt atttaaaagt taaggccaga catggtggct tacaactgta    1440
atcccaacag tttgtgaggc cgaggcaggc agatcacttg aggtcaggag tttgagacca    1500
gcctggccaa catgatgaaa ccttgtctct actaaaaata ccaaaaaaaa tttagccagg    1560
catggtggca catgcctgta atccgagcta cttgggaggc tgtggcagga aaattgcttt    1620
aatctgggag gcagaggttg cagtgagttg agattgtgcc actgcactcc acccttggtg    1680
acagagtgag attccatctc aaaaaaagaa aaaggcctgg cacggtggct cacacctata    1740
atcccagtac tttgggaggt agaggcaggt ggatcacttg aggttaggag ttcaggacca    1800
gcctggccaa catggtgact actccatttc tactaaatac acaaaactta gcccagtggc    1860
gggcagttgt aatcccagct acttgagagg ttgaggcagg agaatcactt gaacctggga    1920
ggcagaggtt gcagtgagcc gagatcacac cgctgcactc tagcctggcc aacagagtga    1980
gaatttgcgg agggaaaaaa aagtcacgct tcagttgttg tagtataacc ttggtatatt    2040
gtatgtatca tgaattcctc attttaatga ccaaaaagta ataaatcaac agcttgtaat    2100
ttgttttgag atcagttatc tgactgtaac actgtaggct tttgtgtttt ttaaattatg    2160
aaatatttga aaaaaataca taatgtatat ataaagtatt ggtataattt atgttctaaa    2220
taactttctt gagaaataat tcacatggtg tgcagtttac cttgaaagt atacaagttg    2280 gctgggcaca atggctcacg cctgtaatcc cagcactttg ggaggccagg caggtggat    2340 cacgaggtca ggagatcgag accatcctgg ctaacatggt gaaacccgt ctctactaaa    2400 agtacaaaaa caaattagcc gggcatgttg gcgggcacct tttgtcccag ctgctcggga    2460
ggctgaggca ggagagtggc gtgaacccag gaggtggagc ttgcagtgag ccgagattgt    2520
gccagtgcac tccagcctgg gcgacagagc gagactctgt ctcaaaaaat aaaataaaaa    2580
agaaagtata caagtcagtg gttttggttt tcagttatgc aaccatcact acaatttaag    2640
aacattttca tcaccccaaa aagaaaccct gttaccttca ttttcccag ccctaggcag     2700 tcagtacact ttctgtctct atgaatttgt ctatttaga tattatatat aaacggaatt    2760
atacgatatg tggtctttg tgtctggctt ctttcactta gcatgctatt ttcaagattc    2820
atccatgctg tagaatgcac cagtactgca ttccttctta ttgctgaata ttctgttgtt    2880
tggttatatc acattttatc cattcatcag ttcatggaca tttaggttgt ttttattttt    2940
gggctataat gaataatgtt gctatgaaca ttcgtttgtg ttctttttgt ttttttggtt    3000
tttgggtttt ttttgttttt gttttgtttt ttgagacagt cttgctctgt ctcctaagct    3060
ggagtgcagt ggcatgatct tggcttactg caagctctgc ctcccgggtt cacaccattc    3120
tcctgcctca gcccgacaag tagctgggac tacaggcgtg tgccaccatg cacggctaat    3180 ttttgtatt tttagtagag atggggtttc accgtgttag ccaggatggt ctcgatctcc    3240
tgacctcgtg atctgcctgc ctaggcctcc caaagtgctg ggattacagg cgtgagccac    3300
```

-continued

```
tgcacctggc cttaagtgtt tttaatacgt cattgcctta agctaacaat tcttaacctt    3360
tgttctactg aagccacgtg gttgagatag gctctgagtc tagcttttaa cctctatctt    3420
tttgtcttag aaatctaagc agaatgcaaa tgactaagaa taatgttgtt gaaataacat    3480
aaaataggtt ataactttga tactcattag taacaaatct ttcaatacat cttacggtct    3540
gttaggtgta gattagtaat gaagtgggaa gccactgcaa gctagtatac atgtagggaa    3600
agatagaaag cattgaagcc agaagagaga cagaggacat tgggctaga tctgacaaga    3660 aaaacaaatg ttttagtatt aatttttgac tttaaatttt ttttttattt agtgaatact    3720
ggtgtttaat ggtctcattt taataagtat gacacaggta gtttaaggtc atatatttta    3780
tttgatgaaa ataaggtata ggccgggcac ggtggctcac acctgtaatc ccagcacttt    3840
gggaggccga ggcaggcgga tcacctgagg tcgggagtta gagactagcc tcaacatgga    3900 gaaacccgt ctctactaaa aaaaatacaa aattaggcgg gcgtggtggt gcatgcctgt    3960
aatcccagct actcaggagg ctgaggcagg agaattgctt gaacctggga ggtggaggtt    4020
gcggtgagcc gagatcacct cattgcactc cagcctgggc aacaagagca aaactccatc    4080
tcaaaaaaaa aaaaataagg tataagcggg ctcaggaaca tcattggaca tactgaaaga    4140
agaaaaatca gctgggcgca gtggctcacg ccggtaatcc caacactttg ggaggccaag    4200
gcaggcgaat cacctgaagt cgggagttcc agatcagcct gaccaacatg gagaaaccct    4260
gtctctacta aaaatacaaa actagccggg catggtggcg catgcctgta atcccagcta    4320
cttgggaggc tgaggcagga gaattgcttg aaccgagaag gcggaggttg cggtgagcca    4380
agattgcacc attgcactcc agcctgggca acaagagcga aactccgtct caaaaaaaaa    4440
aggaagaaaa atatttttt aaattaatta gtttatttat ttttaagat ggagttttgc    4500 cctgtcaccc aggctgggt gcaatggtgc aatctcggct cactgcaacc tccgcctcct    4560
gggttcaagt gattctcctg cctcagcttc ccgagtagct gtgattacag ccatatgcca    4620
ccacgcccag ccagttttgt gttttgtttt gttttttgtt ttttttttt gagagggtgt    4680 cttgctctgt cccccaagct ggagtgcagc ggcgcgatct ggctcactg caagctctgc    4740 ctcccaggtt cacaccattc tcttgcctca gcctcccgag tagctgggac tacaggtgcc    4800
cgccaccaca cccggctaat tttttttgtgt tttagtaga gatggggttt cactgtgtta    4860
gccaggatgg tctcgatctc ctgaccttt gatccacccg cctcagcctc ccaagtgct    4920 gggattatag gcgtgagcca ctgtgcccgg cctagtcttg tatttttagt agagtcggga    4980
tttctccatg ttggtcaggc tgttctccaa atccgacctc aggtgatccg cccgccttgg    5040
cctccaaaag tgcaaggcaa ggcattacag gcatgagcca ctgtgaccgg caatgttttt    5100
aaatttttta catttaaatt ttatttttta gagaccaggt ctcactctat tgctcaggct    5160
ggagtgcaag ggcacattca cagctcactg cagccttgac ctccagggct caagcagtcc    5220
tctcacctca gtttcccgag tagctgggac tacagtgata atgccactgc acctggctaa    5280 ttttatttt tatttattta tttttttttg agacagagtc ttgctctgtc acccaggctg    5340
gagtgcagtg gtgtaaatct cagctcactg cagcctccgc ctcctgggtt caagtgattc    5400
tcctgcctca acctcccaag tagctgggat tagaggtccc caccaccatg cctggctaat    5460
tttttgtact ttcagtagaa acggggtttt gccatgttgg ccaggctgtt ctcgaactcc    5520
tgagctcagg tgatccaact gtctcggcct cccaaagtgc tgggattaca ggcgtgagcc    5580
actgtgccta gcctgagcca ccacgccggc ctaattttta aatttttgt agagacaggt    5640 tctcattatg ttgcccaggg tggtgtcaag ctccaggtct caagtgatcc cctacctcc    5700
```

```
gcctcccaaa gttgtgggat tgtaggcatg agccactgca agaaaacctt aactgcagcc    5760
taataattgt tttctttggg ataacttta aagtacatta aaagactatc aacttaattt     5820
ctgatcatat tttgttgaat aaaataagta aaatgtcttg tgaaacaaaa tgctttttaa    5880
catccatata aagctatcta tatatagcta tctatatcta tatagctatt tttttaact    5940 tcctttattt tccttacagg gttttagaca aaatcaaaaa gaaggaaggt gctcacattc    6000
cttaaatgta aggagtaagt ctgccagcat tatgaaagtg aatcttactt ttgtaaaact    6060
ttatggtttg tggaaaacaa atgttttga acatttaaaa agttcagatg ttagaaagtt     6120
gaaaggttaa tgtaaaacaa tcaatattaa agaattttga tgccaaaact attagataaa    6180
aggttaatct acatccctac tagaattctc atacttaact ggttggttgt gtggaagaaa    6240
catactttca aataaagag ctttaggata tgatgccatt ttatatcact agtaggagaa     6300
ccagcagact tttttttatt gtgatatggg ataacctagg catactgcac tgtacactct    6360
gacatatgaa gtgctctagt caagtttaac tggtgtccac agaggacatg gtttaactgg    6420
aattcgtcaa gcctctggtt ctaatttctc atttgcagga aatgctggca tagagcagca    6480
cggatccgaa gacgccaaaa acataaagaa aggcccggcg ccattctatc ctctagagga    6540
tggaaccgct ggagagcaac tgcataaggc tatgaagaga tacgccctgg ttcctggaac    6600
aattgctttt acagatgcac atatcgaggt gaacatcacg tacgcggaat acttcgaaat    6660
gtccgttcgg ttggcagaag ctatgaaacg atatgggctg aatacaaatc acagaatcgt    6720
cgtatgcagt gaaaactctc ttcaattctt tatgccggtg ttgggcgcgt tatttatcgg    6780
agttgcagtt gcgcccgcga acgacattta taatgaacgt gaattgctca acagtatgaa    6840
catttcgcag cctaccgtag tgtttgtttc caaaaagggg ttgcaaaaaa ttttgaacgt    6900
gcaaaaaaaa ttaccaataa tccagaaaat tattatcatg gattctaaaa cggattacca    6960
gggatttcag tcgatgtaca cgttcgtcac atctcatcta cctcccggtt ttaatgaata    7020
cgattttgta ccagagtcct ttgatcgtga caaaacaatt gcactgataa tgaattcctc    7080
tggatctact gggttaccta agggtgtggc ccttccgcat agaactgcct gcgtcagatt    7140
ctcgcatgcc agagatccta ttttggcaa tcaaatcatt ccggatactg cgattttaag    7200
tgttgttcca ttccatcacg gttttggaat gtttactaca ctcggatatt tgatatgtgg    7260
atttcgagtc gtcttaatgt atagatttga agaagagctg ttttacgat cccttcagga    7320 ttacaaaatt caaagtgcgt tgctagtacc aaccctattt tcattcttcg ccaaaagcac    7380
tctgattgac aaatacgatt tatctaattt acacgaaatt gcttctgggg gcgcacctct    7440
ttcgaaagaa gtcggggaag cggttgcaaa acgcttccat cttccaggga tacgacaagg    7500
atatgggctc actgagacta catcagctat tctgattaca cccgagggg atgataaacc    7560 gggcgcggtc ggtaaagttg ttccattttt tgaagcgaag gttgtggatc tggataccgg    7620
gaaaacgctg ggcgttaatc agagaggcga attatgtgtc agaggaccta tgattatgtc    7680
cggttatgta aacaatccgg aagcgaccaa cgccttgatt gacaaggatg gatggctaca    7740
ttctggagac atagcttact gggacgaaga cgaacacttc ttcatagttg accgcttgaa    7800
gtctttaatt aaatacaaag gatatcaggt ggccccgct gaattggaat cgatattgtt    7860
acaacacccc aacatcttcg acgcgggcgt ggcaggtctt cccgacgatg acgccggtga    7920
acttcccgcc gccgttgttg ttttggagca cggaaagacg atgacggaaa aagagatcgt    7980
ggattacgtc gccagtcaag taacaaccgc gaaaaagttg cgcggaggag ttgtgtttgt    8040
```

```
ggacgaagta ccgaaaggtc ttaccggaaa actcgacgca agaaaaatca gagagatcct    8100
cataaaggcc aagaagggcg gaaagtccaa attgcgcggc cgctaaatcg aaagtacagg    8160
actagccttc ctagcaaccg cgggctggga gtctgagaca tcactcaaga tatatgctcg    8220
gtaacgtatg ctctagccat ctaactattc cctatgtctt ataggg                   8266
```